US012565504B2

(12) United States Patent
Genung et al.

(10) Patent No.: US 12,565,504 B2
(45) Date of Patent: Mar. 3, 2026

(54) SPIROCYCLIC O-GLYCOPROTEIN-2-ACETAMIDO-2-DEOXY-3-D-GLUCOPYRANOSIDASE INHIBITORS

(71) Applicant: BIOGEN MA INC., Cambridge, MA (US)

(72) Inventors: Nathan Genung, Charlestown, MA (US); Kevin M. Guckian, Northborough, MA (US); Lei Zhang, Westford, MA (US); Zhili Xin, Cambridge, MA (US); Jeffrey Vessels, Marlborough, MA (US); Ryan Gianatassio, Everett, MA (US)

(73) Assignee: BIOGEN MA INC., Cambridge, MA (US)

( * ) Notice: Subject to any disclaimer, the term of this patent is extended or adjusted under 35 U.S.C. 154(b) by 914 days.

(21) Appl. No.: 17/772,646

(22) PCT Filed: Oct. 28, 2020

(86) PCT No.: PCT/US2020/057740

§ 371 (c)(1),
(2) Date: Apr. 28, 2022

(87) PCT Pub. No.: WO2021/086966

PCT Pub. Date: May 6, 2021

(65) Prior Publication Data

US 2023/0060003 A1 Feb. 23, 2023

Related U.S. Application Data

(60) Provisional application No. 62/927,268, filed on Oct. 29, 2019.

(51) Int. Cl.
*C07D 491/107* (2006.01)
*C07D 417/06* (2006.01)
*C07D 491/20* (2006.01)

(52) U.S. Cl.
CPC ....... *C07D 491/107* (2013.01); *C07D 417/06* (2013.01); *C07D 491/20* (2013.01)

(58) Field of Classification Search
CPC . C07D 491/107; C07D 417/06; C07D 491/20
See application file for complete search history.

(56) References Cited

FOREIGN PATENT DOCUMENTS

WO 2018/141984 A1 8/2018

OTHER PUBLICATIONS

Cancer and Metastasis Reviews (1998), 17(1), 91-106.*
Science (1999), vol. 286, 531-537.*
International Search Report and Written Opinion for Application No. PCT/US2020/057740, dated Feb. 5, 2021, 8 pages.

* cited by examiner

*Primary Examiner* — Rebecca L Anderson
(74) *Attorney, Agent, or Firm* — McCarter & English, LLP; Xin Zhang; Zhongyu Wang

(57) ABSTRACT

Described herein are compounds represented by formula (I) or formula (Ia) or a pharmaceutically acceptable salt thereof, pharmaceutical compositions comprising the same and methods of preparing and using the same. The variables $R^1$, $R^2$, $R^3$, $R^4$, $R^5$, $R^6$, $Y^1$, $Y^2$, D, E, $G^1$, $G^2$, n and p are as defined herein.

(I)

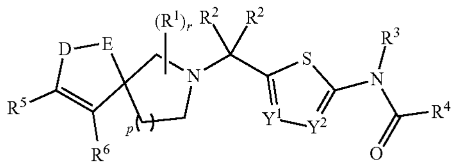

(Ia)

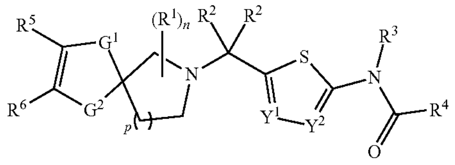

20 Claims, No Drawings

SPIROCYCLIC O-GLYCOPROTEIN-2-ACETAMIDO-2-DEOXY-3-D-GLUCOPYRANOSIDASE INHIBITORS

RELATED APPLICATIONS

This application is a 35 U.S.C. § 371 national stage filing of International Application No. PCT/US2020/057740, filed on Oct. 28, 2020, which in turn claims the benefit of the filing date, under 35 U.S.C. § 119(e), of U.S. Provisional Patent Application No. 62/927,268, filed on Oct. 29, 2019. The entire contents of the aforementioned applications are incorporated herein by reference.

BACKGROUND

A wide range of cellular proteins, both nuclear and cytoplasmic, are post-translationally modified by the addition of the monosaccharide 2-acetamido-2-deoxy-β-D-glucopyranoside (β-N-acetyl glucosamine) which is attached via an O-glycosidic linkage. This monosaccharide is generally referred to as O-linked N-acetylglucosamine or O-GlcNAc. The enzyme responsible for post-translationally linking β-N-acetylglucosamine (GlcNAc) to specific serine and threonine residues of numerous nucleocytoplasmic proteins is O-GlcNAc transferase (OGTase). A second enzyme, known as O-glycoprotein-2-acetamido-2-deoxy-3-D-glucopyranosidase or O-GlcNAcase or OGA, removes this post-translational modification to liberate proteins, making the O-GlcNAc-modification a dynamic cycle occurring several times during the lifetime of a protein.

O-GlcNAc-modified proteins regulate a wide range of vital cellular functions including, e.g., transcription, proteasomal degradation and cellular signaling. O-GlcNAc is also found on many structural proteins, including the cytoskeletal protein "tau" which is responsible for stabilizing a key cellular network of microtubules that is essential for distributing proteins and nutrients within neurons. Importantly, tau has been clearly implicated in the etiology of several diseases including tauopathies, Alzheimer's disease, Parkinson's disease, dementia and cancer.

It is well established that Alzheimer's disease and a number of related tauopathies including Progressive Supranuclear Palsy (PSP) and amyotrophic lateral sclerosis (ALS) are characterized, in part, by the development of neurofibrillary tangles (NFTs). These NFTs are aggregates of paired helical filaments (PHFs) and are composed of an abnormal form of tau. In AD patients, tau becomes hyperphosphorylated, thereby disrupting its normal function, forming PHFs and ultimately aggregating to form NFTs.

Six isoforms of tau are found in the human brain. In AD patients, all six isoforms of tau are found in NFTs, and all are markedly hyperphosphorylated. Tau in healthy brain tissue bears only 2 or 3 phosphate groups, whereas those found in the brains of AD patients bear, on average, 8 phosphate groups.

It has recently emerged that increases in phosphorylation levels result in decreased O-GlcNAc levels and conversely, increased O-GlcNAc levels correlate with decreased phosphorylation levels. It has been shown that decreased glucose availability in brain leads to tau hyperphosphorylation. The gradual impairment of glucose transport and metabolism leads to decreased O-GlcNAc and hyperphosphorylation of tau (and other proteins). Accordingly, the inhibition of O-GlcNAcase, which prevents hyperphosphorylation of tau by preventing removal of O-GlcNac from tau, should compensate for the age-related impairment of glucose metabolism within the brains of health individuals as well as patients suffering from Alzheimer's disease or related neurodegenerative diseases.

However, a major challenge in developing inhibitors for blocking the function of mammalian glycosidases, including O-GlcNAcase, is the large number of functionally related enzymes present in tissues of higher eukaryotes. Accordingly, the use of non-selective inhibitors in studying the cellular and organismal physiological role of one particular enzyme is complicated because complex phenotypes arise from the concomitant inhibition of such functionally related enzymes. In the case of β-N-acetylglucosaminidases, existing compounds that act to block O-GlcNAcase function are non-specific and act potently to inhibit the lysosomal β-hexosaminidases.

In view of foregoing technical challenge and given the potential for regulation of O-GlcNAcase for treatment of AD, tauopathies and other neurological diseases, there remains a need for development of potent and selective O-GlcNAcase inhibitors.

SUMMARY

Described herein are compounds that are useful treating various diseases, disorders and medical conditions, including but not limited to those associated with proteins that are modified by O-GlcNAcase.

A first embodiment of a compound of the present invention is represented by the following structural formula:

(I)

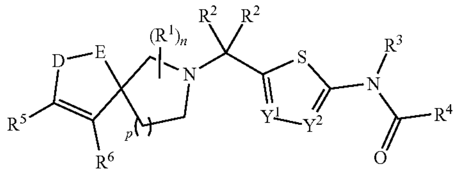

(I)

or a pharmaceutically acceptable salt thereof, wherein:

$Y^1$ and $Y^2$ are each $CR^c$ or N, wherein at least one of $Y^1$ or $Y^2$ is N;

$R^c$ is —H, halo, $C_1$-$C_4$ alkyl, or $C_1$-$C_4$ haloalkyl;

p is 1 or 2;

n is 0 or an integer from 1 to 8;

when n is other than 0, $R^1$, for each occurrence, is independently halo, $C_1$-$C_4$ alkyl, $C_1$-$C_4$ haloalkyl, or $C_1$-$C_4$ alkoxy;

$R^2$, for each occurrence, is independently —H, halo, $C_1$-$C_4$ alkyl, $C_1$-$C_4$ haloalkyl, $C_3$-$C_{10}$ cycloalkyl, or $C_3$-$C_{10}$ halocycloalkyl; or alternatively two $R^2$ together with the carbon atom to which they are attached form a $C_3$-$C_{10}$ cycloalkyl;

$R^3$ is —H or $C_1$-$C_4$ alkyl;

$R^4$ is $C_1$-$C_4$ alkyl, $C_1$-$C_4$ haloalkyl, or $C_3$-$C_6$ cycloalkyl; or alternatively $R^3$ and $R^4$ taken together with their intervening atoms form a 5 to 7 membered heterocycle, wherein said heterocycle is optionally substituted with 1, 2 or 3 substituents independently selected from the group consisting of halo, $C_1$-$C_4$ alkyl, $C_1$-$C_4$ haloalkyl, and $C_1$-$C_4$ alkoxy;

D-E is selected from the group consisting of $CH_2CH_2$, O—$CH_2$, and $CH_2$—O;

$R^5$ and $R^6$ are joined to form an aryl, a 5 or 6 membered heteroaryl or a partially saturated heterocyclic group, fused with the ring containing D-E, in which the ring formed by $R^5$ and $R^6$ may optionally contain 1, 2 or 3 heteroatoms independently selected from nitrogen, oxygen and sulfur and said ring may be optionally substituted with 1, 2 or 3, $R^7$ substituents, where $R^7$ is independently selected from the group consisting of halo, hydroxyl, oxo, $NR^8R^9$, cyano, $C_1$-$C_4$ alkyl, $C_1$-$C_4$ haloalkyl, $C_1$-$C_4$ alkoxy, $C_3$-$C_{10}$ cycloalkyl, and $C_3$-$C_{10}$ halo-cycloalkyl, wherein said $C_1$-$C_4$ alkyl, $C_1$-$C_4$ alkoxy or $C_3$-$C_{10}$ cycloalkyl, are optionally substituted with 1, 2 or 3 substituents independently selected from halo, hydroxyl, $C_1$-$C_4$ haloalkyl and $C_1$-$C_4$ alkoxy; and $R^8$ and $R^9$ are independently selected from H, $C_1$-$C_4$ alkyl, $C_3$-$C_6$ cycloalkyl and $C_1$-$C_4$ alkyl-$C_1$-$C_4$ alkoxy; or $R^8$ and $R^9$ may combine together with the nitrogen atom to which they are attached form a $C_3$-$C_6$ heterocycloalkyl ring said ring may contain one additional heteroatom selected from N and O, wherein said heterocycloalkyl group may be optionally substituted with 1 or 2 $C_1$-$C_4$ alkyl.

Another embodiment of a compound of the present invention is represented by the following structural formula:

(Ia)

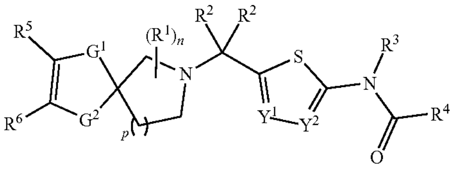

or a pharmaceutically acceptable salt thereof, wherein:

$Y^1$ and $Y^2$ are each $CR^c$ or N, wherein at least one of $Y^1$ or $Y^2$ is N;

$R^c$ is —H, halo, $C_1$-$C_4$ alkyl, or $C_1$-$C_4$ haloalkyl;

p is 1 or 2;

n is 0 or an integer from 1 to 8;

when n is other than 0, $R^1$, for each occurrence, is independently halo, $C_1$-$C_4$ alkyl, $C_1$-$C_4$ haloalkyl, or $C_1$-$C_4$ alkoxy;

$R^2$, for each occurrence, is independently —H, halo, $C_1$-$C_4$ alkyl, $C_1$-$C_4$ haloalkyl, $C_3$-$C_{10}$ cycloalkyl, or $C_3$-$C_{10}$ halocycloalkyl; or alternatively two $R^2$ together with the carbon atom to which they are attached form a $C_3$-$C_{10}$ cycloalkyl;

$R^3$ is —H or $C_1$-$C_4$ alkyl;

$R^4$ is $C_1$-$C_4$ alkyl, $C_1$-$C_4$ haloalkyl, or $C_3$-$C_6$ cycloalkyl; or alternatively $R^3$ and $R^4$ taken together with their intervening atoms form a 5 to 7 membered heterocycle, wherein said heterocycle is optionally substituted with 1, 2 or 3 substituents independently selected from the group consisting of halo, $C_1$-$C_4$ alkyl, $C_1$-$C_4$ haloalkyl, and $C_1$-$C_4$ alkoxy;

$G^1$ is O and $G^2$ is $CH_2$; or $G^1$ is $CH_2$ and $G^2$ is O;

$R^5$ and $R^6$ are joined to form an aryl, a 5 or 6 membered heteroaryl or a partially saturated heterocyclic group, fused with the ring containing $G^1$ and $G^2$, in which the ring formed by $R^5$ and $R^6$ may optionally contain 1, 2 or 3 heteroatoms independently selected from nitrogen, oxygen and sulfur and said ring may be optionally substituted with 1, 2 or 3, $R^7$ substituents, where $R^7$ is independently selected from the group consisting of halo, hydroxyl, oxo, $NR^8R^9$, cyano, $C_1$-$C_4$ alkyl, $C_1$-$C_4$ haloalkyl, $C_1$-$C_4$ alkoxy, $C_3$-$C_{10}$ cycloalkyl, and $C_3$-$C_{10}$ halo-cycloalkyl, wherein said $C_1$-$C_4$ alkyl, $C_1$-$C_4$ alkoxy or $C_3$-$C_{10}$ cycloalkyl, are optionally substituted with 1, 2 or 3 substituents independently selected from halo, hydroxyl, $C_1$-$C_4$ haloalkyl and $C_1$-$C_4$ alkoxy; and $R^8$ and $R^9$ are independently selected from H, $C_1$-$C_4$ alkyl, $C_3$-$C_6$ cycloalkyl and $C_1$-$C_4$ alkyl-$C_1$-$C_4$ alkoxy; or $R^8$ and $R^9$ may combine together with the nitrogen atom to which they are attached form a $C_3$-$C_6$ heterocycloalkyl ring said ring may contain one additional heteroatom selected from N and O, wherein said heterocycloalkyl group may be optionally substituted with 1 or 2 $C_1$-$C_4$ alkyl.

Provided is a pharmaceutical composition comprising at least one compound described herein, or a pharmaceutically acceptable salt thereof, and at least one pharmaceutically acceptable excipient.

Also provided is a method of treating a subject with a disease or condition selected from a neurodegenerative disease, a tauopathy, diabetes, cancer and stress, comprising administering to the subject an effective amount of the compound described herein, or a pharmaceutically acceptable salt thereof, or an effective amount of a pharmaceutical composition comprising at least one compound described herein, or a pharmaceutically acceptable salt thereof, and at least one pharmaceutically acceptable excipient.

Also provided is a method of inhibiting O-GlcNAcase in a subject in need thereof, comprising administering to the subject an effective amount of the compound described herein, or a pharmaceutically acceptable salt thereof, or an effective amount of a pharmaceutical composition comprising at least one compound described herein, or a pharmaceutically acceptable salt thereof, and at least one pharmaceutically acceptable excipient.

Also provided is a method of treating a disease or condition characterized by hyperphosphorylation of tau in the brain, comprising administering to the subject an effective amount of the compound described herein, or a pharmaceutically acceptable salt thereof, or an effective amount of a pharmaceutical composition comprising at least one compound described herein, or a pharmaceutically acceptable salt thereof, and at least one pharmaceutically acceptable excipient. In one embodiment, the disease or condition characterized by hyperphosphorylation of tau in the brain is Alzheimer's disease.

DETAILED DESCRIPTION

Described herein are compounds that are useful treating various diseases, disorders and medical conditions, including but not limited to those associated with proteins that are modified by O-GlcNAcase.

In a first embodiment, a compound of the present invention is represented by structural formula (I):

(I)

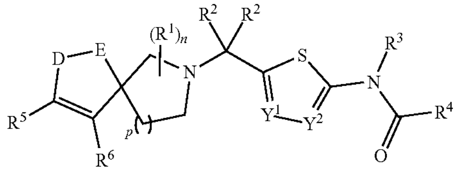

or a pharmaceutically acceptable salt thereof, wherein:

$Y^1$ and $Y^2$ are each $CR^c$ or N, wherein at least one of $Y^1$ or $Y^2$ is N;

$R^c$ is —H, halo, $C_1$-$C_4$ alkyl, or $C_1$-$C_4$ haloalkyl;

p is 1 or 2;

n is 0 or an integer from 1 to 8;

when n is other than 0, $R^1$, for each occurrence, is independently halo, $C_1$-$C_4$ alkyl, $C_1$-$C_4$ haloalkyl, or $C_1$-$C_4$ alkoxy;

$R^2$, for each occurrence, is independently —H, halo, $C_1$-$C_4$ alkyl, $C_1$-$C_4$ haloalkyl, $C_3$-$C_{10}$ cycloalkyl, or $C_3$-$C_{10}$ halocycloalkyl; or alternatively two $R^2$ together with the carbon atom to which they are attached form a $C_3$-$C_{10}$ cycloalkyl;

$R^3$ is —H or $C_1$-$C_4$ alkyl;

$R^4$ is $C_1$-$C_4$ alkyl, $C_1$-$C_4$ haloalkyl, or $C_3$-$C_6$ cycloalkyl; or alternatively $R^3$ and $R^4$ taken together with their intervening atoms form a 5 to 7 membered heterocycle, wherein said heterocycle is optionally substituted with 1, 2 or 3 substituents independently selected from the group consisting of halo, $C_1$-$C_4$ alkyl, $C_1$-$C_4$ haloalkyl, and $C_1$-$C_4$ alkoxy; D-E is selected from the group consisting of $CH_2CH_2$, O—$CH_2$, and $CH_2$—O;

$R^5$ and $R^6$ are joined to form an aryl, a 5 or 6 membered heteroaryl or a partially saturated heterocyclic group, fused with the ring containing D-E, in which the ring formed by $R^5$ and $R^6$ may optionally contain 1, 2 or 3 heteroatoms independently selected from nitrogen, oxygen and sulfur and said ring may be optionally substituted with 1, 2 or 3, $R^7$ substituents, where $R^7$ is independently selected from the group consisting of halo, hydroxyl, oxo, $NR^8R^9$, cyano, $C_1$-$C_4$ alkyl, $C_1$-$C_4$ haloalkyl, $C_1$-$C_4$ alkoxy, $C_3$-$C_{10}$ cycloalkyl, and $C_3$-$C_{10}$ halo-cycloalkyl, wherein said $C_1$-$C_4$ alkyl, $C_1$-$C_4$ alkoxy or $C_3$-$C_{10}$ cycloalkyl, are optionally substituted with 1, 2 or 3 substituents independently selected from halo, hydroxyl, $C_1$-$C_4$ haloalkyl and $C_1$-$C_4$ alkoxy; and $R^8$ and $R^9$ are independently selected from H, $C_1$-$C_4$ alkyl, $C_3$-$C_6$ cycloalkyl and $C_1$-$C_4$ alkyl-$C_1$-$C_4$ alkoxy; or $R^8$ and $R^9$ may combine together with the nitrogen atom to which they are attached form a $C_3$-$C_6$ heterocycloalkyl ring said ring may contain one additional heteroatom selected from N and O, wherein said heterocycloalkyl group may be optionally substituted with 1 or 2 $C_1$-$C_4$ alkyl.

In a second embodiment, a compound of the present invention is represented by structural formula (II):

(II)

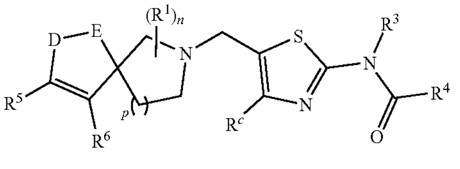

or a pharmaceutically acceptable salt thereof.

In a third embodiment, a compound of the present invention in accordance to the first, or second embodiments or a pharmaceutically acceptable salt thereof, wherein:

The bicyclic ring formed by D-E, $R^5$ and $R^6$ is selected from the group consisting of:

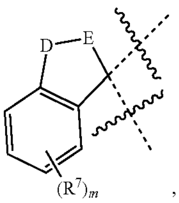 , 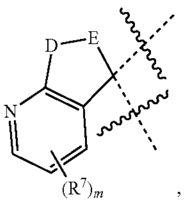 ,

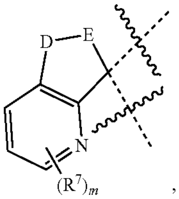 , 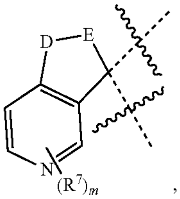 ,

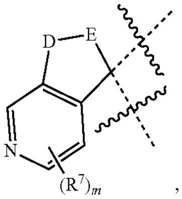 , 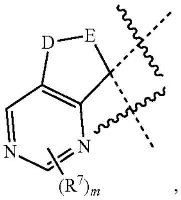 ,

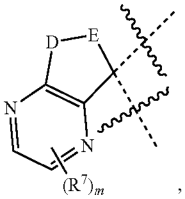 , 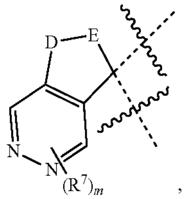 ,

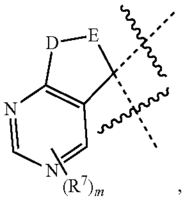 , 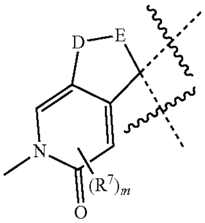 and

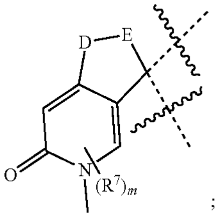 ;

where D-E is selected from the group consisting of $CH_2CH_2$, O—$CH_2$, and $CH_2$—O;

m is 0, 1 or 2;

$R^7$ is independently selected from the group consisting of halo, hydroxyl, $NR^8R^9$, $C_1$-$C_4$ alkyl, $C_1$-$C_4$ haloalkyl, $C_1$-$C_4$ alkoxy, $C_3$-$C_{10}$ cycloalkyl, and $C_3$-$C_{10}$ halocycloalkyl, wherein said $C_1$-$C_4$ alkyl, $C_1$-$C_4$ alkoxy or $C_3$-$C_{10}$ cycloalkyl, are optionally substituted with 1, 2 or 3 substituents independently selected from halo, hydroxyl, $C_1$-$C_4$ haloalkyl and $C_1$-$C_4$ alkoxy; and $R^8$ and $R^9$ are independently selected from H, $C_1$-$C_4$ alkyl, $C_3$-$C_6$ cycloalkyl and $C_1$-$C_4$ alkyl-$C_1$-$C_4$ alkoxy; or $R^8$ and $R^9$ may combine together with the nitrogen atom to which they are attached form azetidine, piperazine, morpholine or piperidine, said piperazine, morpholine or piperidine may be optionally substituted with 1 or 2 $C_1$-$C_4$ alkyl.

In a fourth embodiment, in a compound of the invention in accordance to the first, second or third embodiments or a pharmaceutically acceptable salt thereof, wherein:

$Y^1$ is $CR^c$ and $Y^2$ is N;

$R^c$ is halo, $C_1$-$C_4$ alkyl, or $C_1$-$C_4$ haloalkyl;

D-E is $CH_2$—O;

m is 0, 1 or 2;

n is 0 or 1; and $R^1$ is H, halo or $C_1$-$C_4$ alkyl.

In a fifth embodiment, in a compound of the invention in accordance to the first, second or third embodiments or a pharmaceutically acceptable salt thereof, wherein:

$Y^1$ is $CR^c$ and $Y^2$ is N;

$R^c$ is halo, $C_1$-$C_4$ alkyl, or $C_1$-$C_4$ haloalkyl;

D-E is O—$CH_2$;

m is 0, 1 or 2;

n is 0 or 1; and $R^1$ is H, halo or $C_1$-$C_4$ alkyl.

In a sixth embodiment, in a compound of the invention in accordance to the first, second, third or fourth embodiments wherein the bicyclic ring formed by D-E, $R^5$ and $R^6$ is selected from the group consisting of:

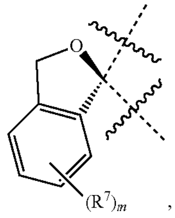 , 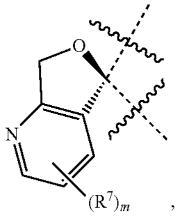 ,

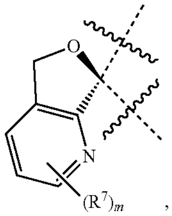 , 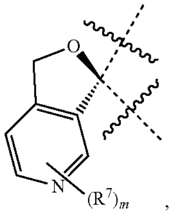 ,

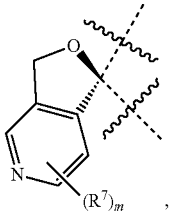 , 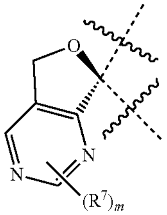

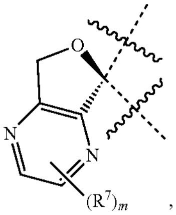 , 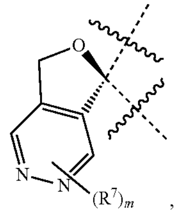 ,

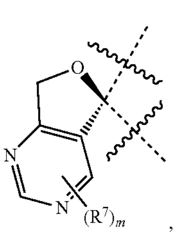 , 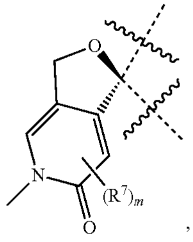 , and

-continued

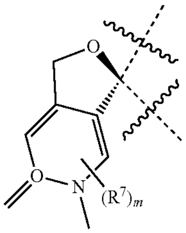 ;

or a pharmaceutically acceptable salt thereof.

In a seventh embodiment, in a compound of the invention in accordance to the first, second, third or fourth embodiments wherein the bicyclic ring formed by D-E, $R^5$ and $R^6$ is selected from the group consisting of:

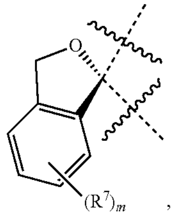 , 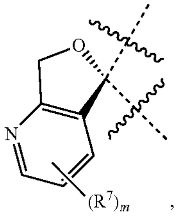 ,

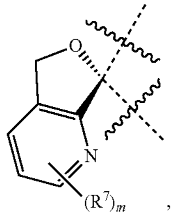 , 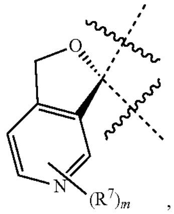 ,

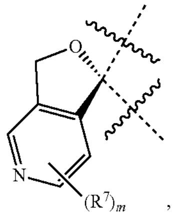 , 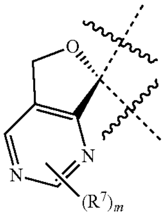

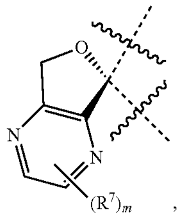 , 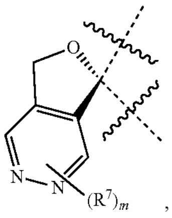 ,

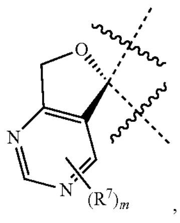 , 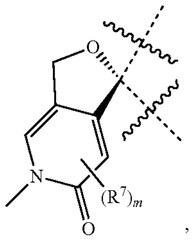 , and

-continued

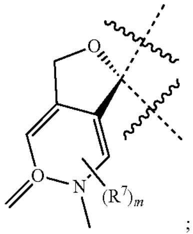

;

or a pharmaceutically acceptable salt thereof.

In an eighth embodiment, a compound according to embodiment one, two, three, four or six wherein the compound is represented by the following structural formula:

(IIb)

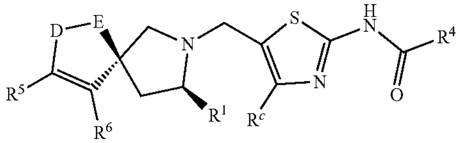

$R^c$ is halo;

$R^1$ is $CH_3$ or $CH_2CH_3$; and the bicyclic ring formed by D-E, $R^5$ and $R^6$ is selected from the group consisting of:

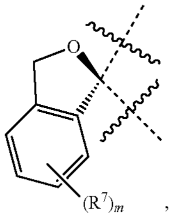
,
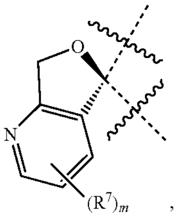
,
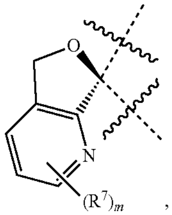
,
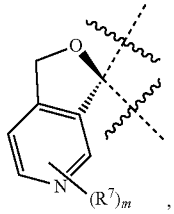
,
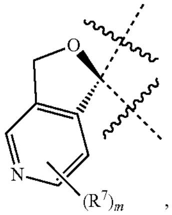
,
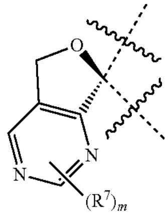
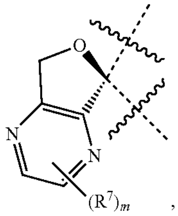
,
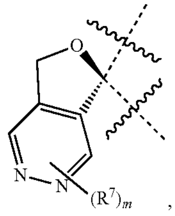
, -continued

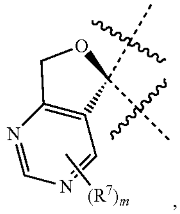
,
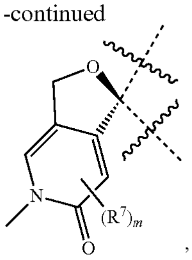
, and
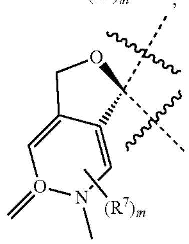
;

or a pharmaceutically acceptable salt thereof.

In a ninth embodiment, a compound according to embodiment one, two, three, four or six wherein the compound is represented by the following structural formula:

(IIc)

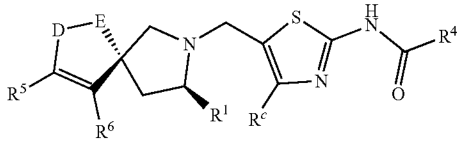

$R^c$ is halo;

$R^1$ is $CH_3$ or $CH_2CH_3$; and the bicyclic ring formed by D-E, $R^5$ and $R^6$ is selected from the group consisting of:

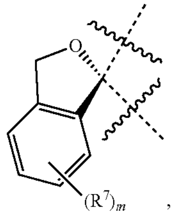
,
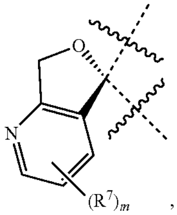
,
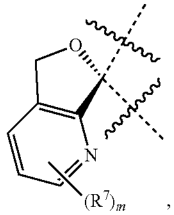
,
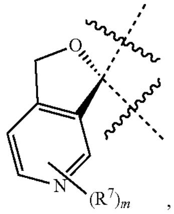
,
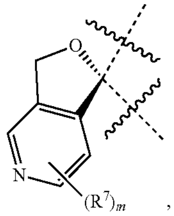
,
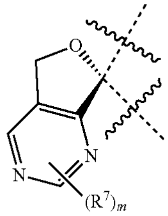

-continued

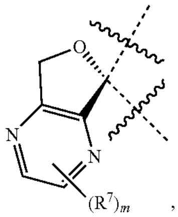
,
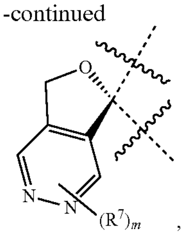
,
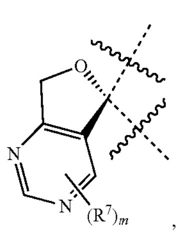
,
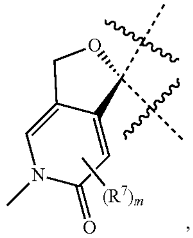
, and
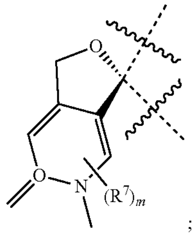
;

or a pharmaceutically acceptable salt thereof.

In a tenth embodiment, a compound according to embodiment one, two, three, four, seven or nine wherein the compound is represented by the following structural formula:

(III)

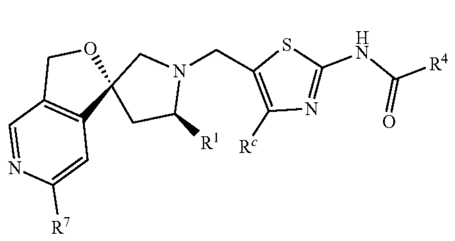

$R^c$ is halo;

$R^1$ is CHs or $CH_2CH_3$;

or a pharmaceutically acceptable salt thereof.

In an eleventh embodiment, a compound of the present invention is represented by structural formula (Ia):

(Ia)

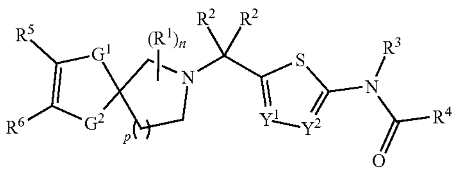

$Y^1$ and $Y^2$ are each CRE or N, wherein at least one of $Y^1$ or $Y^2$ is N;

$R^c$ is —H, halo, $C_1$-$C_4$ alkyl, or $C_1$-$C_4$ haloalkyl;

p is 1 or 2;

n is 0 or an integer from 1 to 8;

when n is other than 0, $R^1$, for each occurrence, is independently halo, $C_1$-$C_4$ alkyl, $C_1$-$C_4$ haloalkyl, or $C_1$-$C_4$ alkoxy;

$R^2$, for each occurrence, is independently —H, halo, $C_1$-$C_4$ alkyl, $C_1$-$C_4$ haloalkyl, $C_3$-$C_{10}$ cycloalkyl, or $C_3$-$C_{10}$ halocycloalkyl; or alternatively two $R^2$ together with the carbon atom to which they are attached form a $C_3$-$C_{10}$ cycloalkyl;

$R^3$ is —H or $C_1$-$C_4$ alkyl;

$R^4$ is $C_1$-$C_4$ alkyl, $C_1$-$C_4$ haloalkyl, or $C_3$-$C_6$ cycloalkyl; or alternatively $R^3$ and $R^4$ taken together with their intervening atoms form a 5 to 7 membered heterocycle, wherein said heterocycle is optionally substituted with 1, 2 or 3 substituents independently selected from the group consisting of halo, $C_1$-$C_4$ alkyl, $C_1$-$C_4$ haloalkyl, and $C_1$-$C_4$ alkoxy;

$G^1$ is O and $G^2$ is $CH_2$; or $G^1$ is $CH_2$ and $G^2$ is O;

$R^5$ and $R^6$ are joined to form an aryl, a 5 or 6 membered heteroaryl or partially saturated heterocyclic group, fused with the ring containing $G^1$ and $G^2$, in which the ring formed by $R^5$ and $R^6$ may optionally contain 1, 2 or 3 heteroatoms independently selected from nitrogen, oxygen and sulfur and said ring may be optionally substituted with 1, 2 or 3, $R^7$ substituents, where $R^7$ is independently selected from the group consisting of halo, hydroxyl, oxo, $NR^8R^9$, cyano, $C_1$-$C_4$ alkyl, $C_1$-$C_4$ haloalkyl, $C_1$-$C_4$ alkoxy, $C_3$-$C_{10}$ cycloalkyl, and $C_3$-$C_{10}$ halo-cycloalkyl, wherein said $C_1$-$C_4$ alkyl, $C_1$-$C_4$ alkoxy or $C_3$-$C_{10}$ cycloalkyl, are optionally substituted with 1, 2 or 3 substituents independently selected from halo, hydroxyl, $C_1$-$C_4$ haloalkyl and $C_1$-$C_4$ alkoxy; and $R^8$ and $R^9$ are independently selected from H, $C_1$-$C_4$ alkyl, $C_3$-$C_6$ cycloalkyl and $C_1$-$C_4$ alkyl-$C_1$-$C_4$ alkoxy; or $R^8$ and $R^9$ may combine together with the nitrogen atom to which they are attached form a $C_3$-$C_6$ heterocycloalkyl ring said ring may contain one additional heteroatom selected from N and O, wherein said heterocycloalkyl group may be optionally substituted with 1 or 2 $C_1$-$C_4$ alkyl In a twelfth embodiment, a compound of embodiment ten is represented by structural formula (IIa):

(IIa)

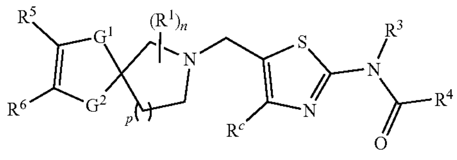

or a pharmaceutically acceptable salt thereof.

In a thirteenth embodiment, a compound of the present invention in accordance to embodiment eleven or twelve or a pharmaceutically acceptable salt thereof, wherein:

The bicyclic ring formed by $G^1$ and $G^2$, $R^5$ and $R^6$ is selected from the group consisting of:

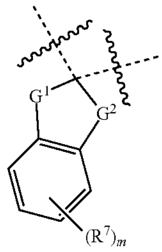 , 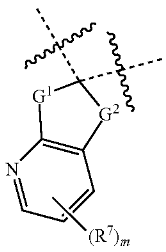 ,

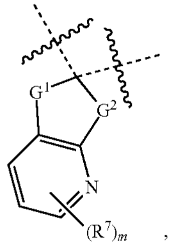 , 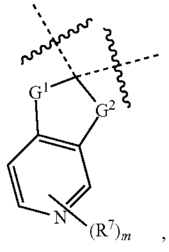 ,

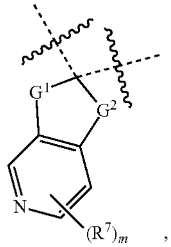 , 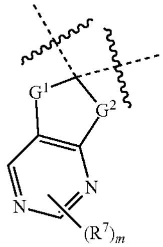 ,

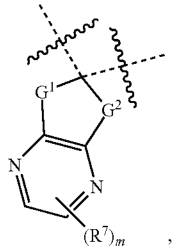 , 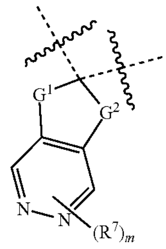 ,

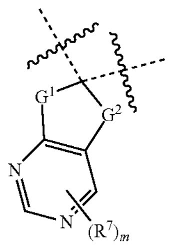 , 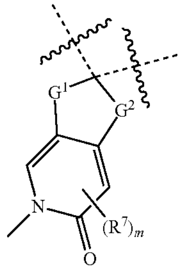 , and

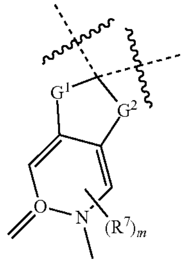 ;

m is 0, 1 or 2;

$R^7$ is independently selected from the group consisting of halo, hydroxyl, $NR^8R^9$, $C_1$-$C_4$ alkyl, $C_1$-$C_4$ haloalkyl, $C_1$-$C_4$ alkoxy, $C_3$-$C_{10}$ cycloalkyl, and $C_3$-$C_{10}$ halocycloalkyl, wherein said $C_1$-$C_4$ alkyl, $C_1$-$C_4$ alkoxy or $C_3$-$C_{10}$ cycloalkyl, are optionally substituted with 1, 2 or 3 substituents independently selected from halo, hydroxyl, $C_1$-$C_4$ haloalkyl and $C_1$-$C_4$ alkoxy; and $R^8$ and $R^9$ are independently selected from H, $C_1$-$C_4$ alkyl, $C_3$-$C_6$ cycloalkyl and $C_1$-$C_4$ alkyl-$C_1$-$C_4$ alkoxy; or $R^8$ and $R^9$ may combine together with the nitrogen atom to which they are attached form azetidine, piperazine, morpholine or piperidine, said piperazine, morpholine or piperidine may be optionally substituted with 1 or 2 $C_1$-$C_4$ alkyl.

In a fourteenth embodiment, a compound of the present invention in accordance to embodiment eleven, twelve or thirteen or a pharmaceutically acceptable salt thereof, wherein:

$Y^1$ is $CR^c$ and $Y^2$ is N;

$R^c$ is halo, $C_1$-$C_4$ alkyl, or $C_1$-$C_4$ haloalkyl;

$G^1$ is O and $G^2$ is $CH_2$;

m is 0, 1 or 2;

n is 0 or 1; and $R^1$ is H, halo or $C_1$-$C_4$ alkyl.

In a fifteenth embodiment, a compound of the present invention in accordance to embodiment eleven, twelve or thirteen or a pharmaceutically acceptable salt thereof, wherein:

$Y^1$ is $CR^c$ and $Y^2$ is N;

$R^c$ is halo, $C_1$-$C_4$ alkyl, or $C_1$-$C_4$ haloalkyl;

$G^1$ is $CH_2$ and $G^2$ is $CH_2$;

m is 0, 1 or 2;

n is 0 or 1; and $R^1$ is H, halo or $C_1$-$C_4$ alkyl.

In a sixteenth embodiment, a compound of the present invention in accordance to embodiment eleven, twelve or thirteen or a pharmaceutically acceptable salt thereof, wherein:

$Y^1$ is $CR^c$ and $Y^2$ is N;

$R^c$ is halo, $C_1$-$C_4$ alkyl, or $C_1$-$C_4$ haloalkyl;

$G^1$ is $CH_2$ and $G^2$ is O;

m is 0, 1 or 2;

n is 0 or 1; and $R^1$ is H, halo or $C_1$-$C_4$ alkyl.

In a seventeenth embodiment, in a compound of the invention in accordance to embodiments eleven, twelve, thirteen or fourteen wherein the bicyclic ring formed by $G^1$ and $G^2$, $R^5$ and $R^6$ is selected from the group consisting of:

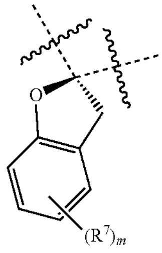 , 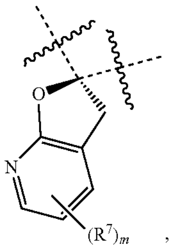 ,

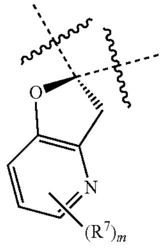 , 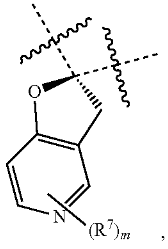 ,

-continued

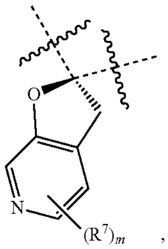 , 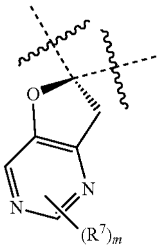 ,

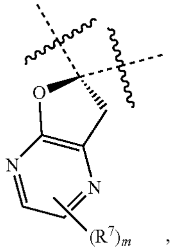 , 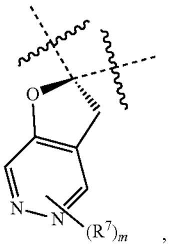 ,

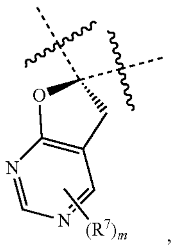 , 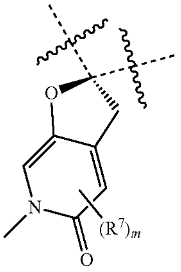 , and

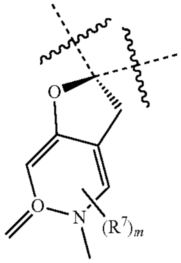 ;

or a pharmaceutically acceptable salt thereof.

In an eighteenth embodiment, in a compound of the invention in accordance to embodiments eleven, twelve, thirteen or fourteen wherein the bicyclic ring formed by $G^1$ and $G^2$, $R^5$ and $R^6$ is selected from the group consisting of:

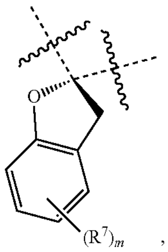 , 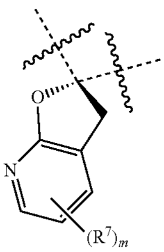 ,

-continued

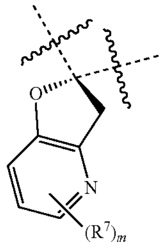 , 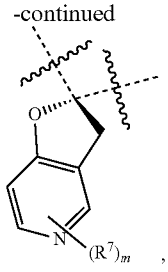 ,

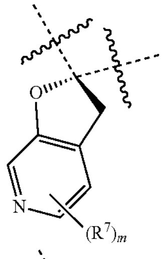 , 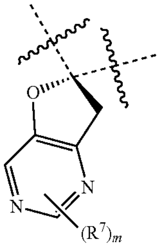 ,

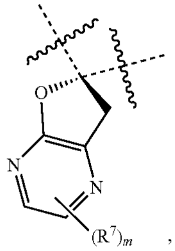 , 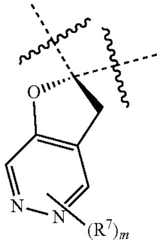 ,

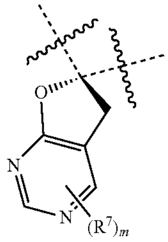 , 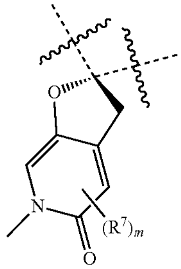 , and

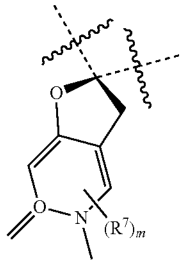 ;

or a pharmaceutically acceptable salt thereof.

In a nineteenth embodiment, in a compound of the invention in accordance to embodiment eleven, twelve, thirteen or fourteen wherein the compound is represented by the following structural formula:

(IId)

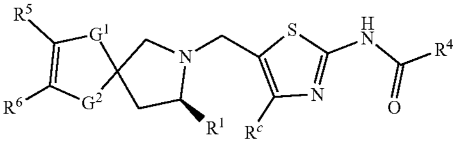

$R^c$ is halo;

$R^1$ is $CH_3$ or $CH_2CH_3$; and the bicyclic ring formed by $G^1$, $G^2$, $R^5$ and $R^6$ is selected from the group consisting of:

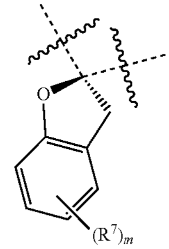 , 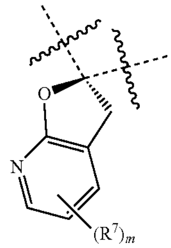 ,

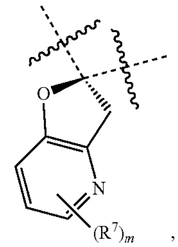 , 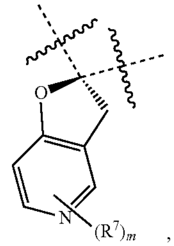 ,

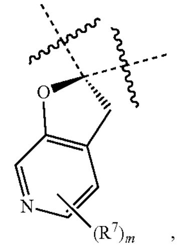 , 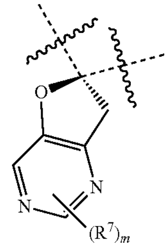 ,

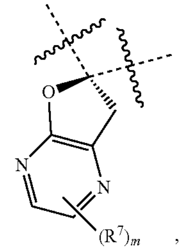 , 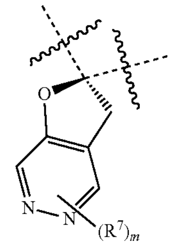 ,

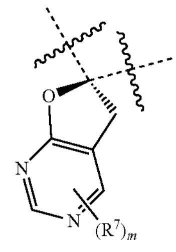 , 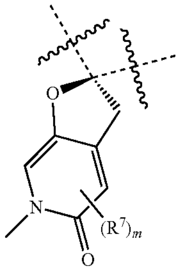 , and

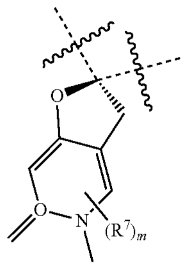 ;

or a pharmaceutically acceptable salt thereof.

In a twentieth embodiment, in a compound of the invention in accordance to embodiment eleven, twelve, thirteen or fourteen wherein the compound is represented by the following structural formula:

(IIe)

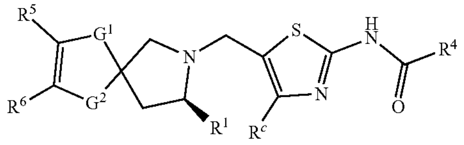

$R^c$ is halo;

$R^1$ is $CH_3$ or $CH_2CH_3$; and the bicyclic ring formed by $G^1$, $G^2$, $R^5$ and $R^6$ is selected from the group consisting of:

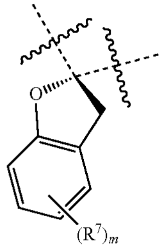 , 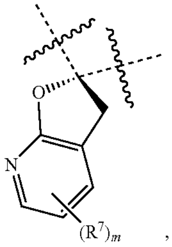 ,

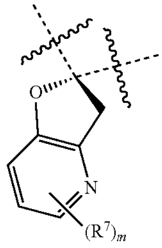 , 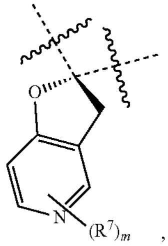 ,

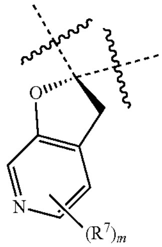 , 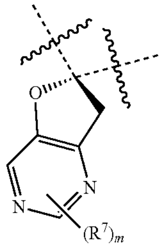 ,

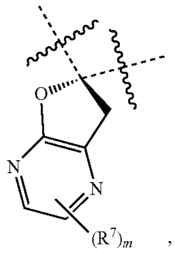 , 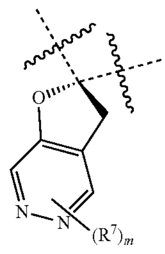 ,

-continued

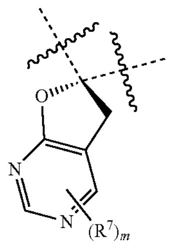
,
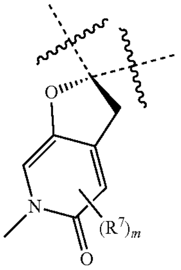
, and

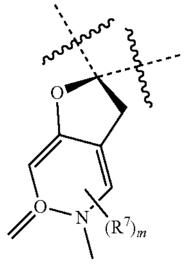
;

or a pharmaceutically acceptable salt thereof.

In a twenty-first embodiment, a compound of embodiment eleven, twelfth, thirteen or fourteen of formula (IIIa):

(IIIa)

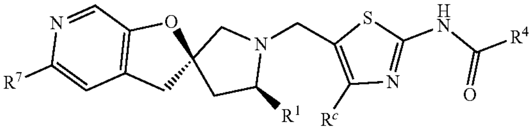

$R^c$ is halo; and $R^1$ is $CH_3$ or $CH_2CH_3$;

or a pharmaceutically acceptable salt thereof.

In a twenty-second embodiment, a compound of the invention in accordance to any of the preceding embodiments, or a pharmaceutically acceptable salt thereof, wherein $R^1$ is $CH_3$ or $CH_2CH_3$; $R^c$ is F, or Cl; $R^3$ is —H; $R^4$ is $CH_3$, $CH_2CH_3$ or cyclopropyl; and wherein the remaining variables are as defined in the first, second, third, or fourth embodiments, or the seventh embodiment.

In another embodiment $R^7$ is selected from the group consisting of

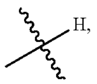
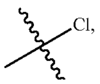
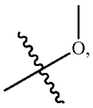
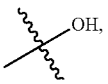

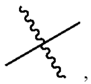
,
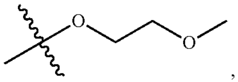
,
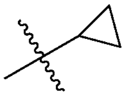
,

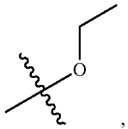
,
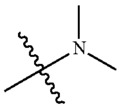
,
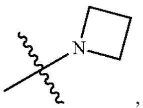
,

-continued

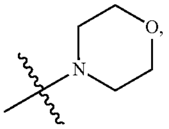
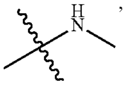
,
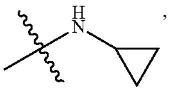
,

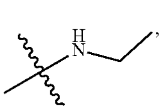
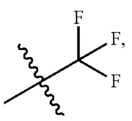
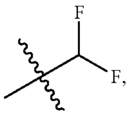

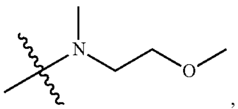
,
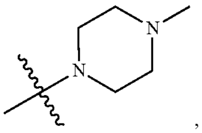
,

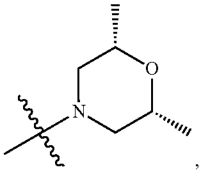
, or
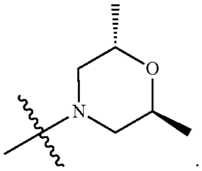
.

In one embodiment, a compound of the invention, such as a compound in accordance with any one of the previous embodiments, is selected from the following:

N-(4-Fluoro-5-(((2R,5'S)-5'-methyl-3H-spiro[benzofuran-2,3'-pyrrolidin]-1'-yl)methyl)thiazol-2-yl)acetamide;

N-(5-(((2R,5'S)-5'-Methyl-3H-spiro[benzofuran-2,3'-pyrrolidin]-1'-yl)methyl)thiazol-2-yl)acetamide;

N-(5-((3H-Spiro[benzofuran-2,3'-pyrrolidin]-1'-yl)methyl)thiazol-2-yl)acetamide;

N-(4-Fluoro-5-((7-methoxy-3H-spiro[benzofuran-2,3'-pyrrolidin]-1'-yl)methyl)thiazol-2-yl)acetamide;

N-(5-((5-Chloro-3H-spiro[benzofuran-2,3'-pyrrolidin]-1'-yl)methyl)thiazol-2-yl)acetamide;

N-(5-((5-Chloro-3H-spiro[benzofuran-2,3'-pyrrolidin]-1'-yl)methyl)-4-fluorothiazol-2-yl)acetamide;

N-(5-((6-Chloro-3H-spiro[furo[3,2-c]pyridine-2,3'-pyrrolidin]-1'-yl)methyl)-4-fluorothiazol-2-yl)acetamide;

N-(5-((6-Chloro-3H-spiro[furo[3,2-c]pyridine-2,3'-pyrrolidin]-1'-yl)methyl)thiazol-2-yl)acetamide;

N-(4-Fluoro-5-(((2R,5'S)-5'-methyl-3H-spiro[furo[2,3-c]pyridine-2,3'-pyrrolidin]-1'-yl)methyl)thiazol-2-yl)acetamide;

N-(5-(((2R,5'S)-5-Chloro-5'-methyl-3H-spiro[furo[2,3-c]pyridine-2,3'-pyrrolidin]-1'-yl)methyl)-4-fluorothiazol-2-yl)acetamide;

N-(5-(((2R,5'S)-5-Chloro-5'-methyl-3H-spiro[furo[2,3-c]pyridine-2,3'-pyrrolidin]-1'-yl)methyl)thiazol-2-yl)acetamide;

N-(5-((3H-Spiro[furo[3,2-c]pyridine-2,3'-pyrrolidin]-1'-yl)methyl)-4-fluorothiazol-2-yl)acetamide;

N-(5-((3H-Spiro[furo[3,2-c]pyridine-2,3'-pyrrolidin]-1'-yl)methyl)thiazol-2-yl)acetamide;

N-(5-((3H-Spiro[furo[2,3-b]pyridine-2,3'-pyrrolidin]-1'-yl)methyl)thiazol-2-yl)acetamide;

N-(5-((3H-Spiro[furo[2,3-b]pyridine-2,3'-pyrrolidin]-1'-yl)methyl)-4-fluorothiazol-2-yl)acetamide;

N-(4-Fluoro-5-(((2R,5'S)-5-methoxy-5'-methyl-3H-spiro[furo[2,3-c]pyridine-2,3'-pyrrolidin]-1'-yl)methyl)thiazol-2-yl)acetamide;

N-(5-(((2R,5'S)-5-Methoxy-5'-methyl-3H-spiro[furo[2,3-c]pyridine-2,3'-pyrrolidin]-1'-yl)methyl)thiazol-2-yl)acetamide;

N-(4-Fluoro-5-(((2R,5'S)-4-methoxy-5'-methyl-3H-spiro[furo[3,2-c]pyridine-2,3'-pyrrolidin]-1'-yl)methyl)thiazol-2-yl)acetamide;

N-(4-Fluoro-5-(((2S,5'S)-5'-methyl-3H-spiro[furo[3,2-b]pyridine-2,3'-pyrrolidin]-1'-yl)methyl)thiazol-2-yl)acetamide;

N-(4-Fluoro-5-(((2S,5'S)-5-methoxy-5'-methyl-3H-spiro[furo[3,2-b]pyridine-2,3'-pyrrolidin]-1'-yl)methyl)thiazol-2-yl)acetamide;

N-(4-Fluoro-5-(((2R,5'S)-5'-methyl-5-(trifluoromethyl)-3H-spiro[furo[2,3-c]pyridine-2,3'-pyrrolidin]-1'-yl)methyl)thiazol-2-yl)acetamide;

N-(5-(((2R,5'S)-5'-Methyl-5-(trifluoromethyl)-3H-spiro[furo[2,3-c]pyridine-2,3'-pyrrolidin]-1'-yl)methyl)thiazol-2-yl)acetamide;

N-(5-(((2R,5'S)-5,5'-Dimethyl-3H-spiro[furo[2,3-c]pyridine-2,3'-pyrrolidin]-1'-yl)methyl)-4-fluorothiazol-2-yl)acetamide;

N-(5-(((2R,5'S)-5-Cyclopropyl-5'-methyl-3H-spiro[furo[2,3-c]pyridine-2,3'-pyrrolidin]-1'-yl)methyl)-4-fluorothiazol-2-yl)acetamide;

N-(5-(((2R,5'S)-5-Cyclopropyl-5'-methyl-3H-spiro[furo[2,3-c]pyridine-2,3'-pyrrolidin]-1'-yl)methyl)thiazol-2-yl)acetamide;

N-(5-(((2R,5'S)-5-(Difluoromethyl)-5'-methyl-3H-spiro[furo[2,3-c]pyridine-2,3'-pyrrolidin]-1'-yl)methyl)-4-fluorothiazol-2-yl)acetamide;

N-(5-(((2R,5'S)-5-(Difluoromethyl)-5'-methyl-3H-spiro[furo[2,3-c]pyridine-2,3'-pyrrolidin]-1'-yl)methyl)thiazol-2-yl)acetamide;

N-(5-(((2R,5'S)-5-(Dimethylamino)-5'-methyl-3H-spiro[furo[2,3-c]pyridine-2,3'-pyrrolidin]-1'-yl)methyl)-4-fluorothiazol-2-yl)acetamide;

N-(4-Fluoro-5-(((2R,5'S)-5'-methyl-5-(methylamino)-3H-spiro[furo[2,3-c]pyridine-2,3'-pyrrolidin]-1'-yl)methyl)thiazol-2-yl)acetamide;

N-(4-Fluoro-5-(((2R,5'S)-5-(isopropylamino)-5'-methyl-3H-spiro[furo[2,3-c]pyridine-2,3'-pyrrolidin]-1'-yl)methyl)thiazol-2-yl)acetamide;

N-(5-(((2R,5'S)-5-(Cyclopropylamino)-5'-methyl-3H-spiro[furo[2,3-c]pyridine-2,3'-pyrrolidin]-1'-yl)methyl)-4-fluorothiazol-2-yl)acetamide;

N-(5-(((2R,5'S)-5-((2-Methoxyethyl)(methyl)amino)-5'-methyl-3H-spiro[furo[2,3-c]pyridine-2,3'-pyrrolidin]-1'-yl)methyl)thiazol-2-yl)acetamide;

N-(4-Fluoro-5-(((2R,5'S)-5-((2-methoxyethyl)(methyl)amino)-5'-methyl-3H-spiro[furo[2,3-c]pyridine-2,3'-pyrrolidin]-11-yl)methyl)thiazol-2-yl)acetamide;

N-(5-(((2R,5'S)-5-(Azetidin-1-yl)-5'-methyl-3H-spiro[furo[2,3-c]pyridine-2,3'-pyrrolidin]-1'-yl)methyl)-4-fluorothiazol-2-yl)acetamide;

N-(5-(((2R,5'S)-5-(Azetidin-1-yl)-5'-methyl-3H-spiro[furo[2,3-c]pyridine-2,3'-pyrrolidin]-1'-yl)methyl)thiazol-2-yl)acetamide;

N-(4-Fluoro-5-(((2R,5'S)-5'-methyl-5-morpholino-3H-spiro[furo[2,3-c]pyridine-2,3'-pyrrolidin]-1'-yl)methyl)thiazol-2-yl)acetamide;

N-(5-(((2R,5'S)-5'-Methyl-5-morpholino-3H-spiro[furo[2,3-c]pyridine-2,3'-pyrrolidin]-1'-yl)methyl)thiazol-2-yl)acetamide;

N-(5-(((2R,5'S)-5-((2R,6S)-2,6-Dimethylmorpholino)-5'-methyl-3H-spiro[furo[2,3-c]pyridine-2,3'-pyrrolidin]-1'-yl)methyl)thiazol-2-yl)acetamide;

N-(5-(((2R,5'S)-5-((2R,6S)-2,6-Dimethylmorpholino)-5'-methyl-3H-spiro[furo[2,3-c]pyridine-2,3'-pyrrolidin]-1'-yl)methyl)-4-fluorothiazol-2-yl)acetamide;

N-(5-(((2R,5'S)-5-((2R,6R)-2,6-Dimethylmorpholino)-5'-methyl-3H-spiro[furo[2,3-c]pyridine-2,3'-pyrrolidin]-1'-yl)methyl)thiazol-2-yl)acetamide;

N-(5-(((2R,5'S)-5-((2R,6R)-2,6-Dimethylmorpholino)-5'-methyl-3H-spiro[furo[2,3-c]pyridine-2,3'-pyrrolidin]-1'-yl)methyl)-4-fluorothiazol-2-yl)acetamide;

N-(5-(((2R,5'S)-5-((2S,6S)-2,6-Dimethylmorpholino)-5'-methyl-3H-spiro[furo[2,3-c]pyridine-2,3'-pyrrolidin]-1'-yl)methyl)thiazol-2-yl)acetamide;

N-(5-(((2R,5'S)-5-((2S,6S)-2,6-Dimethylmorpholino)-5'-methyl-3H-spiro[furo[2,3-c]pyridine-2,3'-pyrrolidin]-1'-yl)methyl)-4-fluorothiazol-2-yl)acetamide;

N-(5-(((2R,5'S)-5'-Methyl-5-(4-methylpiperazin-1-yl)-3H-spiro[furo[2,3-c]pyridine-2,3'-pyrrolidin]-1'-yl)methyl)thiazol-2-yl)acetamide;

N-(4-Fluoro-5-(((2R,5'S)-5'-methyl-5-(4-methylpiperazin-1-yl)-3H-spiro[furo[2,3-c]pyridine-2,3'-pyrrolidin]-1'-yl)methyl)thiazol-2-yl)acetamide;

N-(5-(((2R,5'S)-5-Ethoxy-5'-methyl-3H-spiro[furo[2,3-c]pyridine-2,3'-pyrrolidin]-1'-yl)methyl)-4-fluorothiazol-2-yl)acetamide;

N-(4-Fluoro-5-(((2R,5'S)-5-(2-methoxyethoxy)-5'-methyl-3H-spiro[furo[2,3-c]pyridine-2,3'-pyrrolidin]-1'-yl)methyl)thiazol-2-yl)acetamide;

N-(5-(((2R,5'S)-5',6-Dimethyl-5-oxo-5,6-dihydro-3H-spiro[furo[2,3-c]pyridine-2,3'-pyrrolidin]-1'-yl)methyl)-4-fluorothiazol-2-yl)acetamide;

N-(4-Fluoro-5-(((2R,5'S)-5'-methyl-5-oxo-5,6-dihydro-3H-spiro[furo[2,3-c]pyridine-2,3'-pyrrolidin]-1'-yl)methyl)thiazol-2-yl)acetamide;

N-(4-Fluoro-5-(((5'S)-2-methoxy-5'-methyl-7H-spiro[furo[2,3-b]pyrazine-6,3'-pyrrolidin]-1'-yl)methyl)thiazol-2-yl)acetamide;

N-(5-((2,3-Dihydrospiro[indene-1,3'-piperidin]-1'-yl)methyl)thiazol-2-yl)acetamide;

N-(5-((2H-Spiro[benzofuran-3,3'-piperidin]-1'-yl)methyl)-4-fluorothiazol-2-yl)acetamide;

N-(5-((3H-Spiro[isobenzofuran-1,3'-piperidin]-1'-yl)methyl)thiazol-2-yl)acetamide;

N-(5-((3H-Spiro[isobenzofuran-1,3'-piperidin]-1'-yl)methyl)-4-fluorothiazol-2-yl)acetamide;

N-(5-((3H-Spiro[isobenzofuran-1,3'-piperidin]-1'-yl)methyl)-4-fluorothiazol-2-yl)acetamide;

N-(5-((3H-Spiro[isobenzofuran-1,3'-pyrrolidin]-1'-yl)methyl)thiazol-2-yl)acetamide;

N-(4-Fluoro-5-(((5'S)-5'-methyl-3H-spiro[isobenzofuran-1,3'-pyrrolidin]-1'-yl)methyl)thiazol-2-yl)acetamide;

N-(5-(((5'S)-5'-Methyl-3H-spiro[isobenzofuran-1,3'-pyrrolidin]-1'-yl)methyl)thiazol-2-yl)acetamide;

N-(5-((6'-Methyl-3H-spiro[isobenzofuran-1,3'-piperidin]-1'-yl)methyl)thiazol-2-yl)acetamide;

N-(5-((5H-Spiro[furo[3,4-b]pyridine-7,3'-piperidin]-1'-yl)methyl)-4-fluorothiazol-2-yl)acetamide;

N-(5-(((5'S)-5'-Methyl-5H-spiro[furo[3,4-b]pyridine-7,3'-pyrrolidin]-1'-yl)methyl)thiazol-2-yl)acetamide;

N-(4-Fluoro-5-(((5'S)-5'-methyl-5H-spiro[furo[3,4-b]pyridine-7,3'-pyrrolidin]-1'-yl)methyl)thiazol-2-yl)acetamide;

N-(4-Fluoro-5-(((1S,5'S)-5'-methyl-3H-spiro[furo[3,4-c]pyridine-1,3'-pyrrolidin]-1'-yl)methyl)thiazol-2-yl)acetamide;

N-(4-fluoro-5-(((1R,5'S)-5'-methyl-3H-spiro[furo[3,4-c]pyridine-1,3'-pyrrolidin]-1'-yl)methyl)thiazol-2-yl)acetamide;

N-(5-(((1S,5'S)-5'-Methyl-3H-spiro[furo[3,4-c]pyridine-1,3'-pyrrolidin]-1'-yl)methyl)thiazol-2-yl)acetamide;

N-(5-(((1R,5'S)-5'-methyl-3H-spiro[furo[3,4-c]pyridine-1,3'-pyrrolidin]-1'-yl)methyl)thiazol-2-yl)acetamide;

N-(5-((3H-Spiro[furo[3,4-c]pyridine-1,3'-pyrrolidin]-1'-yl)methyl)thiazol-2-yl)acetamide;

N-(5-((3H-Spiro[furo[3,4-c]pyridine-1,3'-pyrrolidin]-1'-yl)methyl)-4-fluorothiazol-2-yl)acetamide;

N-(5-((3H-Spiro[furo[3,4-c]pyridine-1,3'-piperidin]-1'-yl)methyl)thiazol-2-yl)acetamide;

N-(5-((3H-Spiro[furo[3,4-c]pyridine-1,3'-piperidin]-1'-yl)methyl)-4-fluorothiazol-2-yl)acetamide;

(R)—N-(5-((3H-Spiro[furo[3,4-c]pyridine-1,3'-piperidin]-1'-yl)methyl)-4-fluorothiazol-2-yl)acetamide;

(S)—N-(5-((3H-spiro[furo[3,4-c]pyridine-1,3'-piperidin]-1'-yl)methyl)-4-fluorothiazol-2-yl)acetamide;

N-(5-(((3S,5'S)-5'-Methyl-1H-spiro[furo[3,4-c]pyridine-3,3'-pyrrolidin]-1'-yl)methyl)thiazol-2-yl)acetamide;

N-(5-(((3R,5'S)-5'-methyl-1H-spiro[furo[3,4-c]pyridine-3,3'-pyrrolidin]-1'-yl)methyl)thiazol-2-yl)acetamide;

N-(4-Fluoro-5-(((3S,5'S)-5'-methyl-1H-spiro[furo[3,4-c]pyridine-3,3'-pyrrolidin]-1'-yl)methyl)thiazol-2-yl)acetamide;

N-(4-fluoro-5-(((3R,5'S)-5'-methyl-1H-spiro[furo[3,4-c]pyridine-3,3'-pyrrolidin]-1'-yl)methyl)thiazol-2-yl)acetamide;

N-(5-((1H-Spiro[furo[3,4-c]pyridine-3,3'-piperidin]-1'-yl)methyl)-4-fluorothiazol-2-yl)acetamide;

N-(5-((1H-Spiro[furo[3,4-c]pyridine-3,3'-piperidin]-1'-yl)methyl)thiazol-2-yl)acetamide;

N-(4-Fluoro-5-(((3S,5'S)-6-methoxy-5'-methyl-1H-spiro[furo[3,4-c]pyridine-3,3'-pyrrolidin]-1'-yl)methyl)thiazol-2-yl)acetamide;

N-(4-fluoro-5-(((3R,5'S)-6-methoxy-5'-methyl-1H-spiro[furo[3,4-c]pyridine-3,3'-pyrrolidin]-1'-yl)methyl)thiazol-2-yl)acetamide;

N-(5-(((3S,5'S)-6-Methoxy-5'-methyl-1H-spiro[furo[3,4-c]pyridine-3,3'-pyrrolidin]-1'-yl)methyl)thiazol-2-yl)acetamide;

N-(5-(((3R,5'S)-6-methoxy-5'-methyl-1H-spiro[furo[3,4-c]pyridine-3,3'-pyrrolidin]-1'-yl)methyl)thiazol-2-yl)acetamide;

N-(4-Fluoro-5-(((5'S)-4-methoxy-5'-methyl-3H-spiro[furo[3,4-c]pyridine-1,3'-pyrrolidin]-1'-yl)methyl)thiazol-2-yl)acetamide;

N-(5-(((5'S)-4-Methoxy-5'-methyl-3H-spiro[furo[3,4-c]pyridine-1,3'-pyrrolidin]-1'-yl)methyl)thiazol-2-yl)acetamide;

N-(4-Fluoro-5-(((5'S)-5'-methyl-7H-spiro[furo[3,4-b]pyridine-5,3'-pyrrolidin]-1'-yl)methyl)thiazol-2-yl)acetamide;

N-(5-(((5'S)-5'-Methyl-7H-spiro[furo[3,4-b]pyridine-5,3'-pyrrolidin]-1'-yl)methyl)thiazol-2-yl)acetamide;

N-(4-Fluoro-5-((4-methoxy-3H-spiro[furo[3,4-c]pyridine-1,3'-piperidin]-1'-yl)methyl)thiazol-2-yl)acetamide;

N-(5-((4-Methoxy-3H-spiro[furo[3,4-c]pyridine-1,3'-piperidin]-1'-yl)methyl)thiazol-2-yl)acetamide;

N-(5-((4-Chloro-3H-spiro[furo[3,4-c]pyridine-1,3'-piperidin]-1'-yl)methyl)-4-fluorothiazol-2-yl)acetamide;

(R)—N-(5-((4-Chloro-3H-spiro[furo[3,4-c]pyridine-1,3'-piperidin]-1'-yl)methyl)-4-fluorothiazol-2-yl)acetamide;

(S)—N-(5-((4-chloro-3H-spiro[furo[3,4-c]pyridine-1,3'-piperidin]-1'-yl)methyl)-4-fluorothiazol-2-yl)acetamide;

rac-N-(5-((4-chloro-3H-spiro[furo[3,4-c]pyridine-1,3'-piperidin]-1'-yl)methyl)-4-fluorothiazol-2-yl)acetamide;

N-(5-((4-Chloro-3H-spiro[furo[3,4-c]pyridine-1,3'-piperidin]-1'-yl)methyl)thiazol-2-yl)acetamide;

N-(4-Fluoro-5-((4-oxo-4,5-dihydro-3H-spiro[furo[3,4-c]pyridine-1,3'-piperidin]-1'-yl)methyl)thiazol-2-yl)acetamide;

N-(5-((4-Oxo-4,5-dihydro-3H-spiro[furo[3,4-c]pyridine-1,3'-piperidin]-1'-yl)methyl)thiazol-2-yl)acetamide;

N-(5-((5H-Spiro[furo[3,4-d]pyrimidine-7,3'-piperidin]-1'-yl)methyl)-4-fluorothiazol-2-yl)acetamide; and N-(5-((5H-Spiro[furo[3,4-d]pyrimidine-7,3'-piperidin]-1'-yl)methyl)thiazol-2-yl)acetamide;

or a pharmaceutically acceptable salt thereof.

In another embodiment, a compound of the invention is selected from the compounds described in the exemplifications herein. Pharmaceutically acceptable salts thereof as well as the neutral forms are included.

As used herein, the term "alkyl" refers to a fully saturated branched or straight chained hydrocarbon moiety. Unless otherwise specified, the alkyl comprises 1 to 12 carbon atoms, preferably 1 to 8 carbon atoms, more preferably 1 to 6 carbon atoms or most preferably 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl and n-hexyl.

As used herein, the term "alkoxy" refers to the group-OR, in which R is an alkyl or a cycloalkyl, as that term is defined above. Non-limiting examples of alkoxy groups include: $—OCH_3$, $—OCH_2CH_3$, $—OCH_2CH_2CH_3$, $—OCH(CH_3)_2$, $—OCH(CH_2)_2$, —O-cyclopropyl, —O-cyclobutyl, —O-cyclopentyl and —O-cyclohexyl.

As used herein, the terms "aryl or $C_{6-10}$aryl" refers to 6- to 10-membered aromatic carbocyclic moieties having a single (e.g., phenyl) or a fused ring system (e.g., naphthalene.). A typical aryl group is phenyl group. Examples of monocyclic aromatic ring systems include, but are not limited to, phenyl, and the like. Examples of bicyclic aromatic ring systems include, but are not limited to, naphthyl, and the like. As used herein, a bicyclic aryl or a bicyclic aromatic ring system includes bicyclic ring systems where a monocyclic aryl fused to another monocyclic aryl, and bicyclic ring systems where a monocyclic aryl is fused to a monocyclic cycloaliphatic ring.

The number of carbon atoms in a group is specified herein by the prefix "$C_{x-xx}$", wherein x and xx are integers. For example, "$C_{1-4}$ alkyl" is an alkyl group which has from 1 to 4 carbon atoms.

As used herein, the term "halogen" or "halo" may be fluoro, chloro, bromo or iodo.

As used herein, the term "haloalkyl" refers to an alkyl, as defined herein, that is substituted by one or more halo groups as defined herein.

As used herein, the terms the term "$C_{3-6}$ cycloalkyl" refers to a carbocyclic ring which is fully saturated (e.g., cyclopropyl, cyclobutyl, cyclopentyl, and cyclohexyl) and the like.

As used herein, the term "3 to 6 membered heterocycle" or "$C_{3-6}$ heterocycle" refers to a monocyclic ring which is fully saturated which has 3 to 6 ring atoms which contains 1 to 2 heteroatoms, independently selected from sulfur, oxygen and/or nitrogen. A typical "$C_{3-6}$ heterocycle" group includes oxtanyl, tetrahydrofuranyl, dihydrofuranyl, 1,4-dioxanyl, morpholinyl, 1,4-dithianyl, piperazinyl, piperidinyl, 1,3-dioxolanyl, pyrrolinyl, pyrrolidinyl, tetrahydropyranyl, oxathiolanyl, dithiolanyl, 1,3-dioxanyl, 1,3-dithianyl, oxathianyl, thiomorpholinyl, thiomorpholinyl 1,1 dioxide, tetrahydro-thiopyran 1,1-dioxide, 1,4-diazepanyl.

The term "partially saturated heterocyclic group" or "fully or partially saturated 4 to 7 membered heterocycle" refers to a nonaromatic ring that is either partially or fully saturated and may exist as a single ring, bicyclic ring (including fused heterocyclic rings) or a spiral ring. Unless specified otherwise, the heterocyclic ring is generally a 4 to 7-membered ring containing 1 to 3 heteroatoms (preferably 1, 2 or 3 heteroatoms) independently selected from sulfur, oxygen and/or nitrogen. A partially saturated heterocyclic ring also includes groups wherein the heterocyclic ring is fused to an aryl or heteroaryl ring (e.g., 2,3-dihydrobenzofuranyl, indolinyl, or 2,3-dihydroindolyl, 2,3-dihydrobenzothiophenyl, 2,3-dihydrobenzothiazolyl, 1,2,3,4-tetrahydroquinolinyl, 1,2,3,4-tetrahydroisoquinolinyl, 5,6,7,8-tetrahydropyrido[3,4-b]pyrazinyl.

As used herein, the terms "heterocyclyl", "heterocyclyl group", "heterocyclic" and "heterocyclic ring" are used interchangeably to refer to a saturated, unsaturated nonaromatic, monocyclic or bicyclic (e.g., fused, spiro or bridged) ring system which has from 3- to 12-ring members, or in particular 3- to 6-ring members or 5 to 7 membered heterocycle, at least one of which is a heteroatom, and up to 4 (e.g., 1, 2, 3 or 4) of which may be heteroatoms, wherein the heteroatoms are independently selected from O, S and N, and wherein C can be oxidized (e.g., C(=O)), N can be oxidized (e.g., N(O)) or quaternized (e.g. $N^+$), and S can be optionally oxidized to sulfoxide and sulfone. Examples of monocyclic heterocyclic ring systems include aziridinyl, azetidinyl, oxetanyl, thietanyl, pyrrolidinyl, tetrahydrofuranyl, thiolanyl, imidazolidinyl, pyrazolidinyl, isoxazolidinyl, isothiazolidinyl, piperidinyl, tetrahydropyranyl, thianyl, piperazinyl, morpholinyl, thiomorpholinyl, dioxanyl, dithianyl, azepanyl, oxepanyl, thiepanyl, dihydrofuranyl, imidazolinyl, dihydropyranyl, hydantoinyl, pyrrolidinonyl, tetrahydrothiopyranyl, tetrahydropyridinyl, and thiopyranyl, and the like. Examples of bicyclic heterocyclic ring systems include benzo[1,3]dioxolyl, tetrahydroindolyl, and 2-azaspiro[3.3]heptanyl, and the like. As used herein, a bicyclic heterocyclyl or a bicyclic heterocyclic ring system includes bicyclic ring systems where a monocyclic heterocyclyl is fused to another monocyclic heterocyclyl; bicyclic ring systems where a monocyclic heterocyclyl is fused to a cycloaliphatic ring, and bicyclic ring systems where a monocyclic heterocyclyl is fused to a phenyl ring.

As used herein, the terms "heteroaryl" or "5 to 6 membered heteroaryl" "heteroaryl group", "heteroaromatic" and "heteroaromatic ring" are used interchangeably to refer to an aromatic 5- to 6-membered monocyclic ring system containing at least one heteroatom (e.g., oxygen, sulfur, nitrogen or combinations thereof) within a 5- to 6-membered aromatic ring system (e.g., pyrrolyl, pyridyl, pyrazolyl, thienyl, furanyl, oxazolyl, imidazolyl, tetrazolyl, triazinyl, pyrimidyl, pyrazinyl, thiazolyl, and the like.) within a 9- to 10-membered aromatic ring system (e.g., 2,3-dihydrobenzofuran, 2,3-dihydrofuro[2,3-b]pyridine, 2,3-dihydrofuro[3,2-b]pyridine, 2,3-dihydrofuro[2,3-c]pyridine, 2,3-dihydrofuro[3,2-c]pyridine, 3,3a-dihydrofuro[3,2-c]pyridin-6 (2H)-one, 2,3-dihydrofuro[2,3-c]pyridin-5 (7aH)-one, and the like.)

As used herein, the term "cycloalkyl" refers to completely saturated monocyclic or bicyclic (e.g., fused, spiro or bridged) cycloaliphatic groups of 3-12 carbon atoms, 3-6 carbon atoms or 5-7 carbon atoms.

As used herein, the term "halocycloalkyl" refers to a cycloalkyl, as defined herein, that is substituted by one or more halo groups as defined herein.

The term "fused" referring to a bicyclic ring system as used herein, is a bicyclic ring system that has a carbocyclyl or heterocyclyl ring wherein two adjacent atoms of the ring are connected (bridged) by one or more (preferably from one to three) atoms selected from C, N, O or S. A fused ring system may have from 4-10 ring members.

The term "spiro" referring to a bicyclic ring system as used herein, is a bicyclic ring system that has two rings each of which are independently selected from a carbocyclyl or a heterocyclyl, wherein the two ring structures having one ring atom in common. Spiro ring systems have from 5 to 7 ring members. Exemplary spiro ring carbocyclyl groups include spiro[2.2]pentanyl and spiro[3.3]heptanyl.

Pharmaceutically acceptable salts of the compounds disclosed herein are also included in the invention. In cases where a compound provided herein is sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiologically acceptable anion, for example, tosylate, methanesulfonate, acetate, citrate, malonate, tartarate, succinate, benzoate, ascorbate, α-ketoglutarate or α-glycerophosphate. Inorganic salts may also be formed, including hydrochloride, sulfate, nitrate, bicarbonate and carbonate salts.

Pharmaceutically acceptable salts may be obtained using standard procedures well known in the art, for example by reacting a sufficiently basic compound such as an amine with a suitable acid; affording a physiologically acceptable anion. Alkali metal (for example, sodium, potassium or lithium) or alkaline earth metal (for example calcium) salts of carboxylic acids can also be made.

Pharmaceutically acceptable base addition salts can be prepared from inorganic and organic bases. Suitable bases include but are not limited to alkali metal hydroxides, alkaline earth metal hydroxides, carbonates, bicarbonates, and the like.

Some of the disclosed compounds, or pharmaceutically acceptable salts thereof, contain one or more asymmetric centers in the molecule. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis or chromatographic separation using a chiral stationary phase). The disclosed compounds may exist in tautomeric forms and mixtures and separate individual tautomers are contemplated. In addition, some compounds may exhibit polymorphism.

When a particular stereoisomer (e.g., enantiomer, diasteromers, etc.) of a compound used in the disclosed methods is depicted by name or structure, the stereochemical purity of the compounds is at least 60%, 70%, 80%, 90%, 95%, 97%, 99%, 99.5% or 99.9%. "Stererochemical purity" means the weight percent of the desired stereoisomer relative to the combined weight of all stereoisomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

In one embodiment, any position occupied by hydrogen is meant to include enrichment by deuterium above the natural abundance of deuterium as well. For example, one or more hydrogen atoms are replaced with deuterium at an abundance that is at least 3340 times greater than the natural abundance of deuterium, which is 0.015% (i.e., at least 50.1% incorporation of deuterium), at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In one embodiment, hydrogen is present at all positions at its natural abundance. The compounds or pharmaceutically acceptable salts thereof as described herein, may exist in tautomeric forms and mixtures and separate individual tautomers are contemplated.

One aspect of the invention includes a method for inhibiting a glycosidase and/or a glycosidase signaling pathway in a cell, the method comprising contacting the cell with an effective amount of a compound of any one of formulas (I) through (IIIA), or a pharmaceutically acceptable salt thereof. The glycosidase is preferably a glycoside hydrolase, more preferably a family 84 glycoside hydrolase, even more preferably O-glycoprotein-2-acetamido-2-deoxy-3-D-glucopyranosidase (O-GlcNAcase or OGA), most preferably a mammalian O-GlcNAcase. In one embodiment, the cell is contacted in vitro or in vivo. In one embodiment, contacting the cell includes administering the compound to a subject.

One aspect of the invention includes a method for inhibiting a glycosidase and/or a glycosidase signaling pathway in a subject in need thereof, the method comprising administering to the subject, a therapeutically effective amount of a compound of any one of formulas (I) through (IIIA), or a pharmaceutically acceptable salt thereof, thereby activating the glycosidase in the subject. The glycosidase is preferably a glycoside hydrolase, more preferably a family 84 glycoside hydrolase, even more preferably O-glycoprotein-2-acetamido-2-deoxy-3-D-glucopyranosidase (O-GlcNAcase or OGA), most preferably a mammalian O-GlcNAcase.

One aspect of the invention includes a method for promoting survival of a eukaryotic cell (e.g., a mammalian cell) or increasing the lifespan of the cell, the method comprising administering to the subject a therapeutically effective amount of a compound of any one of formulas (I) through (IIIA), or a pharmaceutically acceptable salt thereof, thereby promoting survival of the eukaryotic cell or increasing the lifespan of the cell.

One aspect of the invention includes a method for treating a disease or a condition that is caused, mediated and/or propagated by O-GlcNAcase activity in a subject, the method comprising administering to the subject a therapeutically effective amount of a compound of any one of formulas (I) through (IIIA), or a pharmaceutically acceptable salt thereof. Preferably, the disease or condition is a neurological disorder, diabetes, cancer or stress. More preferably, the disease or condition is a neurological disorder. In one embodiment, the neurological disorder is one or more tauopathies selected from Acute ischemic stroke (AIS), Alzheimer's disease, Dementia, Amyotrophic lateral sclerosis (ALS), Amyotrophic lateral sclerosis with cognitive impairment (ALSci), Argyrophilic grain dementia, Bluit disease, Corticobasal degeneration (CBP), Dementia pugilistica, Diffuse neurofibrillary tangles with calcification, Down's syndrome, epilepsy, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), ischemic stroke, mild cognitive impairment (MCI), Multiple system atrophy, Myotonic dystrophy, Niemann-Pick disease (type C), Pallido-ponto-nigral degeneration, Parkinsonism-dementia complex of Guam, Pick's disease (PiD), Postencephalitic parkinsonism (PEP), Prion diseases (including Creutzfeldt-Jakob Disease (GJD), Variant Creutzfeldt-Jakob Disease (vCJD), Fatal Familial Insomnia, Kuru, Progressive supercortical gliosis, Progressive supranuclear palsy (PSP), Steele-Richardson-Olszewski syndrome, Subacute sclerosing panencephalitis, Tangle-only dementia, Huntington's disease, and Parkinson's disease. In another embodiment, the neurological disorder is one or more tauopathies selected from Acute ischemic stroke (AIS), Alzheimer's disease, Dementia, Amyotrophic lateral sclerosis (ALS), Amyotrophic lateral sclerosis with cognitive impairment (ALSci), Argyrophilic grain dementia, epilepsy, mild cognitive impairment (MCI), Huntington's disease, and Parkinson's disease. In yet another embodiment, the neurological disorder is Alzheimer's disease.

One aspect of the invention includes a method for treating a disease or a condition that is characterized by hyperphosphorylation of tau (e.g., hyperphosphorylation of tau in the brain) in a subject, the method comprising administering to the subject a therapeutically effective amount of a compound of any one of formulas (I) through (IIIA), or a pharmaceutically acceptable salt thereof. In one embodiment, the disease or condition is selected from Acute ischemic stroke (AIS), Alzheimer's disease, Dementia, Amyotrophic lateral sclerosis (ALS), Amyotrophic lateral sclerosis with cognitive impairment (ALSci), Argyrophilic grain dementia, Bluit disease, Corticobasal degeneration (CBP), Dementia pugilistica, Diffuse neurofibrillary tangles with calcification, Down's syndrome, epilepsy, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), ischemic stroke, mild cognitive impairment (MCI), Multiple system atrophy, Myotonic dystrophy, Niemann-Pick disease (type C), Pallido-ponto-nigral degeneration, Parkinsonism-dementia complex of Guam, Pick's disease (PiD), Postencephalitic parkinsonism (PEP), Prion diseases (including Creutzfeldt-Jakob Disease (GJD), Variant Creutzfeldt-Jakob Disease (vCJD), Fatal Familial Insomnia, Kuru, Progressive supercortical gliosis, Progressive supranuclear palsy (PSP), Steele-Richardson-Olszewski syndrome, Subacute sclerosing panencephalitis, Tangle-only dementia, Huntington's disease, and Parkinson's disease. In another embodiment, the disease or condition is selected from Acute ischemic stroke (AIS), Alzheimer's disease, Dementia, Amyotrophic lateral sclerosis (ALS), Amyotrophic lateral sclerosis with cognitive impairment (ALSci), Argyrophilic grain dementia, epilepsy, ischemic stroke, mild cognitive impairment (MCI), Huntington's disease, and Parkinson's disease. In yet another embodiment, the disease or condition is Alzheimer's disease.

As used herein, the term "subject" and "patient" may be used interchangeably, and means a mammal in need of treatment, e.g., companion animals (e.g., dogs, cats and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or 'treatment" refers to obtaining desired pharmacological and/or physiological effect. The effect can be therapeutic, which includes achieving, partially or substantially, one or more of the following results: reducing the extent of the disease, disorder or syndrome; ameliorating or improving a clinical symptom or indicator associated with the disorder; and inhibiting or decreasing the likelihood of the progression of the disease, disorder or syndrome.

The term "an effective amount" means an amount of a compound of any one of formulas (I) through (IIIA), or a pharmaceutically acceptable salt thereof, e.g., 0.1 mg to 1000 mg/kg body weight, when administered to a subject, which results in beneficial or desired results, including clinical results, i.e., reversing, alleviating, inhibiting, reducing or slowing the progression of a disease or condition treatable by a compound of any one of formulas (I) through (IIIA), or a pharmaceutically acceptable salt thereof, reducing the likelihood of recurrence of a disease or condition treatable by a compound of any one of formulas (I) through (IIIA), or a pharmaceutically acceptable salt thereof or one or more symptoms thereof, e.g., as determined by clinical symptoms, compared to a control. The expression "an effective amount" also encompasses the amounts which are effective for increasing normal physiological function, for example, between 0.01 mg/kg per day to 500 mg/kg per day.

Another embodiment of the present invention is a pharmaceutical composition comprising at least one compound described herein, or a pharmaceutically acceptable salt thereof, and at least one pharmaceutically acceptable carrier.

Also included are the use of a compound of any one of formulas (I) through (IIIA), or a pharmaceutically acceptable salt thereof in the manufacture of a medicament for the treatment of one or more diseases or conditions described herein. Also included herein are pharmaceutical compositions comprising a compound of any one of formulas (I) through (IIIA), or a pharmaceutically acceptable salt thereof optionally together with a pharmaceutically acceptable carrier, in the manufacture of a medicament for the treatment of one or more diseases or conditions described herein. Also included is a compound of any one of formulas (I) through (IIIA), or a pharmaceutically acceptable salt thereof for use the treatment of a subject with one or more diseases or conditions described herein. Further included are pharmaceutical compositions comprising a compound of any one of formulas (I) through (IIIA), or a pharmaceutically acceptable salt thereof, optionally together with a pharmaceutically acceptable carrier, for use in the treatment of one or more diseases or conditions described herein.

The term "pharmaceutically acceptable carrier" refers to a non-toxic carrier, diluent, adjuvant, vehicle or excipient that does not adversely affect the pharmacological activity of the compound with which it is formulated, and which is also safe for human use. Pharmaceutically acceptable carriers that may be used in the compositions of this disclosure include, but are not limited to, ion exchangers, alumina, aluminum stearate, magnesium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (e.g., microcrystalline cellulose, hydroxypropyl methylcellulose, lactose monohydrate, sodium lauryl sulfate, and crosscarmellose sodium), polyethylene glycol, sodium carboxymethylcellulose, polyacrylates, waxes, polyethylene-polyoxypropylene-block polymers, polyethylene glycol and wool fat.

Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5th Ed., a Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003, 20th edition) and in The United States Pharmacopeia: The National Formulary (USP 24 NF19) published in 1999.

A compound of any one of formulas (I) through (IIIA), or a pharmaceutically acceptable salt thereof, or the compositions of the present teachings may be administered, for example, by oral, parenteral, sublingual, topical, rectal, nasal, buccal, vaginal, transdermal, patch, pump administration or via an implanted reservoir, and the pharmaceutical compositions would be formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

Other forms of administration included in this disclosure are as described in WO 2013/075083, WO 2013/075084, WO 2013/078320, WO 2013/120104, WO 2014/124418, WO 2014/151142, and WO 2015/023915, the contents of which are incorporated herein by reference.

Useful dosages of a compound or pharmaceutically acceptable salt thereof as described herein can be determined by comparing their in vitro activity and in vivo activity in animal models. Methods for the extrapolation of effective dosages in mice and other animals, to humans are known to the art; for example, see U.S. Pat. No. 4,938,949, which is incorporated by reference in its entirety.

EXEMPLIFICATIONS

General Methods

Chromatography on silica gel was carried out using 20-40 uM (particle size), 250-400 mesh, or 400-632 mesh silica gel using either a Teledyne ISCO Combiflash RF or a Grace Reveleris X2 with ELSD purification systems.

Analytical HPLC

Acidic HPLC: Conducted on a Shimadzu 20A instrument with an Ultimate C18 3.0×50 mm, 3 μm column eluting with 2.75 mL/4 L TFA in water (solvent A) and 2.5 mL/4 L TFA in acetonitrile (solvent B) by the following methods:

Method A: using the following elution gradient 0%-60% (solvent B) over 6 minutes and holding at 60% for 2 minutes at a flow rate of 1.2 ml/minutes. Wavelength: UV 220 nm, 215 nm and 254 nm.

Method B: using the following elution gradient 10%-80% (solvent B) over 6 minutes and holding at 60% for 2 minutes at a flow rate of 1.2 ml/minutes. Wavelength: UV 220 nm, 215 nm and 254 nm.

Method C: using the following elution gradient 30%-90% (solvent B) over 6 minutes and holding at 60% for 2 minutes at a flow rate of 1.2 ml/minutes. Wavelength: UV 220 nm, 215 nm and 254 nm.

Basic HPLC: Conducted on a Shimadzu 20A instrument with Xbridge Shield RP-18, 5 um, 2.1×50 mm column eluting with 2 mL/4 L $NH_3H_2O$ in water (solvent A) and acetonitrile (solvent B), by the following methods:

Method D: using the following elution gradient 0%-60% (solvent B) over 4.0 minutes and holding at 60% for 2 minutes at a flow rate of 1.2 ml/minutes.

Method E: using the following elution gradient 10%-80% (solvent B) over 4.0 minutes and holding at 60% for 2 minutes at a flow rate of 1.2 ml/minutes.

Method F: using the following elution gradient 30%-90% (solvent B) over 4.0 minutes and holding at 60% for 2 minutes at a flow rate of 1.2 ml/minutes.

Analytical LCMS

Acidic LCMS: Conducted on a Shimadzu 2010 Series, Shimadzu 020 Series, or Waters Acquity UPLC BEH. (MS ionization: ESI) instrument equipped with a C18 column (2.1 mm×30 mm, 3.0 mm or 2.1 mm×50 mm, C18, 1.7 um), eluting with 1.5 mL/4 L TFA in water (solvent A) and 0.75 mL/4 L TFA in acetonitrile (solvent B) using the methods below:

1.5 Minute Methods:

General method: using the following elution gradient 5%-95% (solvent B) over 0.7 minutes and holding at 95% for 0.4 minutes at a flow rate of 1.5 ml/minutes. Wavelength: UV 220 nm and 254 nm.

2 Minute Methods:

Method A: using the following elution gradient 0%-60% (solvent B) over 0.9 minutes and holding at 60% for 0.6 minutes at a flow rate of 1.2 ml/minutes. Wavelength: UV 220 nm and 254 nm.

Method B: using the following elution gradient 10%-80% (solvent B) over 0.9 minutes and holding at 60% for 0.6 minutes at a flow rate of 1.2 ml/minutes. Wavelength: UV 220 nm and 254 nm.

Method C: using the following elution gradient 30%-90% (solvent B) over 0.9 minutes and holding at 60% for 0.6 minutes at a flow rate of 1.2 ml/minutes. Wavelength: UV 220 nm and 254 nm.

3.5 Minute Method:

Initial conditions, solvent A-95%: solvent B-5%; hold at initial from 0.0-0.1 min; Linear Ramp to solvent A-5%: solvent B-95% between 0.1-3.25 min; hold at solvent A-5%: solvent B-95% between 3.25-3.5 min. Diode array/MS detection.

4 Minute Methods:

Method A: using the following elution gradient 0%-60% (solvent B) over 3 minutes and holding at 60% for 0.5 minutes at a flow rate of 0.8 ml/minutes. Wavelength: UV 220 nm and 254 nm.

Method B: using the following elution gradient 10%-80% (solvent B) over 3 minutes and holding at 60% for 0.5 minutes at a flow rate of 0.8 ml/minutes. Wavelength: UV 220 nm and 254 nm.

Method C: using the following elution gradient 30%-90% (solvent B) over 3 minutes and holding at 60% for 0.5 minutes at a flow rate of 0.8 ml/minutes. Wavelength: UV 220 nm and 254 nm.

7 Minute Methods:

Method A: using the following elution gradient 0%-60% (solvent B) over 6 minutes and holding at 60% for 0.5 minutes at a flow rate of 0.8 ml/minutes. Wavelength: UV 220 nm and 254 nm.

Method B: using the following elution gradient 10%-80% (solvent B) over 6 minutes and holding at 60% for 0.5 minutes at a flow rate of 0.8 ml/minutes. Wavelength: UV 220 nm and 254 nm.

Method C: using the following elution gradient 30%-900% (solvent B) over 6 minutes and holding at 60% for 0.5 minutes at a flow rate of 0.8 ml/minutes. Wavelength: UV 220 nm and 254 nm.

Basic LCMS:

Conducted on a Shimadzu 2020 Series or Waters Acquity UPLC BEH (MS ionization: ESI) instrument equipped with XBridge Shield RP18, 5 μm column (2.1 mm×30 mm, 3.0 mm i.d.) or 2.1 mm×50 mm, C18, 1.7 um column, eluting with 2 mL/4 L $NH_3 \cdot H_2O$ in water (solvent A) and acetonitrile (solvent B) using the methods below:

3 Minute Methods:

Method A: using the following elution gradient 0%-60% (solvent B) over 2 minutes and holding at 60% for 0.48 minutes at a flow rate of 1 ml/minutes. Wavelength: UV 220 nm and 254 nm.

Method B: using the following elution gradient 10%-80% (solvent B) over 2 minutes and holding at 60% for 0.48 minutes at a flow rate of 1 ml/minutes. Wavelength: UV 220 nm and 254 nm.

Method C: using the following elution gradient 30%-90% (solvent B) over 2 minutes and holding at 60% for 0.48 minutes at a flow rate of 1 ml/minutes. Wavelength: UV 220 nm and 254 nm.

3.5 Minute Method:

Initial conditions, solvent A-95%: solvent B-5%; hold at initial from 0.0-0.1 min; Linear Ramp to solvent A-5%: solvent B-95% between 0.1-3.25 min; hold at solvent A-5%: solvent B-95% between 3.25-3.5 min. Diode array/MS detection.

7 Minute Methods:

Method A: using the following elution gradient 0%-60% (solvent B) over 6 minutes and holding at 60% for 0.5 minutes at a flow rate of 0.8 ml/minutes. Wavelength: UV 220 nm and 254 nm.

Method B: using the following elution gradient 10%-80% (solvent B) over 6 minutes and holding at 60% for 0.5 minutes at a flow rate of 0.8 ml/minutes. Wavelength: UV 220 nm and 254 nm.

Method C: using the following elution gradient 30%-90% (solvent B) over 6 minutes and holding at 60% for 0.5 minutes at a flow rate of 0.8 ml/minutes. Wavelength: UV 220 nm and 254 nm.

SFC Analytical Separation

Instrument: Waters UPC2 analytical SFC (SFC—H). Column: ChiralCel OJ, 150×4.6 mm I.D., 3 μm. Mobile phase: A for CO2 and B for Ethanol (0.05% DEA). Gradient: B 40%. Flow rate: 2.5 mL/min. Back pressure: 100 bar. Column temperature: 35° C. Wavelength: 220 nm Preparative HPLC Purification General Method: Preparative HPLC was performed on a Gilson UV/VIS-156 with UV detection at 220/254 nm Gilson 281 automatic collection.

Acidic condition: Two acid grading systems used: Hydrochloride acid and Formic acid.

Method A: Hydrochloride acid: YMC-Actus Triart C18 150×30 mm×5 um, Gradient used 0-100% acetonitrile with water and corresponding acid (0.05% HCl).

Method B: Formic acid: Phenomenex Synergi C18 150×30 mm×4 um, Gradient used 0-100% acetonitrile with water and corresponding acid (0.225% formic acid), the gradient shape was optimized for individual separations.

Neutral condition: Xtimate C18 150×25 mm×5 um, Gradient used 0-100% (water (10 mM $NH_4HCO_3$)-ACN), the gradient shape was optimized for individual separations.

Basic condition: Waters Xbridge Prep OBD C18 150×30 10 um, Gradient used 0-100% water (0.04% $NH_3H_2O$+10 mM $NH_4HCO_3$)-acetonitrile, the gradient shape was optimized for individual separations.

Preparative HPLC-MS Purification

Columns Used:

Acid: Waters SunFire Prep, C18 5 um, OBD 19×100 mm

Base: Waters XSelect CSH Prep C18 5 um OBD 19×100 mm

Gradient Profile: 12 min Run: Initial conditions: A-95%: B-5%; hold at initial from 0.0-0.5 min; linear ramp from A-5% to variable B-% (typical range is from B-40% to B-75%) between 0.5-7.5 min; linear ramp from B-% to B-95% from 7.5-8.0 min; hold at A-5%: B-95% between 8.0-10.0 min; end of DAD/MS detection; linear ramp down to initial conditions between 10.0-10.5 min and hold at initial for 1.5 min.

Mobile Phase: Acid: A: 0.1% trifluoroacetic acid in water (v/v); Mobile phase B: 0.1% trifluoroacetic acid in acetonitrile (v/v). Base: A: 0.1% ammonia in water (v/v); Mobile phase B: 0.1% ammonia in acetonitrile (v/v)

Preparative SFC Purification

Instrument: MG III preparative SFC (SFC-1). Column: ChiralCel OJ, 250×30 mm I.D., 5 μm. Mobile phase: A for $CO_2$ and B for Ethanol (0.1% $NH_3H_2O$). Gradient: B 50%. Flow rate: 40 mL/min. Back pressure: 100 bar. Column temperature: 38° C. Wavelength: 220 nm. Cycle time: ~8 min.

$^1$H-NMR

The NMR spectra were recorded on Bruker Avance III HD 500 MHz, Bruker Avance III 500 MHz, Bruker Avance III 400 MHz, Varian UNITYplus 400, Varian-400 VNMRS, or Varian-400 MR. Chemical shifts are expressed in parts per million (ppm) units. Coupling constants (J) are in units of hertz (Hz). Splitting patterns describe apparent multiplicities and are designated as s (single), d (double), t (triplet), dd (double doublet), dt (double triplet), dq (double quartet), m (multiplet), br (broad).

The following general reaction Schemes 1, 2, 3, and 4 provide useful details for preparing the instant compounds. The requisite intermediates are in some cases commercially available or can be prepared according to literature procedures. The illustrative reaction schemes are not limited by the compounds listed or by any particular substituents employed for illustrative purposes substituent labeling (i.e. R groups) as shown in the reaction schemes do not necessarily correlate to that used in the claims and often, for clarity, a single substituent is shown attached to the compound where multiple substituents are allowed under the definitions of Formula (I) hereinabove.

General Procedure 1

Example 1: N-(4-Fluoro-5-(((2R,5'S)-5'-methyl-3H-spiro[benzofuran-2,3'-pyrrolidin]-1'-yl)methyl)thiazol-2-yl)acetamide

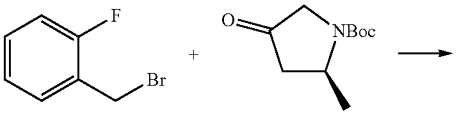

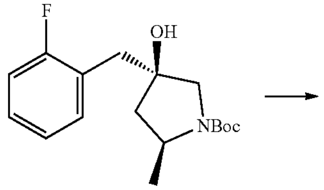

1.1

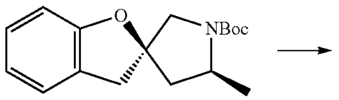

1.2

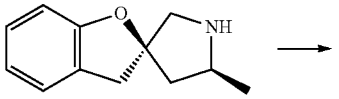

1.3

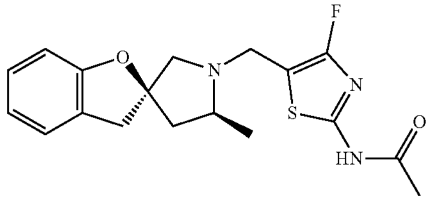

ex. 1

Compound 1.1: tert-Butyl (2S,4R)-4-(2-fluorobenzyl)-4-hydroxy-2-methylpyrrolidine-1-carboxylate: To a mixture of magnesium powder (372 mg, 15.3 mmol) and molecular iodine (26 mg, 100 umol) in ether (5.0 mL) was slowly added 1-(bromomethyl)-2-fluoro-benzene (1.15 g, 6.07 mmol) at reflux. The mixture was stirred at reflux for 30 min. Cooled down, let the metal sit and take the top clear solution of Grignard reagent and added dropwise to a solution of tert-butyl (2S)-2-methyl-4-oxo-pyrrolidine-1-carboxylate (1.00 g, 5.02 mmol) in ether (30.0 mL) at −78° C. The reaction was then stirred at rt for 1 h. Saturated $NH_4Cl$ was then added, the product was extracted with EtOAc. The organic layer was then separated, dried and concentrated. The crude was purified by chromatography on silica gel (0-100% EtOAc in heptane) to give the title compound (552 mg, 35% yield). $^1$H NMR (400 MHz, CHLOROFORM-d) δ 7.27-7.30 (m, 1H), 7.22-7.26 (m, 1H), 7.04-7.15 (m, 2H), 3.96 (br s, 1H), 3.55 (br d, J=11.80 Hz, 1H), 3.35 (dd, J=1.13, 11.67 Hz, 1H), 2.95 (s, 2H), 2.23 (dd, J=8.66, 13.18 Hz, 1H), 1.62 (br dd, J=3.01, 13.05 Hz, 1H), 1.47 (s, 9H), 1.35 (d, J=6.27 Hz, 3H); LCMS (ESI): [M+H] 310.

Compound 1.2: tert-Butyl (2R,5'S)-5'-methyl-3H-spiro[benzofuran-2,3'-pyrrolidine]-1'-carboxylate: A mixture of tert-butyl (2S,4R)-4-(2-fluorobenzyl)-4-hydroxy-2-methylpyrrolidine-1-carboxylate (400 mg, 1.29 mmol) and potassium tert-butoxide (363 mg, 3.23 mmol) in THF (8.0 mL) was heated at 65° C. overnight. Cooled down, water was added, the product was extracted with EtOAc. The organic layer was then separated, dried and concentrated. The crude was purified by chromatography on silica gel (0-80% EtOAc in heptane) to give the title compound (178 mg, 48% yield). $^1$H NMR (400 MHz, CHLOROFORM-d) δ 7.10-7.20 (m, 2H), 6.86 (t, J=7.40 Hz, 1H), 6.78 (br d, J=8.03 Hz, 1H); 3.93-4.13 (m, 1H), 3.79 (br d, J=11.29 Hz, 1H), 3.51 (br d, J=17.07 Hz, 1H), 3.11-3.34 (m, 2H), 2.18-2.28 (m, 1H), 2.06-2.15 (m, 1H), 1.46-1.53 (m, 9H), 1.44 (br s, 3H); LCMS (ESI): [M-tBu] 234.

Compound 1.3: (2R,5'S)-5'-Methyl-3H-spiro[benzofuran-2,3'-pyrrolidine]: To a solution of tert-butyl (2R,5'S)-5'-methyl-3H-spiro[benzofuran-2,3'-pyrrolidine]-1'-carboxylate (130 mg, 449.2 umol) in DCM (3.0 mL) was added TFA (344 uL, 4.49 mmol). The mixture was stirred at rt overnight. Remove all the solvent to give the title compound (185 mg, 99% yield, 2TFA). LCMS (ESI): [M+H] 190.

Example 1: N-(4-Fluoro-5-(((2R,5'S)-5'-methyl-3H-spiro[benzofuran-2,3'-pyrrolidin]-1'-yl)methyl)thiazol-2-yl)acetamide

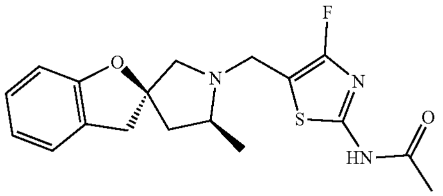 [SMILES: CC(=O)Nc1nc(F)c(CN2C[C@@]3(Cc4ccccc4O3)C[C@@H]2C)s1]

To a solution of (2R,5'S)-5'-methyl-3H-spiro[benzofuran-2,3'-pyrrolidine] (185 mg, 443 umol, 2TFA) in EtOAc (3.0 mL) was added Hunigs base (57 mg, 443.3 umol). Stirred for 5 min. Sodium triacetoxyborohydride (282 mg, 1.3 mmol) was added, followed by N-(4-fluoro-5-formyl-thiazol-2-yl) acetamide (167 mg, 887 umol). The reaction was heated at 60° C. for 2 h. Cooled down, the reaction mixture was washed with aq. $NaHCO_3$, the organic layer was separated, dried and concentrated. The crude was purified by chromatography on silica gel (0-80% EtOAc-EtOH 3:1 with 2% $NH_4OH$ in heptane) to give the title compound (56 mg, 35% yield). $^1$H NMR (400 MHz, METHANOL-d4) δ 7.21 (d, J=7.53 Hz, 1H), 7.10-7.17 (m, 1H), 6.87-6.93 (m, 1H), 6.78 (d, J=8.03 Hz, 1H), 4.62-4.73 (m, 1H), 4.45-4.55 (m, 1H), 3.94 (br dd, J=6.53, 15.81 Hz, 1H), 3.79 (dd, J=1.88, 11.92 Hz, 1H), 3.42-3.51 (m, 1H), 3.36 (s, 2H), 2.76 (dd, J=10.04, 14.31 Hz, 1H), 2.24-2.33 (m, 1H), 2.21 (s, 3H), 1.58 (d, J=6.78 Hz, 3H); LCMS (ESI): [M+H] 362.

Example 2: N-(5-(((2R,5'S)-5'-Methyl-3H-spiro[benzofuran-2,3'-pyrrolidin]-1'-yl)methyl)thiazol-2-yl)acetamide

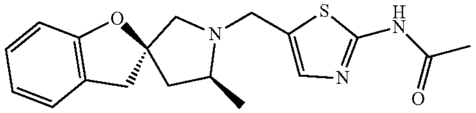 [SMILES: CC(=O)Nc1ncc(CN2C[C@@]3(Cc4ccccc4O3)C[C@@H]2C)s1]

To a mixture (2R,5'S)-5'-methyl-3H-spiro[benzofuran-2,3'-pyrrolidine] (Compound 1.3, 30 mg, 132.9 umol) and N-[5-(chloromethyl)thiazol-2-yl]acetamide (51 mg, 266 umol) in acetonitrile (1.0 mL) was added Hunig's base (86 mg, 664.6 umol). The reaction was stirred at rt for 2 h. Remove all the solvent, the crude was purified by chromatography on silica gel (0-80% EtOAc-EtOH 3:1 with 2% $NH_4OH$ in heptane) to give the title compound (18 mg, 39% yield). $^1$H NMR (400 MHz, METHANOL-$d_4$) δ 7.27 (s, 1H), 7.11 (d, J=7.53 Hz, 1H), 7.05 (t, J=7.65 Hz, 1H), 6.78 (dt, J=0.75, 7.40 Hz, 1H), 6.67 (d, J=7.78 Hz, 1H), 4.13 (d, J=14.05 Hz, 1H), 3.64 (d, J=14.31 Hz, 1H), 3.25 (d, J=11.04 Hz, 1H), 3.16 (s, 2H), 2.67-2.83 (m, 1H), 2.47 (d, J=10.54 Hz, 1H), 2.31 (dd, J=7.91, 13.68 Hz, 1H), 2.19 (s, 3H), 2.00 (ddd, J=1.13, 8.47, 13.74 Hz, 1H), 1.26 (d, J=6.02 Hz, 3H); LCMS (ESI): [M+H] 344.

Example 3: N-(5-((3H-Spiro[benzofuran-2,3'-pyrrolidin]-1'-yl)methyl)thiazol-2-yl)acetamide

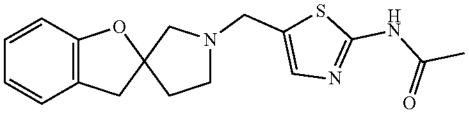 [SMILES: CC(=O)Nc1ncc(CN2CCC3(Cc4ccccc4O3)C2)s1]

The title compound was prepared in an analogous manner of that in Example 2 from 3H-spiro[benzofuran-2,3'-pyrrolidine] and N-(5-(chloromethyl)thiazol-2-yl)acetamide. $^1$H NMR (500 MHz, METHANOL-$d_4$) δ 7.27 (s, 1H), 7.13 (d, J=7.32 Hz, 1H), 7.06 (t, J=7.71 Hz, 1H), 6.79 (dt, J=0.76, 7.40 Hz, 1H), 6.67 (d, J=7.93 Hz, 1H), 3.82-3.92 (m, 2H), 3.18-3.28 (m, 2H), 3.01 (d, J=10.53 Hz, 1H), 2.89-2.96 (m, 1H), 2.73-2.79 (m, 2H), 2.29 (ddd, J=5.49, 7.40, 13.35 Hz, 1H), 2.18-2.22 (m, 3H), 2.05-2.13 (m, 1H); LCMS (ESI): [M+H] 330.

Example 4: N-(4-Fluoro-5-((7-methoxy-3H-spiro[benzofuran-2,3'-pyrrolidin]-1'-yl)methyl)thiazol-2-yl)acetamide

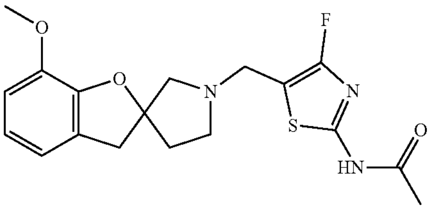 [SMILES: COc1cccc2c1OC1(CCN(Cc3sc(NC(C)=O)nc3F)C1)C2]

The title compound was prepared in an analogous manner of that in Example 1 from 7-methoxy-3H-spiro[benzofuran-2,3'-pyrrolidine] and N-(4-fluoro-5-formylthiazol-2-yl) acetamide. $^1$H NMR (400 MHz, METHANOL-$d_4$) δ 6.77 (s, 3H), 3.73-3.85 (m, 5H), 3.17-3.29 (m, 2H), 3.03 (d, J=10.54 Hz, 1H), 2.87-2.98 (m, 1H), 2.74-2.86 (m, 2H), 2.25-2.36 (m, 1H), 2.18 (s, 3H), 2.03-2.14 (m, 1H); LCMS (ESI): [M+H] 378.

Example 5: N-(5-((5-Chloro-3H-spiro[benzofuran-2,3'-pyrrolidin]-1'-yl)methyl)thiazol-2-yl)acetamide

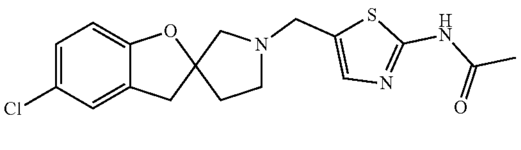 [SMILES: CC(=O)Nc1ncc(CN2CCC3(Cc4cc(Cl)ccc4O3)C2)s1]

The title compound was prepared in an analogous manner of that in Example 2 from 5-chloro-3H-spiro[benzofuran-2,3'-pyrrolidine] and N-(5-(chloromethyl)thiazol-2-yl)acetamide. $^1$H NMR (500 MHz, METHANOL-$d_4$) δ 7.27 (s, 1H), 7.11-7.16 (m, 1H), 7.04 (dd, J=2.29, 8.39 Hz, 1H), 6.65 (d, J=8.54 Hz, 1H), 3.79-3.95 (m, 2H), 3.19-3.29 (m, 2H), 3.01 (d, J=10.68 Hz, 1H), 2.92 (td, J=7.44, 9.23 Hz, 1H), 2.73-2.80 (m, 2H), 2.25-2.33 (m, 1H), 2.20 (s, 3H), 2.09 (ddd, J=7.02, 8.05, 13.77 Hz, 1H); LCMS (ESI): [M+H] 364.

Example 6: N-(5-((5-Chloro-3H-spiro[benzofuran-2,3'-pyrrolidin]-1'-yl)methyl)-4-fluorothiazol-2-yl) acetamide

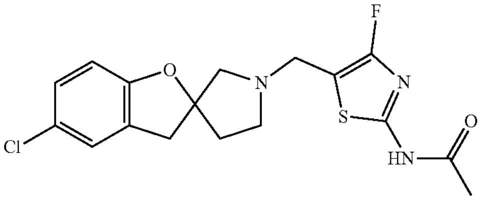 [SMILES: CC(=O)Nc1nc(F)c(CN2CCC3(Cc4cc(Cl)ccc4O3)C2)s1]

The title compound was prepared in an analogous manner of that in Example 1 from 5-chloro-3H-spiro[benzofuran-2,3'-pyrrolidine] and N-(4-fluoro-5-formylthiazol-2-yl) acetamide. $^1$H NMR (400 MHz, METHANOL-$d_4$) δ 7.14 (d, J=1.00 Hz, 1H), 7.05 (dd, J=1.63, 8.41 Hz, 1H), 6.65 (d, J=8.53 Hz, 1H), 3.77 (s, 2H), 3.17-3.29 (m, 2H), 3.02 (d, J=10.54 Hz, 1H), 2.88-2.97 (m, 1H), 2.72-2.81 (m, 2H), 2.25-2.35 (m, 1H), 2.18 (s, 3H), 2.05-2.14 (m, 1H); LCMS (ESI): [M+H] 382.

Example 7: N-(5-((6-Chloro-3H-spiro[furo[3,2-c]pyridine-2,3'-pyrrolidin]-1'-yl)methyl)-4-fluorothiazol-2-yl)acetamide

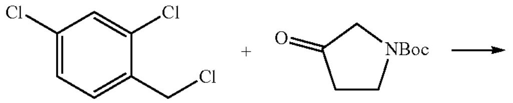

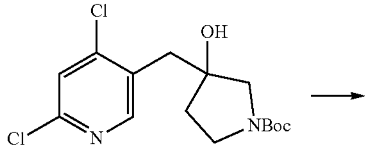

7.1

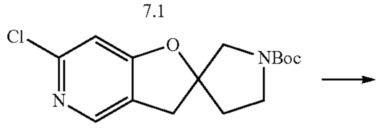

7.2

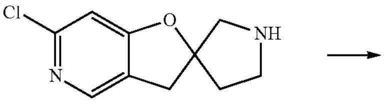

7.3

-continued

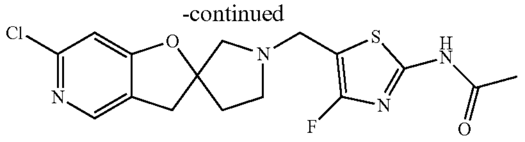

ex. 7

Compound 7.1: tert-Butyl 3-((4,6-dichloropyridin-3-yl)methyl)-3-hydroxypyrrolidine-1-carboxylate: Magnesium turnings (7.1 g, 297.7 mmol) were suspended in dry THF (600 mL) under argon atmosphere. Iodine (0.1 g, 0.394 mmol) was added thereto and the mixture was stirred for 30 min., followed by dropwise addition of a solution of 2,4-dichloro-5-(chloromethyl)pyridine (45 g, 229 mmol) in THF (50 mL). The mixture was stirred for 3 h and tert-butyl 3-oxopyrrolidine-1-carboxylate (42.5 g, 229 mmol) was added in portions. The reaction mixture was then stirred overnight. Saturated aq. $NH_4Cl$ solution (600 mL) was added to the reaction mixture, extracted with EtOAc (2×). The combined extracts were dried and evaporated in vacuum. The crude was purified by column chromatography on silica gel to obtain the title compound (8.3 g, 10% yield) as a yellow oil. LCMS (ESI): [M+H] 347.

Compound 7.2: tert-Butyl 6-chloro-3H-spiro[furo[3,2-c]pyridine-2,3'-pyrrolidine]-1'-carboxylate: To a solution of tert-butyl 3-((4,6-dichloropyridin-3-yl)methyl)-3-hydroxypyrrolidine-1-carboxylate (8 g, 23.0 mmol) in dry dioxane (100 mL) was added potassium tert-butoxide (5.2 g, 46.3 mmol) in one portion. The mixture was heated at 90° C. overnight. The reaction mixture was cooled to rt and concentrated under reduced pressure. The crude was chromatographed on silica gel to give the title compound (4.2 g, 59% yield) as a yellow solid. LCMS (ESI): [M+H] 311.

Compound 7.3: 6-Chloro-3H-spiro[furo[3,2-c]pyridine-2,3'-pyrrolidine]: The title compound was prepared in an analogous manner of that in Compound 1.3 from tert-butyl 6-chloro-3H-spiro[furo[3,2-c]pyridine-2,3'-pyrrolidine]-1'-carboxylate. LCMS (ESI): [M+H] 211.

The title compound was prepared in an analogous manner of that in Example 1 from 6-chloro-3H-spiro[furo[3,2-c]pyridine-2,3'-pyrrolidine] and N-(4-fluoro-5-formylthiazol-2-yl)acetamide. $^1$H NMR (400 MHz, METHANOL-$d_4$) δ 8.01 (s, 1H), 6.83 (s, 1H), 3.78 (s, 2H), 3.32 (br s, 1H), 3.29-3.30 (m, 1H), 3.08 (d, J=10.79 Hz, 1H), 2.95 (td, J=7.40, 9.03 Hz, 1H), 2.73-2.85 (m, 2H), 2.30-2.40 (m, 1H), 2.12-2.21 (m, 4H); LCMS (ESI): [M+H] 383.

Example 8: N-(5-((6-Chloro-3H-spiro[furo[3,2-c]pyridine-2,3'-pyrrolidin]-1'-yl)methyl)thiazol-2-yl) acetamide

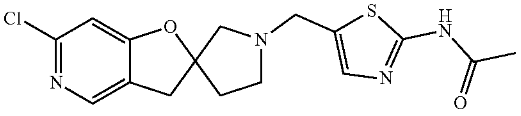 [SMILES: CC(=O)Nc1ncc(CN2CCC3(Cc4cnc(Cl)cc4O3)C2)s1]

The title compound was prepared in an analogous manner of that in Example 2 from 6-chloro-3H-spiro[furo[3,2-c]pyridine-2,3'-pyrrolidine] and N-(5-(chloromethyl)thiazol-2-yl)acetamide. $^1$H NMR (400 MHz, METHANOL-$d_4$) δ 8.01 (s, 1H), 7.27 (s, 1H), 6.83 (s, 1H), 3.82-3.95 (m, 2H), 3.35 (br d, J=11.29 Hz, 1H), 3.26 (s, 1H), 3.25-3.30 (m, 1H), 3.07 (d, J=11.04 Hz, 1H), 2.94 (td, J=7.40, 9.03 Hz, 1H), 2.72-2.84 (m, 2H), 2.34 (ddd, J=5.77, 7.34, 13.74 Hz, 1H), 2.20 (s, 3H), 2.11-2.19 (m, 1H); LCMS (ESI): [M+H] 365.

Example 9: N-(4-Fluoro-5-(((2R,5'S)-5'-methyl-3H-spiro[furo[2,3-c]pyridine-2,3'-pyrrolidin]-1'-yl)methyl)thiazol-2-yl)acetamide

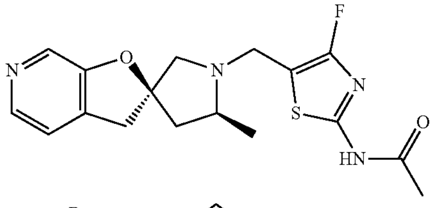

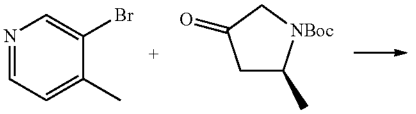

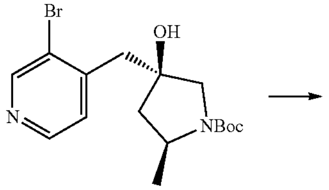

9.1

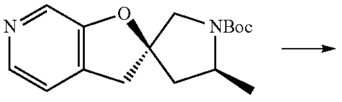

9.2

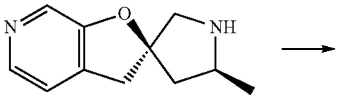

9.3

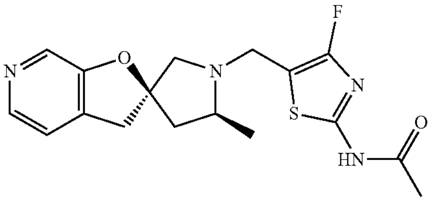

ex. 9

Compound 9.1: tert-Butyl (2S,4R)-4-((3-bromopyridin-4-yl)methyl)-4-hydroxy-2-methylpyrrolidine-1-carboxylate: To a solution of 3-bromo-4-methyl-pyridine (864 mg, 5.02 mmol) in ether (20.0 mL) was dropwise added LDA (2 M in THF, 2.51 mL) at −20° C. The reaction was stirred at −20° C. for 2 h. A solution of tert-butyl (2S)-2-methyl-4-oxo-pyrrolidine-1-carboxylate (500 mg, 2.51 mmol) in ether (5.0 mL) was then dropwise added, and the mixture was stirred at −20° C. for 3 h, then rt overnight. The reaction was then quenched by aq. $NH_4Cl$, extracted with EtOAc (3×). The combined organic layer was then washed with aq. $NaHCO_3$, brine, then dried and concentrated. The crude was purified by chromatography on silica gel (0-100% EtOAc in heptane) to give the title compound (281 mg, 30% yield). $^1$H NMR (400 MHz, CHLOROFORM-d) δ 8.73 (s, 1H), 8.45 (d, J=4.77 Hz, 1H), 7.38 (d, J=5.02 Hz, 1H), 3.88-4.08 (m, 1H), 3.57 (br s, 1H), 3.34-3.43 (m, 1H), 3.08-3.18 (m, 2H), 2.28 (dd, J=8.66, 13.18 Hz, 1H), 1.62-1.70 (m, 1H), 1.45-1.51 (m, 9H), 1.30-1.39 (m, 3H); LCMS (ESI): [M+H] 371.

Compound 9.2: tert-Butyl (2R,5'S)-5'-methyl-3H-spiro[furo[2,3-c]pyridine-2,3'-pyrrolidine]-1'-carboxylate: A mixture of tert-butyl (2S,4R)-4-((3-bromopyridin-4-yl)methyl)-4-hydroxy-2-methylpyrrolidine-1-carboxylate (270 mg, 727 umol), [2-(2-aminophenyl)phenyl]-methylsulfonyloxy-palladium; ditert-butyl-[3,6-dimethoxy-2-(2,4,6-triisopropylphenyl)phenyl]phosphane (12.4 mg, 14.5 umol), sodium tert-butoxide (105 mg, 1.09 mmol) in dioxane (6.0 mL) was heated in a sealed tube at 85° C. under nitrogen for 1 h. Cooled down, filter off the solid, the filtrate was concentrated and purified by chromatography on silica gel (0-60% EtOAc-EtOH 3:1 with 2% $NH_4OH$ in heptane) to give the title compound (177 mg, 83% yield). $^1$H NMR (400 MHz, CHLOROFORM-d) δ 8.13-8.21 (m, 2H), 7.16 (d, J=4.77 Hz, 1H), 4.04-4.23 (m, 1H), 3.82 (br d, J=12.55 Hz, 1H), 3.34-3.63 (m, 1H), 3.16-3.32 (m, 2H), 2.26 (dd, J=8.53, 13.55 Hz, 1H), 1.98-2.17 (m, 1H), 1.39-1.55 (m, 12H); LCMS (ESI): [M+H] 291.

Compound 9.3: (2R,5'S)-5'-Methyl-3H-spiro[furo[2,3-c]pyridine-2,3'-pyrrolidine]: The title compound was prepared in an analogous manner of that in Compound 1.3 from tert-butyl (2R,5'S)-5'-methyl-3H-spiro[furo[2,3-c]pyridine-2,3'-pyrrolidine]-1'-carboxylate. LCMS (ESI): [M+H] 191

The title compound was prepared in an analogous manner of that in Example 1 from (2R,5'S)-5'-methyl-3H-spiro[furo[2,3-c]pyridine-2,3'-pyrrolidine] and N-(4-fluoro-5-formylthiazol-2-yl)acetamide. $^1$H NMR (400 MHz, METHANOL-$d_4$) δ 8.01 (d, J=4.77 Hz, 1H), 7.98 (s, 1H), 7.27 (dd, J=0.88, 4.89 Hz, 1H), 3.98 (dd, J=1.00, 14.56 Hz, 1H), 3.65 (d, J=14.81 Hz, 1H), 3.32-3.34 (m, 1H), 3.29 (s, 2H), 2.69-2.82 (m, 1H), 2.54 (d, J=10.54 Hz, 1H), 2.35 (dd, J=7.91, 13.93 Hz, 1H), 2.18 (s, 3H), 2.03 (ddd, J=1.38, 8.28, 13.93 Hz, 1H), 1.27 (d, J=6.02 Hz, 3H); LCMS (ESI): [M+H] 363.

Example 10: N-(5-(((2R,5'S)-5-Chloro-5'-methyl-3H-spiro[furo[2,3-c]pyridine-2,3'-pyrrolidin]-1'-yl)methyl)-4-fluorothiazol-2-yl)acetamide

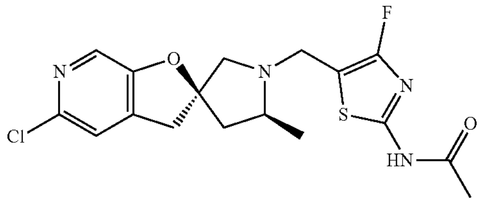

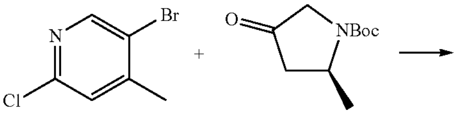

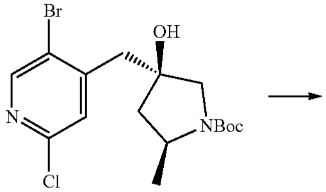

10.1

-continued

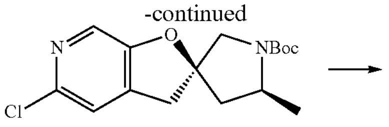

10.2

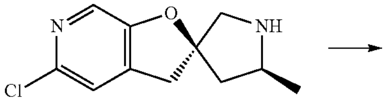

10.3

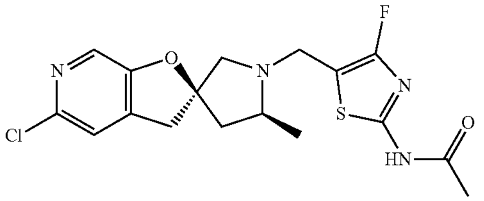

10

Compound 10.1: tert-Butyl (2S,4R)-4-((5-bromo-2-chloropyridin-4-yl)methyl)-4-hydroxy-2-methylpyrrolidine-1-carboxylate: n-BuLi (2.5 M in hexanes, 11.62 mL) was added dropwise to a solution of N-isopropylpropan-2-amine (2.94 g, 29.06 mmol, 4.08 mL) in THF (50.0 mL) at −20° C. The LDA solution was stirred at −20° C. for 1 h. To this, a solution of 5-bromo-2-chloro-4-methyl-pyridine (5.0 g, 24.22 mmol) in THF (15 mL) was dropwise added, and the mixture was stirred at −20° C. for 2 h. A solution of tert-butyl (2S)-2-methyl-4-oxo-pyrrolidine-1-carboxylate (4.83 g, 24.22 mmol) in THF (15 mL) was then dropwise added. The mixture was stirred at −20° C. for 30 min and slowly warmed up to rt overnight. Add aqueous $NH_4Cl$ to the mixture, extract with EtOAc, organic layer was dried, and concentrated. The crude solid was diluted with DCM/heptane (1:10). The solid was then washed with heptane to give 3.73 g of the title compound as off white solid. The mother liquor was concentrated and purified by chromatography on silica gel (0-60% EtOAc in heptane) to give another 450 mg of the title compound (total yield 42.5%). $^1H$ NMR (500 MHz, METHANOL-$d_4$) δ 8.50 (s, 1H), 7.57 (br s, 1H), 3.95 (br s, 1H), 3.48 (d, J=11.44 Hz, 1H), 3.27 (br d, J=11.44 Hz, 1H), 3.03-3.14 (m, 2H), 2.23-2.32 (m, 1H), 1.62-1.72 (m, 1H), 1.46 (s, 9H), 1.33 (d, J=6.41 Hz, 3H). LCMS (ESI): [M-tBu] 349/351.

Compound 10.2: tert-Butyl (2R,5'S)-5-chloro-5'-methyl-3H-spiro[furo[2,3-c]pyridine-2,3'-pyrrolidine]-1'-carboxylate: A mixture of sodium tert-butoxide (1.05 g, 10.94 mmol), DPEO (540.6 mg, 1.82 mmol), CuI (347.4 mg, 1.82 mmol) and fresh activated molecular sieve (3.7 g) in dioxane (80 mL) was sparged with nitrogen for 10 min. The mixture was heated to 80° C. for 10 min. Cooled down. The mixture was then added to a nitrogen purged solution of tert-butyl (2S,4R)-4-[(5-bromo-2-chloro-4-pyridyl)methyl]-4-hydroxy-2-methyl-pyrrolidine-1-carboxylate (3.70 g, 9.12 mmol) in dioxane (50 mL). The reaction was then heated at 80° C. for 1 h. Filter off the solid, the filtrate was concentrated and purified by chromatography on silica gel (0-80% EtOAc in heptane) to give the title compound (2.15 g, 72% yield). $^1H$ NMR (400 MHz, METHANOL-$d_4$) δ 7.81 (s, 1H), 7.31 (d, J=0.75 Hz, 1H), 4.03-4.16 (m, 1H), 3.75 (br d, J=12.30 Hz, 1H), 3.54 (d, J=12.30 Hz, 1H), 3.32-3.42 (m, 2H), 2.36 (br s, 1H), 2.11 (br d, J=13.05 Hz, 1H), 1.48 (br s, 9H), 1.40 (d, J=6.53 Hz, 3H); LCMS (ESI): [M+H] 325.

Compound 10.3: (2R,5'S)-5-Chloro-5'-methyl-3H-spiro[furo[2,3-c]pyridine-2,3'-pyrrolidine]: The title compound was prepared in an analogous manner of that in Compound 1.3 from tert-butyl (2R,5'S)-5-chloro-5'-methyl-3H-spiro[furo[2,3-c]pyridine-2,3'-pyrrolidine]-1'-carboxylate. LCMS (ESI): [M+H] 225.

The title compound was prepared in an analogous manner of that in Example 1 from (2R,5'S)-5-chloro-5'-methyl-3H-spiro[furo[2,3-c]pyridine-2,3'-pyrrolidine] and N-(4-fluoro-5-formyl-thiazol-2-yl)acetamide. $^1H$ NMR (400 MHz, METHANOL-$d_4$) δ 7.76 (d, J=0.75 Hz, 1H), 7.26 (d, J=0.75 Hz, 1H), 3.97 (dd, J=0.88, 14.68 Hz, 1H), 3.64 (d, J=14.81 Hz, 1H), 3.32-3.34 (m, 1H), 3.28 (s, 2H), 2.69-2.83 (m, 1H), 2.53 (d, J=10.79 Hz, 1H), 2.35 (dd, J=8.03, 14.05 Hz, 1H), 2.18 (s, 3H), 1.97-2.07 (m, 1H), 1.26 (d, J=6.02 Hz, 3H); LCMS (ESI): [M+H] 397.

Example 11: N-(5-(((2R,5'S)-5-Chloro-5'-methyl-3H-spiro[furo[2,3-c]pyridine-2,3'-pyrrolidin]-1'-yl)methyl)thiazol-2-yl)acetamide

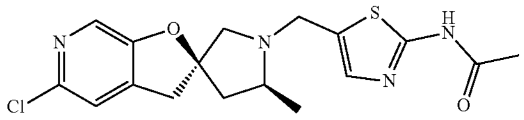 [SMILES: CC(=O)Nc1ncc(CN2C[C@@]3(Cc4cc(Cl)ncc4O3)C[C@@H]2C)s1]

The title compound was prepared in an analogous manner of that in Example 2 from (2R,5'S)-5-chloro-5'-methyl-3H-spiro[furo[2,3-c]pyridine-2,3'-pyrrolidine] and N-(5-(chloromethyl)thiazol-2-yl)acetamide. $^1H$ NMR (400 MHz, METHANOL-$d_4$) δ 7.76 (s, 1H), 7.23-7.28 (m, 2H), 4.13 (dd, J=1.00, 14.31 Hz, 1H), 3.64 (d, J=14.31 Hz, 1H), 3.25-3.29 (m, 3H), 2.69-2.82 (m, 1H), 2.49 (d, J=10.79 Hz, 1H), 2.35 (dd, J=7.78, 14.05 Hz, 1H), 2.19 (s, 3H), 1.99-2.08 (m, 1H), 1.26 (d, J=6.27 Hz, 3H); LCMS (ESI): [M+H] 379.

Example 12: N-(5-((3H-Spiro[furo[3,2-c]pyridine-2,3'-pyrrolidin]-1'-yl)methyl)-4-fluorothiazol-2-yl)acetamide

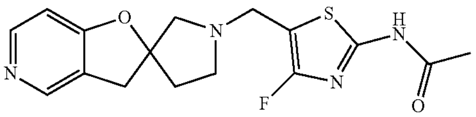

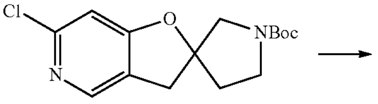

7.2

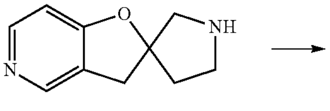

12.1

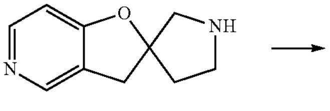

12.2

-continued

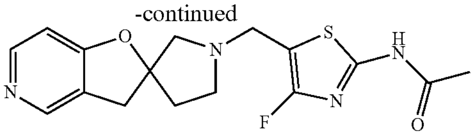

12

Compound 12.1: tert-Butyl 3H-spiro[furo[3,2-c]pyridine-2,3'-pyrrolidine]-1'-carboxylate: To a solution of tert-butyl 6-chloro-3H-spiro[furo[3,2-c]pyridine-2,3'-pyrrolidine]-1'-carboxylate (Compound 7.2, 3.2 g, 10.3 mmol) in dry MeOH (60 mL) was added 10% Pd/C (0.5 g). The mixture was backfilled with hydrogen (balloon), stirred under hydrogen (balloon) at rt overnight. The reaction mixture was then filtered. The filtrate was concentrated. The crude was purified by flash column chromatography to give the title compound (2.3 g, 81% yield) as a yellow oil. LCMS (ESI): [M+H] 277.

Compound 12.2: 3H-Spiro[furo[3,2-c]pyridine-2,3'-pyrrolidine]: The title compound was prepared in an analogous manner of that in Compound 1.3 from tert-butyl 3H-spiro[furo[3,2-c]pyridine-2,3'-pyrrolidine]-1'-carboxylate. LCMS (ESI): [M+H] 177.

The title compound was prepared in an analogous manner of that Example 2 from 3H-spiro[furo[3,2-c]pyridine-2,3'-pyrrolidine] and N-(5-(chloromethyl)-4-fluorothiazol-2-yl)acetamide. $^{1}$H NMR (400 MHz, METHANOL-$d_4$) δ 8.23 (d, J=0.75 Hz, 1H), 8.19 (d, J=5.77 Hz, 1H), 6.81 (d, J=5.77 Hz, 1H), 3.79 (d, J=1.00 Hz, 2H), 3.33-3.40 (m, 2H), 3.07 (d, J=10.79 Hz, 1H), 2.96 (td, J=7.40, 9.03 Hz, 1H), 2.74-2.86 (m, 2H), 2.33 (ddd, J=5.77, 7.40, 13.68 Hz, 1H), 2.11-2.22 (m, 4H); LCMS (ESI): [M+H] 349.

Example 13: N-(5-((3H-Spiro[furo[3,2-c]pyridine-2,3'-pyrrolidin]-1'-yl)methyl)thiazol-2-yl)acetamide

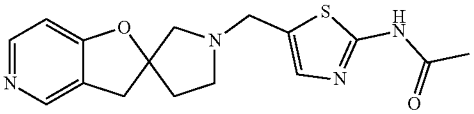 [SMILES: CC(=O)Nc1ncc(CN2CCC3(Cc4cnccc4O3)C2)s1]

The title compound was prepared in an analogous manner of that Example 2 from 3H-spiro[furo[3,2-c]pyridine-2,3'-pyrrolidine] and N-(5-(chloromethyl)thiazol-2-yl)acetamide. $^{1}$H NMR (400 MHz, METHANOL-$d_4$) δ 8.23 (d, J=0.75 Hz, 1H), 8.19 (d, J=5.77 Hz, 1H), 7.27 (s, 1H), 6.80 (d, J=5.77 Hz, 1H), 3.83-3.94 (m, 2H), 3.34 (d, J=7.78 Hz, 2H), 3.05 (d, J=11.04 Hz, 1H), 2.95 (td, J=7.37, 9.10 Hz, 1H), 2.73-2.84 (m, 2H), 2.29-2.39 (m, 1H), 2.20 (s, 3H), 2.10-2.18 (m, 1H); LCMS (ESI): [M+H] 331.

Example 14: N-(5-((3H-Spiro[furo[2,3-b]pyridine-2,3'-pyrrolidin]-1'-yl)methyl)thiazol-2-yl)acetamide

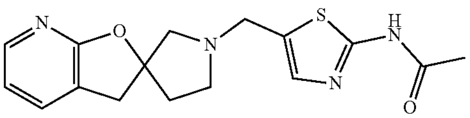 [SMILES: CC(=O)Nc1ncc(CN2CCC3(Cc4cccnc4O3)C2)s1]

The title compound was prepared in an analogous manner of that in Example 2 from 3H-spiro[furo[2,3-b]pyridine-2,3'-pyrrolidine] and N-(5-(chloromethyl)thiazol-2-yl)acetamide. $^{1}$H NMR (400 MHz, CHLOROFORM-d) δ 11.87 (br s, 1H), 7.90-8.15 (m, 1H), 7.43 (dd, J=1.51, 7.28 Hz, 1H), 7.25 (s, 1H), 6.78 (dd, J=5.14, 7.15 Hz, 1H), 3.83-4.03 (m, 2H), 3.17-3.38 (m, 2H), 2.93-3.13 (m, 3H), 2.77-2.91 (m, 1H), 2.41 (ddd, J=3.14, 7.15, 13.30 Hz, 1H), 2.32 (s, 3H), 1.98-2.14 (m, 1H); LCMS (ESI): [M+H] 331.

Example 15: N-(5-((3H-Spiro[furo[2,3-b]pyridine-2,3'-pyrrolidin]-1'-yl)methyl)-4-fluorothiazol-2-yl)acetamide

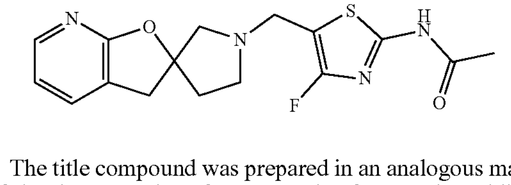

The title compound was prepared in an analogous manner of that in Example 1 from 3H-spiro[furo[2,3-b]pyridine-2,3'-pyrrolidine] and N-(4-fluoro-5-formylthiazol-2-yl)-acetamide. $^{1}$H NMR (400 MHz, METHANOL-$d_4$) δ 7.97 (br d, J=5.02 Hz, 1H), 7.69 (d, J=7.03 Hz, 1H), 6.98 (dd, J=5.27, 7.28 Hz, 1H), 4.63 (d, J=2.26 Hz, 2H), 3.75-4.00 (m, 2H), 3.42-3.72 (m, 4H), 2.34-2.64 (m, 2H), 2.22 (s, 3H); LCMS (ESI): [M+H] 349.

Example 16: N-(4-Fluoro-5-(((2R,5'S)-5-methoxy-5'-methyl-3H-spiro[furo[2,3-c]pyridine-2,3'-pyrrolidin]-1'-yl)methyl)thiazol-2-yl)acetamide

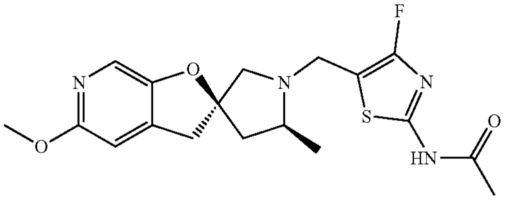 [SMILES: COc1cc2c(cn1)O[C@]1(C2)C[C@H](C)N(Cc2sc(NC(C)=O)nc2F)C1]

The title compound was prepared in an analogous manner of that in Example 9 from 5-bromo-2-methoxy-4-methylpyridine, tert-butyl (S)-2-methyl-4-oxopyrrolidine-1-carboxylate and N-(4-fluoro-5-formyl-thiazol-2-yl)acetamide. $^{1}$H NMR (400 MHz, METHANOL-$d_4$) δ 7.48 (d, J=0.75 Hz, 1H), 6.65 (d, J=0.75 Hz, 1H), 3.96 (dd, J=0.88, 14.68 Hz, 1H), 3.80 (s, 3H), 3.64 (d, J=14.56 Hz, 1H), 3.27 (d, J=10.79 Hz, 1H), 3.19 (d, J=0.75 Hz, 2H), 2.68-2.80 (m, 1H), 2.50 (d, J=10.54 Hz, 1H), 2.32 (dd, J=7.91, 13.93 Hz, 1H), 2.18 (s, 3H), 1.99 (ddd, J=1.25, 8.28, 13.80 Hz, 1H), 1.25 (d, J=6.02 Hz, 3H); LCMS (ESI): [M+H] 393.

Example 17: N-(5-(((2R,5'S)-5-Methoxy-5'-methyl-3H-spiro[furo[2,3-c]pyridine-2,3'-pyrrolidin]-1'-yl)methyl)thiazol-2-yl)acetamide

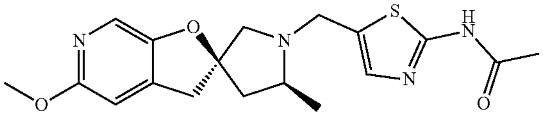 [SMILES: COc1cc2c(cn1)O[C@]1(C2)C[C@H](C)N(Cc2cnc(NC(C)=O)s2)C1]

The title compound was prepared in an analogous manner of that in Example 2 from (2R,5'S)-5-methoxy-5'-methyl-3H-spiro[furo[2,3-c]pyridine-2,3'-pyrrolidine] and N-(4-fluoro-5-formyl-thiazol-2-yl)acetamide. $^1$H NMR (400 MHz, METHANOL-$d_4$) δ 7.47 (d, J=0.75 Hz, 1H), 7.26 (s, 1H), 6.64 (d, J=1.00 Hz, 1H), 4.13 (d, J=14.31 Hz, 1H), 3.80 (s, 3H), 3.64 (d, J=14.31 Hz, 1H), 3.25 (d, J=11.29 Hz, 1H), 3.19 (d, J=1.00 Hz, 2H), 2.67-2.81 (m, 1H), 2.47 (d, J=10.79 Hz, 1H), 2.32 (dd, J=7.91, 13.93 Hz, 1H), 2.20 (s, 3H), 2.00 (ddd, J=1.25, 8.47, 13.87 Hz, 1H), 1.26 (d, J=6.27 Hz, 3H); LCMS (ESI): [M+H] 375.

Example 18: N-(4-Fluoro-5-(((2R,5'S)-4-methoxy-5'-methyl-3H-spiro[furo[3,2-c]pyridine-2,3'-pyrrolidin]-1'-yl)methyl)thiazol-2-yl)acetamide

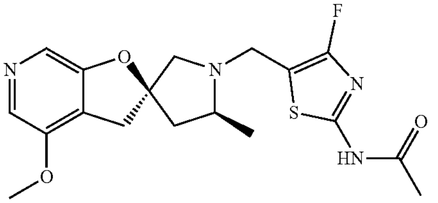

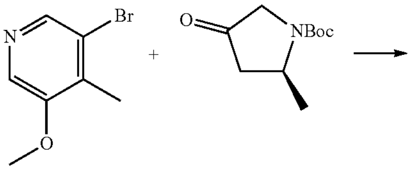

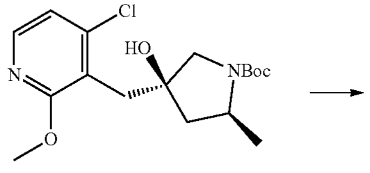

18.1

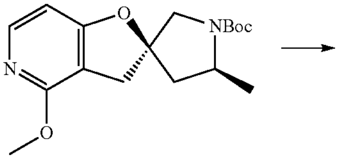

18.2

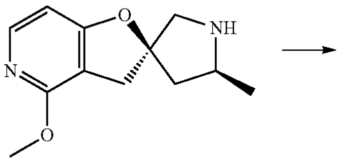

18.2

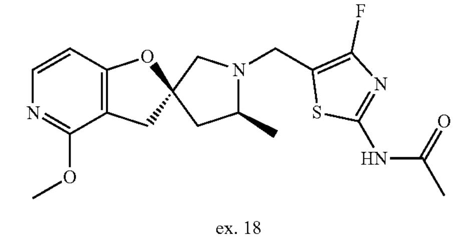

ex. 18

Compound 18.1: tert-Butyl (2S,4R)-4-((4-chloro-2-methoxypyridin-3-yl)methyl)-4-hydroxy-2-methylpyrrolidine-1-carboxylate: The title compound was prepared in an analogous manner of that in Compound 10.1 from 4-chloro-2-methoxy-3-methylpyridine and tert-butyl (S)-2-methyl-4-oxopyrrolidine-1-carboxylate. 39% yield. LCMS (ESI): [M-tBu)] 301.

Compound 18.2: tert-Butyl (2R,5'S)-4-methoxy-5'-methyl-3H-spiro[furo[3,2-c]pyridine-2,3'-pyrrolidine]-1'-carboxylate: A solution of tert-butyl (2S)-4-[(4-chloro-2-methoxy-3-pyridyl)methyl]-4-hydroxy-2-methyl-pyrrolidine-1-carboxylate (120 mg, 336 umol) in DMSO (2.0 mL) was cooled to 0° C., potassium tert-butoxide (113 mg, 1.01 mmol) was then added, and then stirred at rt overnight. The reaction was quenched with aq. $NH_4Cl$, extracted with EtOAc. The organic layer was then separated, dried and concentrated. The crude was purified by chromatography on silica gel (0-100% EtOAc in heptane) to give the title compound (53 mg, 24% yield). LCMS (ESI): [M+H] 321.

Compound 18.3: (2R,5'S)-4-Methoxy-5'-methyl-3H-spiro[furo[3,2-c]pyridine-2,3'-pyrrolidine]: The title compound was prepared in an analogous manner of that in Compound 1.3 from tert-butyl (2R,5'S)-4-methoxy-5'-methyl-3H-spiro[furo[3,2-c]pyridine-2,3'-pyrrolidine]-1'-carboxylate. 97% yield. LCMS (ESI): [M+H] 221.

The title compound was prepared in an analogous manner of that in Example 1 from (2R,5'S)-4-methoxy-5'-methyl-3H-spiro[furo[3,2-c]pyridine-2,3'-pyrrolidine] and N-(4-fluoro-5-formylthiazol-2-yl)acetamide. $^1$H NMR (400 MHz, METHANOL-$d_4$) δ 7.84 (d, J=6.27 Hz, 1H), 6.56-6.67 (m, 1H), 5.53 (br s, 1H), 4.56-4.71 (m, 1H), 4.39-4.54 (m, 2H), 4.12-4.23 (m, 1H), 4.01-4.09 (m, 1H), 3.93-4.00 (m, 3H), 3.36-3.52 (m, 2H), 2.18-2.26 (m, 3H), 1.50-1.70 (m, 1H), 1.43 (d, J=6.78 Hz, 3H), 1.32 (br dd, J=2.51, 7.78 Hz, 1H); LCMS (ESI): [M+H] 393.

Example 19: N-(4-Fluoro-5-(((2S,5'S)-5'-methyl-3H-spiro[furo[3,2-b]pyridine-2,3'-pyrrolidin]-1'-yl)methyl)thiazol-2-yl)acetamide

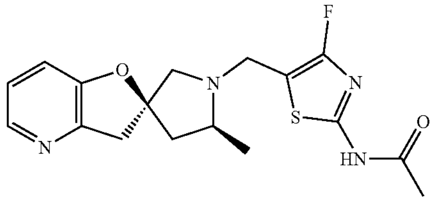

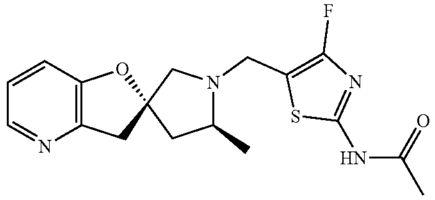

The title compound was prepared in an analogous manner of that in Example 9 from 3-bromo-2-methylpyridine, tert-butyl (S)-2-methyl-4-oxopyrrolidine-1-carboxylate and N-(4-fluoro-5-formylthiazol-2-yl)acetamide. Two diastereomers were isolated after chromatography on silica gel (0-80% EtOAc-EtOH 3:1 with 2% $NH_4OH$ in heptane). The chiral center on the quaternary carbon was randomly assigned. P1: $^1$H NMR (400 MHz, METHANOL-$d_4$) δ 7.93 (dd, J=1.88, 4.64 Hz, 1H), 7.08-7.17 (m, 2H), 3.98 (dd, J=0.75, 14.56 Hz, 1H), 3.65 (d, J=14.81 Hz, 1H), 3.33 (s, 1H), 3.30 (br s, 2H), 2.71-2.87 (m, 1H), 2.57 (d, J=10.79 Hz, 1H), 2.39 (dd, J=8.03, 14.05 Hz, 1H), 2.18 (s, 3H), 1.97-2.09 (m, 1H), 1.27 (d, J=6.27 Hz, 3H); LCMS (ESI): [M+H] 363. P2: $^1$H NMR (400 MHz, METHANOL-$d_4$) δ 7.93 (dd, J=1.38, 4.89 Hz, 1H), 7.05-7.18 (m, 2H), 3.99 (d, J=14.56 Hz, 1H), 3.73 (d, J=14.56 Hz, 1H), 3.35-3.44 (m, 1H), 3.23-3.30 (m, 2H), 2.83-3.11 (m, 2H), 2.41 (dd, J=6.15, 13.43 Hz, 1H), 2.19 (s, 3H), 1.76 (dd, J=9.91, 13.43 Hz, 1H), 1.23 (d, J=6.02 Hz, 3H); LCMS (ESI): [M+H] 363.

Example 20: N-(4-Fluoro-5-(((2S,5'S)-5-methoxy-5'-methyl-3H-spiro[furo[3,2-b]pyridine-2,3'-pyrrolidin]-1'-yl)methyl)thiazol-2-yl)acetamide

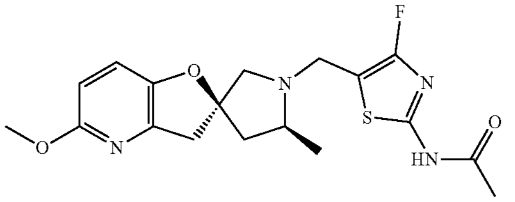 [SMILES: COc1ccc2c(n1)C[C@]1(C[C@H](C)N(Cc3sc(NC(C)=O)nc3F)C1)O2]

The title compound was prepared in an analogous manner of that in Example 10 from 3-bromo-6-methoxy-2-methylpyridine, tert-butyl (S)-2-methyl-4-oxopyrrolidine-1-carboxylate and N-(4-fluoro-5-formylthiazol-2-yl)acetamide. $^1$H NMR (400 MHz, METHANOL-$d_4$) δ 7.07 (d, J=8.78 Hz, 1H), 6.53 (d, J=8.53 Hz, 1H), 4.59 (br d, J=7.28 Hz, 1H), 4.08-4.26 (m, 1H), 3.79-3.99 (m, 4H), 3.39-3.55 (m, 1H), 3.25 (s, 2H), 2.79 (br s, 1H), 2.50 (br d, J=9.29 Hz, 1H), 2.19 (s, 3H), 2.05-2.16 (m, 1H), 1.36 (br d, J=5.77 Hz, 3H). LCMS (ESI): [M+H] 393.

Example 21: N-(4-Fluoro-5-(((2R,5'S)-5'-methyl-5-(trifluoromethyl)-3H-spiro[furo[2,3-c]pyridine-2,3'-pyrrolidin]-1'-yl)methyl)thiazol-2-yl)acetamide

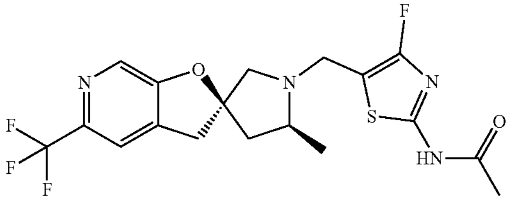 [SMILES: CC(=O)Nc1nc(F)c(CN2C[C@@]3(Cc4cc(C(F)(F)F)ncc4O3)C[C@@H]2C)s1]

The title compound was prepared in an analogous manner of that in Example 10 from 5-bromo-4-methyl-2-(trifluoromethyl)pyridine, tert-butyl (S)-2-methyl-4-oxopyrrolidine-1-carboxylate and N-(4-fluoro-5-formylthiazol-2-yl)acetamide. $^1$H NMR (400 MHz, METHANOL-$d_4$) δ 8.10 (s, 1H), 7.65 (d, J=0.75 Hz, 1H), 3.98 (dd, J=0.88, 14.68 Hz, 1H), 3.65 (d, J=14.56 Hz, 1H), 3.36 (s, 2H), 2.71-2.85 (m, 1H), 2.56 (d, J=10.79 Hz, 1H), 2.38 (dd, J=8.03, 14.05 Hz, 1H), 2.18 (s, 3H), 2.05 (ddd, J=1.25, 8.28, 14.05 Hz, 1H), 1.27 (d, J=6.02 Hz, 3H); LCMS (ESI): [M+H] 431.

Example 22: N-(5-(((2R,5'S)-5'-Methyl-5-(trifluoromethyl)-3H-spiro[furo[2,3-c]pyridine-2,3'-pyrrolidin]-1'-yl)methyl)thiazol-2-yl)acetamide

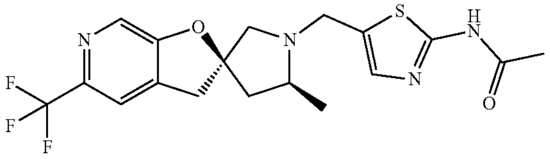 [SMILES: CC(=O)Nc1ncc(CN2C[C@@]3(Cc4cc(C(F)(F)F)ncc4O3)C[C@@H]2C)s1]

The title compound was prepared in an analogous manner of that in Example 2 from (2R,5'S)-5'-methyl-5-(trifluoromethyl)-3H-spiro[furo[2,3-c]pyridine-2,3'-pyrrolidine] and N-(5-(chloromethyl)thiazol-2-yl)acetamide. $^1$H NMR (400 MHz, METHANOL-$d_4$) δ 8.09 (s, 1H), 7.65 (d, J=0.75 Hz, 1H), 7.27 (s, 1H), 4.14 (dd, J=1.00, 14.31 Hz, 1H), 3.65 (d, J=14.31 Hz, 1H), 3.35 (s, 2H), 3.33 (s, 1H), 2.72-2.84 (m, 1H), 2.52 (d, J=11.04 Hz, 1H), 2.38 (dd, J=7.78, 14.05 Hz, 1H), 2.19 (s, 3H), 2.06 (ddd, J=1.38, 8.34, 14.12 Hz, 1H), 1.27 (d, J=6.27 Hz, 3H); LCMS (ESI): [M+H] 413.

Example 23: N-(5-(((2R,5'S)-5,5'-Dimethyl-3H-spiro[furo[2,3-c]pyridine-2,3'-pyrrolidin]-1'-yl)methyl)-4-fluorothiazol-2-yl)acetamide

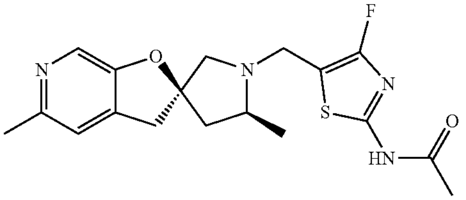

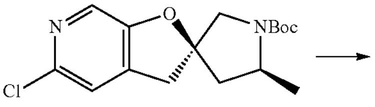

10.2

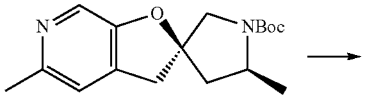

23.1

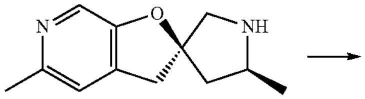

23.2

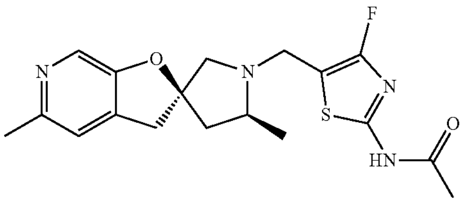

23

Compound 23.1: tert-Butyl (2R,5'S)-5,5'-dimethyl-3H-spiro[furo[2,3-c]pyridine-2,3'-pyrrolidine]-1'-carboxylate: A mixture of tert-butyl (2R,5'S)-5-chloro-5'-methyl-3H- spiro[furo[2,3-c]pyridine-2,3'-pyrrolidine]-1'-carboxylate (Compound 10.2, 100 mg, 307.88 umol), 2,4,6-trimethyl-1,3,5,2,4,6-trioxatriborinane (386 mg, 3.08 mmol), $K_2CO_3$ (2M, aqueous, 308 uL) and Pd(dppf)$Cl_2$ DCM (30.79 umol) in DME (2.0 mL) was purged with nitrogen and heated in a microwave at 120° C. for 20 min. The reaction mixture was diluted with EtOAc, washed with brine. The organic layer was separated, dried and concentrated. The crude was purified by chromatography on silica gel (0-100% EtOAc in heptane) to give the title compound (45 mg, 48% yield). $^1$H NMR (400 MHz, METHANOL-$d_4$) δ 7.86 (s, 1H), 7.17 (s, 1H), 4.02-4.11 (m, 1H), 3.72 (br d, J=12.05 Hz, 1H), 3.52 (d, J=12.30 Hz, 1H), 3.31-3.37 (m, 1H), 3.21-3.28 (m, 1H), 2.44 (s, 3H), 2.35 (br d, J=7.53 Hz, 1H), 2.08 (br d, J=12.55 Hz, 1H), 1.48 (br s, 9H), 1.41 (d, J=6.27 Hz, 3H); LCMS (ESI): [M+H] 305.

Compound 23.2: (2R,5'S)-5,5'-Dimethyl-3H-spiro[furo[2,3-c]pyridine-2,3'-pyrrolidine]: The title compound was prepared in an analogous manner of that in Compound 1.3 from tert-butyl (2R,5'S)-5,5'-dimethyl-3H-spiro[furo[2,3-c]pyridine-2,3'-pyrrolidine]-1'-carboxylate. LCMS (ESI): [M+H] 205.

The title compound was prepared in an analogous manner of that in Example 1 from (2R,5'S)-5,5'-dimethyl-3H-spiro[furo[2,3-c]pyridine-2,3'-pyrrolidine] and N-(4-fluoro-5-formylthiazol-2-yl)acetamide. $^1$H NMR (400 MHz, METHANOL-$d_4$) δ 8.17 (s, 1H), 7.72 (s, 1H), 4.72 (d, J=14.81 Hz, 1H), 4.51 (d, J=14.81 Hz, 1H), 3.89-4.05 (m, 2H), 3.71 (s, 2H), 3.58 (d, J=12.55 Hz, 1H), 2.86 (dd, J=9.54, 14.81 Hz, 1H), 2.67 (s, 3H), 2.41 (ddd, J=1.88, 6.15, 14.81 Hz, 1H), 2.21 (s, 3H), 1.59 (d, J=6.78 Hz, 3H); LCMS (ESI): [M+H] 377.

Example 24: N-(5-(((2R,5'S)-5-Cyclopropyl-5'-methyl-3H-spiro[furo[2,3-c]pyridine-2,3'-pyrrolidin]-1'-yl)methyl)-4-fluorothiazol-2-yl)acetamide

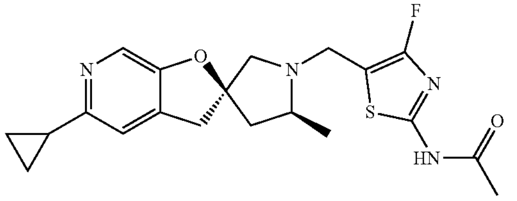

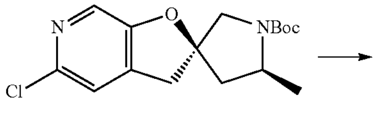

10.2

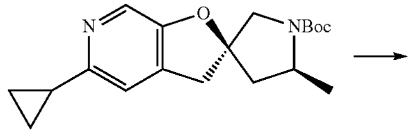

24.1

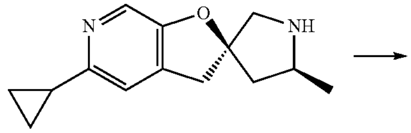

24.2

-continued

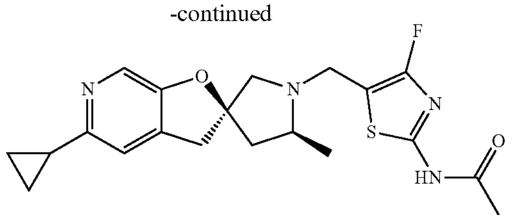

24

Compound 24.1: tert-Butyl (2R,5'S)-5-cyclopropyl-5'-methyl-3H-spiro[furo[2,3-c]pyridine-2,3'-pyrrolidine]-1'-carboxylate: A mixture of tert-butyl (2R,5'S)-5-chloro-5'-methyl-3H-spiro[furo[2,3-c]pyridine-2,3'-pyrrolidine]-1'-carboxylate (Compound 10.2, 200 mg, 615.76 umol), potassium cyclopropyl-(trifluoro)-boranuide (182 mg, 1.23 mmol), aqueous $Cs_2CO_3$ (2M, 616 uL) and 4-ditert-butylphosphanyl-N,N-dimethyl-aniline; dichloropalladium (44 mg, 61.58 umol) in dioxane (5.0 mL) was purged with nitrogen and heated at 110° C. overnight. Diluted with EtOAc, washed with water (3×), then brine. The organic layer was then separated, dried and concentrated. The crude was purified by HPLC to give the title compound (128 mg, 47% yield). LCMS (ESI): [M+H] 331.

Compound 24.2: (2R,5'S)-5-Cyclopropyl-5'-methyl-3H-spiro[furo[2,3-c]pyridine-2,3'-pyrrolidine]: The title compound was prepared in an analogous manner of that in Compound 1.3 from tert-butyl (2R,5'S)-5-cyclopropyl-5'-methyl-3H-spiro[furo[2,3-c]pyridine-2,3'-pyrrolidine]-1'-carboxylate. LCMS (ESI): [M+H] 231.

The title compound was prepared in an analogous manner of that in Example 1 from (2R,5'S)-5-cyclopropyl-5'-methyl-3H-spiro[furo[2,3-c]pyridine-2,3'-pyrrolidine] and N-(4-fluoro-5-formylthiazol-2-yl)acetamide. $^1$H NMR (400 MHz, METHANOL-$d_4$) δ 8.08 (s, 1H), 7.49 (s, 1H), 4.72 (d, J=14.81 Hz, 1H), 4.52 (d, J=14.81 Hz, 1H), 3.89-4.04 (m, 2H), 3.67 (s, 2H), 3.58 (d, J=12.55 Hz, 1H), 2.86 (dd, J=9.79, 14.81 Hz, 1H), 2.40 (ddd, J=1.88, 6.09, 14.87 Hz, 1H), 2.27 (tt, J=4.96, 8.34 Hz, 1H), 2.21 (s, 3H), 1.59 (d, J=6.78 Hz, 3H), 1.30-1.39 (m, 2H), 1.06-1.13 (m, 2H); LCMS (ESI): [M+H] 403.

Example 25: N-(5-(((2R,5'S)-5-Cyclopropyl-5'-methyl-3H-spiro[furo[2,3-c]pyridine-2,3'-pyrrolidin]-1'-yl)methyl)thiazol-2-yl)acetamide

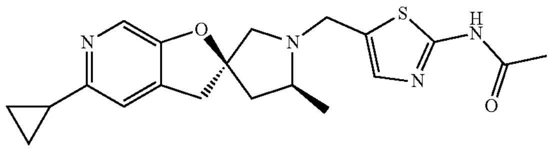 [SMILES: CC(=O)Nc1ncc(CN2C[C@@]3(Cc4cc(C5CC5)ncc4O3)C[C@@H]2C)s1]

The title compound was prepared in an analogous manner of that in Example 2 from (2R,5'S)-5-cyclopropyl-5'-methyl-3H-spiro[furo[2,3-c]pyridine-2,3'-pyrrolidine] and N-(5-(chloromethyl)thiazol-2-yl)acetamide. $^1$H NMR (400 MHz, METHANOL-$d_4$) δ 8.08 (s, 1H), 7.64 (s, 1H), 7.48 (s, 1H), 4.84 (s, 1H), 4.60 (d, J=14.05 Hz, 1H), 3.99 (td, J=6.56, 9.47 Hz, 1H), 3.90 (dd, J=1.76, 12.80 Hz, 1H), 3.66 (s, 2H), 3.59 (d, J=12.80 Hz, 1H), 2.84 (dd, J=9.54, 14.81 Hz, 1H), 2.40 (br dd, J=4.02, 14.56 Hz, 1H), 2.19-2.31 (m, 4H), 1.57 (d, J=6.78 Hz, 3H), 1.29-1.37 (m, 2H), 1.04-1.13 (m, 2H); LCMS (ESI): [M+H] 385.

Example 26: N-(5-(((2R,5'S)-5-(Difluoromethyl)-5'-methyl-3H-spiro[furo[2,3-c]pyridine-2,3'-pyrrolidin]-1'-yl)methyl)-4-fluorothiazol-2-yl)acetamide

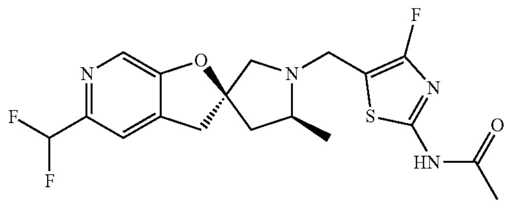

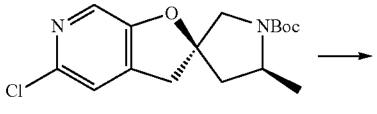

10.2

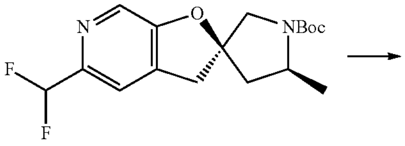

26.1

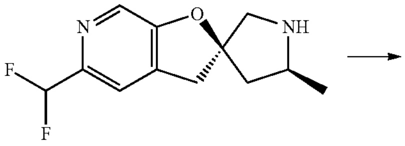

26.2

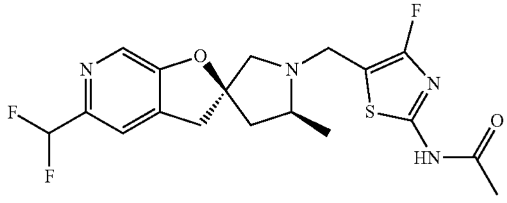

26

Compound 26.1: tert-Butyl (2R,5'S)-5-(difluoromethyl)-5'-methyl-3H-spiro[furo[2,3-c]pyridine-2,3'-pyrrolidine]-1'-carboxylate: A mixture of tert-butyl (2R,5'S)-5-chloro-5'-methyl-3H-spiro[furo[2,3-c]pyridine-2,3'-pyrrolidine]-1'-carboxylate (Compound 10.2, 200 mg, 615.76 umol), [1,3-bis[2,6-bis(1-methylethyl)phenyl]-2-imidazolidinylidene](difluoromethyl) silver (428 mg 800.49 umol), tris(dibenzylideneacetone) dipalladium (28 mg, 30.79 umol), DPEPhos (33 mg, 61.58 umol) in toluene (8.0 mL) was purged with nitrogen, then heated in a sealed vial at 80° C. overnight. Filter off the solid, the filtration was concentrated and purified by chromatography on silica gel (0-50% EtOAc in heptane) to give the title compound (82 mg, 35% yield). $^1$H NMR (400 MHz, METHANOL-$d_4$) δ 8.08 (s, 1H), 7.59 (s, 1H), 6.46-6.81 (m, 1H), 4.05-4.16 (m, 1H), 3.78 (br d, J=12.55 Hz, 1H), 3.56 (d, J=12.30 Hz, 1H), 3.39-3.47 (m, 1H), 3.38 (s, 2H), 2.38 (br s, 1H), 2.13 (br d, J=12.80 Hz, 1H), 1.48 (br s, 9H), 1.42 (d, J=6.53 Hz, 3H); LCMS (ESI): [M+H] 341.

Compound 26.2: (2R,5'S)-5-(Difluoromethyl)-5'-methyl-3H-spiro[furo[2,3-c]pyridine-2,3'-pyrrolidine]: The title compound was prepared in an analogous manner of that in Compound 1.3 from tert-butyl (2R,5'S)-5-(difluoromethyl)-5'-methyl-3H-spiro[furo[2,3-c]pyridine-2,3'-pyrrolidine]-1'-carboxylate. LCMS (ESI): [M+H] 241.

The title compound was prepared in an analogous manner of that in Example 1 from (2R,5'S)-5-(difluoromethyl)-5'-methyl-3H-spiro[furo[2,3-c]pyridine-2,3'-pyrrolidine] and N-(4-fluoro-5-formylthiazol-2-yl)acetamide. $^1$H NMR (400 MHz, METHANOL-$d_4$) δ 8.03 (s, 1H), 7.54 (s, 1H), 6.44-6.80 (m, 1H), 3.98 (dd, J=0.88, 14.68 Hz, 1H), 3.66 (d, J=14.56 Hz, 1H), 3.33-3.36 (m, 3H), 2.72-2.83 (m, 1H), 2.56 (d, J=10.79 Hz, 1H), 2.37 (dd, J=7.91, 13.93 Hz, 1H), 2.18 (s, 3H), 2.04 (ddd, J=1.51, 8.28, 14.05 Hz, 1H), 1.27 (d, J=6.02 Hz, 3H); LCMS (ESI): [M+H] 413.

Example 27: N-(5-(((2R,5'S)-5-(Difluoromethyl)-5'-methyl-3H-spiro[furo[2,3-c]pyridine-2,3'-pyrrolidin]-1'-yl)methyl)thiazol-2-yl)acetamide

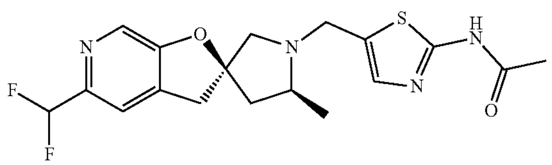 [SMILES: CC(=O)Nc1ncc(CN2C[C@@]3(Cc4cc(C(F)F)ncc4O3)C[C@@H]2C)s1]

The title compound was prepared in an analogous manner of that in Example 2 from (2R,5'S)-5-(difluoromethyl)-5'-methyl-3H-spiro[furo[2,3-c]pyridine-2,3'-pyrrolidine] and N-(5-(chloromethyl)thiazol-2-yl)acetamide. $^1$H NMR (400 MHz, METHANOL-$d_4$) δ 8.03 (s, 1H), 7.54 (s, 1H), 7.27 (s, 1H), 6.44-6.78 (m, 1H), 4.14 (dd, J=0.75, 14.31 Hz, 1H), 3.65 (d, J=14.31 Hz, 1H), 3.33 (s, 2H), 3.28 (br d, J=1.00 Hz, 1H), 2.73-2.84 (m, 1H), 2.52 (d, J=10.79 Hz, 1H), 2.37 (dd, J=7.91, 13.93 Hz, 1H), 2.19 (s, 3H), 2.01-2.10 (m, 1H), 1.27 (d, J=6.02 Hz, 3H); LCMS (ESI): [M+H] 395.

Example 28: N-(5-(((2R,5'S)-5-(Dimethylamino)-5'-methyl-3H-spiro[furo[2,3-c]pyridine-2,3'-pyrrolidin]-1'-yl)methyl)-4-fluorothiazol-2-yl)acetamide

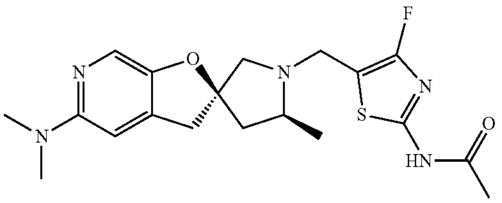

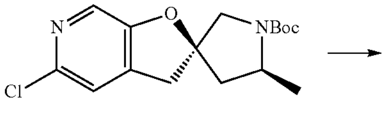

10.2

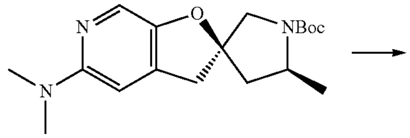

28.1

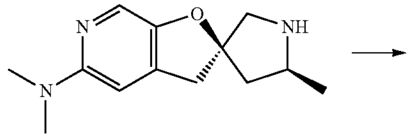

28.2

-continued

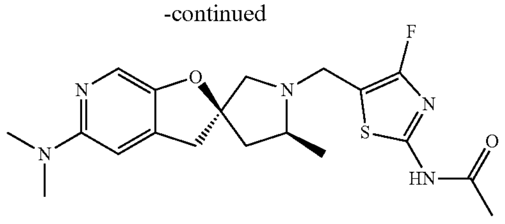

28

Compound 28.1: tert-Butyl (2R,5'S)-5-(dimethylamino)-5'-methyl-3H-spiro[furo[2,3-c]pyridine-2,3'-pyrrolidine]-1'-carboxylate: A mixture of tert-butyl (2R,5'S)-5-chloro-5'-methyl-3H-spiro[furo[2,3-c]pyridine-2,3'-pyrrolidine]-1'-carboxylate (Compound 10.2, 70 mg, 215.52 umol), sodium tert-butoxide (41 mg, 431.04 umol), [1-(2-diphenylphosphanyl-1-naphthyl)-2-naphthyl]-diphenyl-phosphane (13 mg, 21.55 umol) and $Pd_2$ $(dba)_3$ (10 mg, 10.78 umol) in toluene (2.0 mL) was purged with nitrogen, dimethylamine (2 M in THF, 539 uL) was added and the reaction was heated in a sealed vial at 110° C. overnight. Filter off the solid, the filtrate was concentrated and purified by chromatography on silica gel (0-80% EtOAc-EtOH 3:1 with 2% $NH_4OH$ in heptane) to give the title compound (51 mg, 71% yield). $^1H$ NMR (400 MHz, METHANOL-$d_4$) δ 7.49 (s, 1H), 6.78 (s, 1H), 4.08 (td, J=7.00, 9.60 Hz, 1H), 3.69 (br d, J=12.30 Hz, 1H), 3.51 (d, J=12.05 Hz, 1H), 3.18-3.29 (m, 2H), 3.05 (s, 6H), 2.28-2.43 (m, 1H), 2.02-2.10 (m, 1H), 1.48 (br s, 9H), 1.40 (d, J=6.53 Hz, 3H); LCMS (ESI): [M+H] 334.

Compound 28.2: (2R,5'S)—N,N,5'-Trimethyl-3H-spiro[furo[2,3-c]pyridine-2,3'-pyrrolidin]-5-amine: The title compound was prepared in an analogous manner of that in Compound 1.3 from tert-butyl (2R,5'S)-5-(dimethylamino)-5'-methyl-3H-spiro[furo[2,3-c]pyridine-2,3'-pyrrolidine]-1'-carboxylate. LCMS (ESI): [M+H] 234.

The title compound was prepared in an analogous manner of that in Example 1 from (2R,5'S)—N,N,5'-trimethyl-3H-spiro[furo[2,3-c]pyridine-2,3'-pyrrolidin]-5-amine and N-(4-fluoro-5-formylthiazol-2-yl)acetamide. $^1H$ NMR (400 MHz, METHANOL-$d_4$) δ 7.38 (s, 1H), 7.21 (s, 1H), 4.69 (br d, J=14.30 Hz, 1H), 4.49 (br d, J=14.56 Hz, 1H), 3.89 (br d, J=12.05 Hz, 2H), 3.50-3.64 (m, 3H), 3.19-3.27 (m, 6H), 2.73-2.90 (m, 1H), 2.32 (br d, J=9.79 Hz, 1H), 2.21 (s, 3H), 1.58 (d, J=6.53 Hz, 3H); LCMS (ESI): [M+H] 406.

Example 29: N-(4-Fluoro-5-(((2R,5'S)-5'-methyl-5-(methylamino)-3H-spiro[furo[2,3-c]pyridine-2,3'-pyrrolidin]-1'-yl)methyl)thiazol-2-yl)acetamide

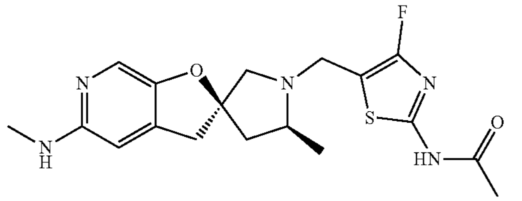 [SMILES: CNc1cc2c(cn1)O[C@]1(C2)C[C@H](C)N(Cc2sc(NC(C)=O)nc2F)C1]

The title compound was prepared in an analogous manner of that in Example 28 from methylamine, tert-butyl (2R,5'S)-5-chloro-5'-methyl-3H-spiro[furo[2,3-c]pyridine-2,3'-pyrrolidine]-1'-carboxylate (Compound 10.2) and N-(4-fluoro-5-formylthiazol-2-yl)acetamide. $^1H$ NMR (400 MHz, METHANOL-$d_4$) δ 7.32 (s, 1H), 6.96 (s, 1H), 4.70 (d, J=14.56 Hz, 1H), 4.51 (d, J=14.81 Hz, 1H), 3.87-4.01 (m, 2H), 3.49-3.58 (m, 3H), 2.98 (s, 3H), 2.82 (dd, J=9.66, 14.68 Hz, 1H), 2.32 (br dd, J=4.27, 14.81 Hz, 1H), 2.21 (s, 3H), 1.58 (d, J=6.78 Hz, 3H); LCMS (ESI): [M+H] 392.

Example 30: N-(4-Fluoro-5-(((2R,5'S)-5-(isopropylamino)-5'-methyl-3H-spiro[furo[2,3-c]pyridine-2,3'-pyrrolidin]-1'-yl)methyl)thiazol-2-yl)acetamide

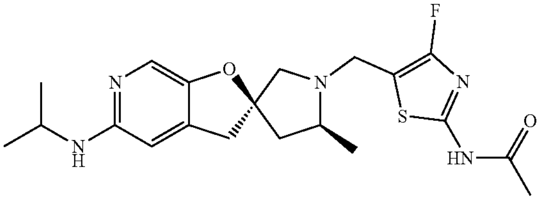 [SMILES: CC(=O)Nc1nc(F)c(CN2C[C@@]3(Cc4cc(NC(C)C)ncc4O3)C[C@@H]2C)s1]

The title compound was prepared in an analogous manner of that in Example 28 from isopropylamine, tert-butyl (2R,5'S)-5-chloro-5'-methyl-3H-spiro[furo[2,3-c]pyridine-2,3'-pyrrolidine]-1'-carboxylate (Compound 10.2) and N-(4-fluoro-5-formylthiazol-2-yl)acetamide. $^1H$ NMR (400 MHz, METHANOL-$d_4$) δ 7.29 (d, J=0.75 Hz, 1H), 6.94 (d, J=0.75 Hz, 1H), 4.71 (d, J=14.81 Hz, 1H), 4.52 (d, J=14.81 Hz, 1H), 3.88-4.00 (m, 2H), 3.81 (quin, J=6.34 Hz, 1H), 3.50-3.59 (m, 3H), 2.76-2.88 (m, 1H), 2.28-2.36 (m, 1H), 2.21 (s, 3H), 1.58 (d, J=6.78 Hz, 3H), 1.29 (dd, J=1.13, 6.40 Hz, 6H); LCMS (ESI): [M+H] 420.

Example 31: N-(5-(((2R,5'S)-5-(Cyclopropylamino)-5'-methyl-3H-spiro[furo[2,3-c]pyridine-2,3'-pyrrolidin]-1'-yl)methyl)-4-fluorothiazol-2-yl)acetamide

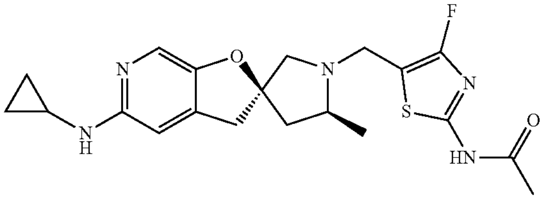

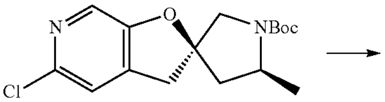

10.2

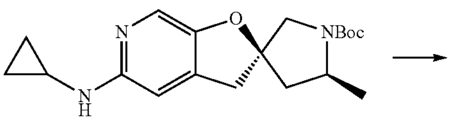

31.1

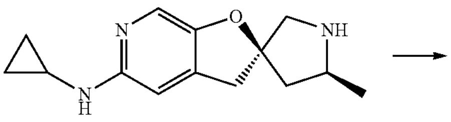

31.2

-continued

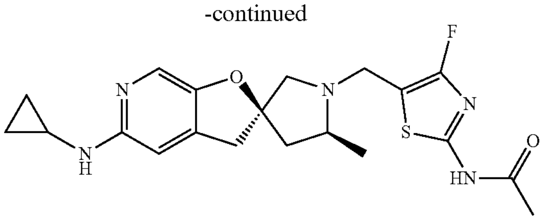

31

Compound 31.1: tert-Butyl (2R,5'S)-5-(cyclopropylamino)-5'-methyl-3H-spiro[furo[2,3-c]pyridine-2,3'-pyrrolidine]-1'-carboxylate: The title compound was prepared in an analogous manner of that in Example 28 from cyclopropanamine and tert-butyl (2R,5'S)-5-chloro-5'-methyl-3H-spiro[furo[2,3-c]pyridine-2,3'-pyrrolidine]-1'-carboxylate (Compound 10.2). $^{1}$H NMR (400 MHz, METHANOL-$d_4$) δ 7.44 (s, 1H), 6.71 (d, J=0.75 Hz, 1H), 3.97-4.17 (m, 1H), 3.68 (br d, J=12.05 Hz, 1H), 3.49 (d, J=12.30 Hz, 1H), 3.11-3.27 (m, 2H), 2.45 (tt, J=3.42, 6.74 Hz, 1H), 2.24-2.37 (m, 1H), 1.97-2.11 (m, 1H), 1.48 (br s, 9H), 1.40 (d, J=6.27 Hz, 3H), 0.69-0.78 (m, 2H), 0.42-0.50 (m, 2H); LCMS (ESI): [M+H] 346.

Compound 31.2: (2R,5'S)—N-Cyclopropyl-5'-methyl-3H-spiro[furo[2,3-c]pyridine-2,3'-pyrrolidin]-5-amine: To a solution of tert-butyl (2R,5'S)-5-(cyclopropylamino)-5'-methyl-3H-spiro[furo[2,3-c]pyridine-2,3'-pyrrolidine]-1'-carboxylate (45 mg, 130.27 umol) in DCM (1.0 mL) was added HCl (4 M in dioxane, 326 uL). The mixture was stirred at rt overnight. Remove all the solvent, the crude was triturated with ether, then dried to give the title compound (36 mg, 98% yield, HCl salt). LCMS (ESI): [M+H] 246.

To a mixture of (2R,5'S)—N-cyclopropyl-5'-methyl-3H-spiro[furo[2,3-c]pyridine-2,3'-pyrrolidin]-5-amine (35 mg, 124.21 umol. HCl salt) and N-[5-(chloromethyl)-4-fluoro-thiazol-2-yl]acetamide (39 mg, 186.31 umol) in acetonitrile (1.00 mL) was added triethylamine (497 umol, 69 uL). The reaction was stirred at rt overnight. Remove all the solvent, the crude was purified by HPLC to give the title compound (3.3 mg, 6% yield) as a white powder. $^{1}$H NMR (400 MHz, METHANOL-$d_4$) δ 7.38 (d, J=0.75 Hz, 1H), 6.98 (s, 1H), 4.71 (d, J=14.81 Hz, 1H), 4.52 (d, J=14.56 Hz, 1H), 3.86-4.02 (m, 2H), 3.49-3.62 (m, 3H), 2.77-2.86 (m, 1H), 2.61 (tt, J=3.45, 6.84 Hz, 1H), 2.33 (ddd, J=1.88, 6.02, 14.68 Hz, 1H), 2.21 (s, 3H), 1.58 (d, J=6.78 Hz, 3H), 0.94-1.03 (m, 2H), 0.63-0.71 (m, 2H); LCMS (ESI): [M+H] 418.

Example 32: N-(5-(((2R,5'S)-5-((2-Methoxyethyl)(methyl)amino)-5'-methyl-3H-spiro[furo[2,3-c]pyridine-2,3'-pyrrolidin]-1'-yl)methyl)thiazol-2-yl)acetamide

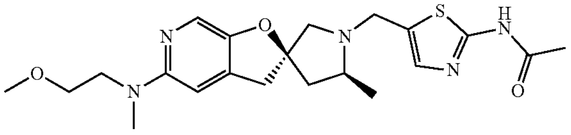 [SMILES: COCCN(C)c1cc2c(cn1)O[C@]1(C2)C[C@H](C)N(Cc2cnc(NC(C)=O)s2)C1]

The title compound was prepared in an analogous manner of that in Example 31 from 2-methoxy-N-methylethan-1-amine, tert-butyl (2R,5'S)-5-chloro-5'-methyl-3H-spiro[furo[2,3-c]pyridine-2,3'-pyrrolidine]-1'-carboxylate (Compound 10.2) and N-(5-(chloromethyl)thiazol-2-yl)acetamide. $^{1}$H NMR (500 MHz, METHANOL-$d_4$) δ 7.47 (d, J=0.61 Hz, 1H), 7.27 (s, 1H), 6.59 (d, J=0.92 Hz, 1H), 4.13 (d, J=14.34 Hz, 1H), 3.58-3.68 (m, 3H), 3.51-3.56 (m, 2H), 3.32 (s, 3H), 3.24 (d, J=10.53 Hz, 1H), 3.15 (d, J=0.76 Hz, 2H), 2.99 (s, 3H), 2.70-2.80 (m, 1H), 2.47 (d, J=10.68 Hz, 1H), 2.31 (dd, J=7.86, 13.81 Hz, 1H), 2.17-2.22 (m, 3H), 1.99 (ddd, J=1.14, 8.39, 13.81 Hz, 1H), 1.26 (d, J=6.10 Hz, 3H); LCMS (ESI): [M+H] 432.

Example 33: N-(4-Fluoro-5-(((2R,5'S)-5-((2-methoxyethyl)(methyl)amino)-5'-methyl-3H-spiro[furo[2,3-c]pyridine-2,3'-pyrrolidin]-1'-yl)methyl)thiazol-2-yl)acetamide

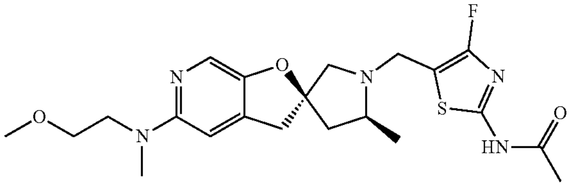 [SMILES: COCCN(C)c1cc2c(cn1)O[C@]1(C2)C[C@H](C)N(Cc2sc(NC(C)=O)nc2F)C1]

The title compound was prepared in an analogous manner of that in Example 31 from (2R,5'S)—N-(2-methoxyethyl)-N,5'-dimethyl-3H-spiro[furo[2,3-c]pyridine-2,3'-pyrrolidin]-5-amine and N-(5-(chloromethyl)-4-fluorothiazol-2-yl)acetamide. $^{1}$H NMR (500 MHz, METHANOL-$d_4$) δ 7.48 (d, J=0.76 Hz, 1H), 6.60 (d, J=0.92 Hz, 1H), 3.96 (d, J=14.65 Hz, 1H), 3.59-3.69 (m, 3H), 3.51-3.57 (m, 2H), 3.32 (s, 3H), 3.22-3.28 (m, 1H), 3.15 (d, J=0.61 Hz, 2H), 3.00 (s, 3H), 2.69-2.81 (m, 1H), 2.50 (d, J=10.68 Hz, 1H), 2.28-2.35 (m, 1H), 2.16-2.20 (m, 3H), 1.98 (ddd, J=1.22, 8.39, 13.89 Hz, 1H), 1.25 (d, J=6.10 Hz, 3H); LCMS (ESI): [M+H] 450.

Example 34: N-(5-(((2R,5'S)-5-(Azetidin-1-yl)-5'-methyl-3H-spiro[furo[2,3-c]pyridine-2,3'-pyrrolidin]-1'-yl)methyl)-4-fluorothiazol-2-yl)acetamide

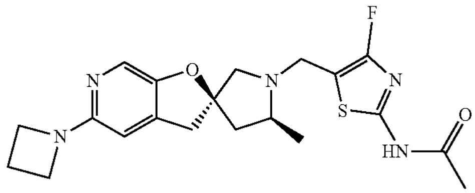 [SMILES: CC(=O)Nc1nc(F)c(CN2C[C@@]3(Cc4cc(N5CCC5)ncc4O3)C[C@@H]2C)s1]

The title compound was prepared in an analogous manner of that in Example 28 from azetidine, tert-butyl (2R,5'S)-5-chloro-5'-methyl-3H-spiro[furo[2,3-c]pyridine-2,3'-pyrrolidine]-1'-carboxylate (Compound 10.2) and N-(4-fluoro-5-formylthiazol-2-yl)acetamide. $^{1}$H NMR (400 MHz, METHANOL-$d_4$) δ 7.37 (s, 1H), 6.75 (s, 1H), 4.61 (br d, J=14.56 Hz, 1H), 4.39 (br d, J=16.06 Hz, 1H), 4.23 (t, J=7.65 Hz, 4H), 3.80 (br d, J=11.80 Hz, 2H), 3.50 (s, 2H), 3.35-3.45 (m, 1H), 2.75 (dd, J=9.66, 14.68 Hz, 1H), 2.53 (quin, J=7.72 Hz, 2H), 2.23-2.31 (m, 1H), 2.21 (s, 3H), 1.53 (d, J=6.78 Hz, 3H); LCMS (ESI): [M+H] 418.

Example 35: N-(5-(((2R,5'S)-5-(Azetidin-1-yl)-5'-methyl-3H-spiro[furo[2,3-c]pyridine-2,3'-pyrrolidin]-1'-yl)methyl)thiazol-2-yl)acetamide

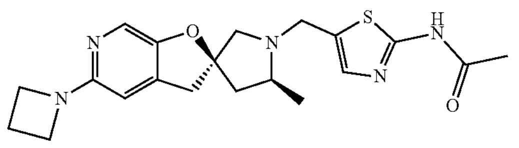 [SMILES: CC(=O)Nc1ncc(CN2C[C@@]3(Cc4cc(N5CCC5)ncc4O3)C[C@@H]2C)s1]

The title compound was prepared in an analogous manner of that in Example 2 from (2R,5'S)-5-(azetidin-1-yl)-5'-methyl-3H-spiro[furo[2,3-c]pyridine-2,3'-pyrrolidine] and N-(5-(chloromethyl)thiazol-2-yl)acetamide. LCMS (ESI): [M+H] 400.

Example 36: N-(4-Fluoro-5-(((2R,5'S)-5'-methyl-5-morpholino-3H-spiro[furo[2,3-c]pyridine-2,3'-pyrrolidin]-1'-yl)methyl)thiazol-2-yl)acetamide

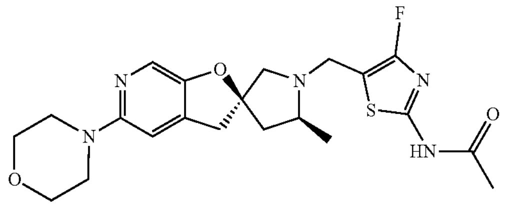 [SMILES: CC(=O)Nc1nc(F)c(CN2C[C@@]3(Cc4cc(N5CCOCC5)ncc4O3)C[C@@H]2C)s1]

The title compound was prepared in an analogous manner of that in Example 28 from morpholine, tert-butyl (2R,5'S)-5-chloro-5'-methyl-3H-spiro[furo[2,3-c]pyridine-2,3'-pyrrolidine]-1'-carboxylate (Compound 10.2) and N-(4-fluoro-5-formylthiazol-2-yl)acetamide. $^1$H NMR (400 MHz, METHANOL-$d_4$) δ 7.49 (s, 1H), 7.37 (s, 1H), 4.71 (d, J=14.81 Hz, 1H), 4.53 (d, J=14.81 Hz, 1H), 3.91-4.03 (m, 2H), 3.81-3.88 (m, 4H), 3.53-3.63 (m, 7H), 2.84 (dd, J=9.79, 14.56 Hz, 1H), 2.30-2.39 (m, 1H), 2.21 (s, 3H), 1.59 (d, J=6.78 Hz, 3H); LCMS (ESI): [M+H] 448.

Example 37: N-(5-(((2R,5'S)-5'-Methyl-5-morpholino-3H-spiro[furo[2,3-c]pyridine-2,3'-pyrrolidin]-1'-yl)methyl)thiazol-2-yl)acetamide

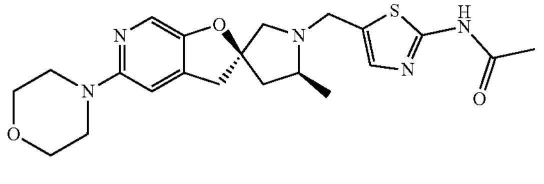 [SMILES: CC(=O)Nc1ncc(CN2C[C@@]3(Cc4cc(N5CCOCC5)ncc4O3)C[C@@H]2C)s1]

The title compound was prepared in an analogous manner of that in Example 2 from (2R,5'S)-5'-methyl-5-morpholino-3H-spiro[furo[2,3-c]pyridine-2,3'-pyrrolidine] and N-(5-(chloromethyl)thiazol-2-yl)acetamide. LCMS (ESI): [M+H] 430.

Example 38: N-(5-(((2R,5'S)-5-((2R,6S)-2,6-Dimethylmorpholino)-5'-methyl-3H-spiro[furo[2,3-c]pyridine-2,3'-pyrrolidin]-1'-yl)methyl)thiazol-2-yl)acetamide

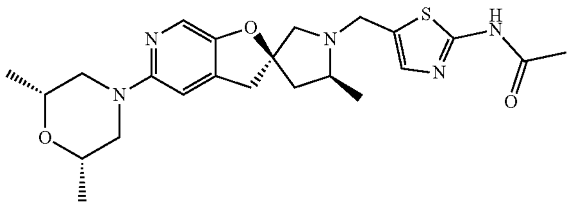 [SMILES: CC(=O)Nc1ncc(CN2C[C@@]3(Cc4cc(N5C[C@@H](C)O[C@@H](C)C5)ncc4O3)C[C@@H]2C)s1]

The title compound was prepared in an analogous manner of that in Example 31 from (2R,6S)-2,6-dimethylmorpholine, tert-butyl (2R,5'S)-5-chloro-5'-methyl-3H-spiro[furo[2,3-c]pyridine-2,3'-pyrrolidine]-1'-carboxylate (Compound 10.2) and N-(5-(chloromethyl)thiazol-2-yl)acetamide. $^1$H NMR (400 MHz, METHANOL-$d_4$) δ 7.64 (s, 1H), 7.47 (s, 1H), 7.36 (s, 1H), 4.83 (s, 1H), 4.60 (d, J=14.31 Hz, 1H), 3.93-4.06 (m, 1H), 3.80-3.92 (m, 3H), 3.69-3.79 (m, 2H), 3.54-3.62 (m, 3H), 2.73-2.87 (m, 3H), 2.29-2.40 (m, 1H), 2.22 (s, 3H), 1.56 (d, J=6.78 Hz, 3H), 1.25 (d, J=6.27 Hz, 6H); LCMS (ESI): [M+H] 458.

Example 39: N-(5-(((2R,5'S)-5-((2R,6S)-2,6-Dimethylmorpholino)-5'-methyl-3H-spiro[furo[2,3-c]pyridine-2,3'-pyrrolidin]-1'-yl)methyl)-4-fluorothiazol-2-yl)acetamide

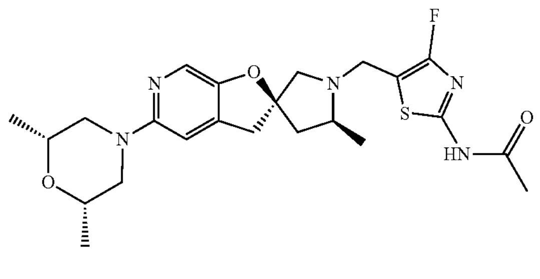 [SMILES: CC(=O)Nc1nc(F)c(CN2C[C@@]3(Cc4cc(N5C[C@@H](C)O[C@@H](C)C5)ncc4O3)C[C@@H]2C)s1]

The title compound was prepared in an analogous manner of that in Example 31 from (2R,5'S)-5-((2R,6S)-2,6-dimethylmorpholino)-5'-methyl-3H-spiro[furo[2,3-c]pyridine-2,3'-pyrrolidine] and N-(5-(chloromethyl)-4-fluorothiazol-2-yl)acetamide. $^1$H NMR (400 MHz, METHANOL-$d_4$) δ 7.48 (s, 1H), 7.33 (s, 1H), 4.70 (d, J=14.81 Hz, 1H), 4.51 (d, J=14.81 Hz, 1H), 3.85-3.98 (m, 4H), 3.69-3.80 (m, 2H), 3.51-3.59 (m, 3H), 2.71-2.87 (m, 3H), 2.33 (ddd, J=1.63, 5.83, 14.62 Hz, 1H), 2.21 (s, 3H), 1.58 (d, J=6.53 Hz, 3H), 1.25 (d, J=6.02 Hz, 6H); LCMS (ESI): [M+H] 476.

Example 40: N-(5-(((2R,5'S)-5-((2R,6R)-2,6-Dimethylmorpholino)-5'-methyl-3H-spiro[furo[2,3-c]pyridine-2,3'-pyrrolidin]-1'-yl)methyl)thiazol-2-yl)acetamide

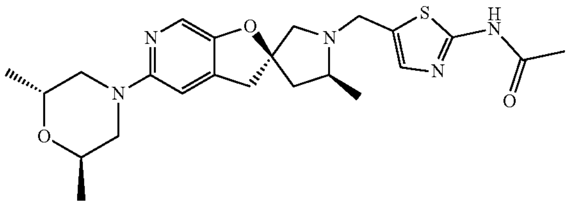 [SMILES: CC(=O)Nc1ncc(CN2C[C@@]3(Cc4cc(N5C[C@@H](C)O[C@H](C)C5)ncc4O3)C[C@@H]2C)s1]

The title compound was prepared in an analogous manner of that in Example 31 from (2R,6R)-2,6-dimethylmorpholine, tert-butyl (2R,5'S)-5-chloro-5'-methyl-3H-spiro[furo[2,3-c]pyridine-2,3'-pyrrolidine]-1'-carboxylate (Compound 10.2) and N-(5-(chloromethyl)thiazol-2-yl)acetamide. $^1$H NMR (400 MHz, METHANOL-$d_4$) δ 7.64 (s, 1H), 7.46 (s, 1H), 7.31 (s, 1H), 4.82 (s, 1H), 4.60 (d, J=14.31 Hz, 1H), 4.19 (dt, J=3.39, 6.71 Hz, 2H), 3.94-4.05 (m, 1H), 3.84 (dd, J=1.76, 12.55 Hz, 1H), 3.64 (dd, J=3.26, 12.80 Hz, 2H), 3.54-3.60 (m, 3H), 3.32-3.37 (m, 2H), 2.82 (dd, J=9.66, 14.68 Hz, 1H), 2.30-2.39 (m, 1H), 2.22 (s, 3H), 1.56 (d, J=6.78 Hz, 3H), 1.25 (d, J=6.27 Hz, 6H); LCMS (ESI): [M+H] 458.

Example 41: N-(5-(((2R,5'S)-5-((2R,6R)-2,6-Dimethylmorpholino)-5'-methyl-3H-spiro[furo[2,3-c]pyridine-2,3'-pyrrolidin]-1'-yl)methyl)-4-fluorothiazol-2-yl)acetamide

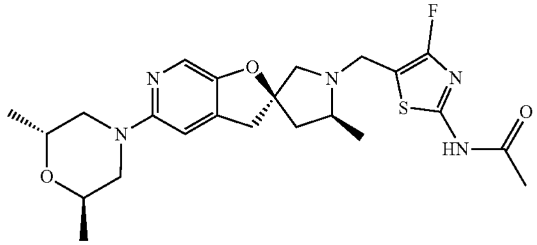 [SMILES: CC(=O)Nc1nc(F)c(CN2C[C@@]3(Cc4cc(N5C[C@@H](C)O[C@H](C)C5)ncc4O3)C[C@@H]2C)s1]

The title compound was prepared in an analogous manner of that in Example 31 from (2R,5'S)-5-((2R,6R)-2,6-dimethylmorpholino)-5'-methyl-3H-spiro[furo[2,3-c]pyridine-2,3'-pyrrolidine] and N-(5-(chloromethyl)-4-fluorothiazol-2-yl)acetamide. $^1$H NMR (400 MHz, METHANOL-$d_4$) δ 7.46 (s, 1H), 7.31 (s, 1H), 4.71 (d, J=14.56 Hz, 1H), 4.52 (d, J=14.81 Hz, 1H), 4.19 (dquin, J=3.26, 6.59 Hz, 2H), 3.87-4.02 (m, 2H), 3.64 (dd, J=3.51, 12.80 Hz, 2H), 3.51-3.60 (m, 3H), 3.32-3.37 (m, 2H), 2.78-2.87 (m, 1H), 2.33 (ddd, J=1.63, 5.96, 14.74 Hz, 1H), 2.21 (s, 3H), 1.58 (d, J=6.78 Hz, 3H), 1.25 (d, J=6.27 Hz, 6H); LCMS (ESI): [M+H] 476.

Example 42: N-(5-(((2R,5'S)-5-((2S,6S)-2,6-Dimethylmorpholino)-5'-methyl-3H-spiro[furo[2,3-c]pyridine-2,3'-pyrrolidin]-1'-yl)methyl)thiazol-2-yl)acetamide

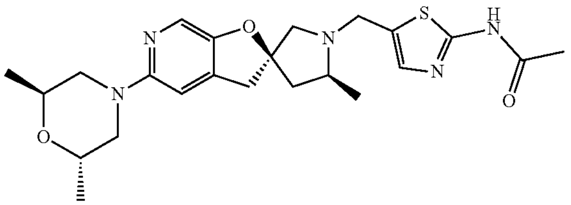 [SMILES: CC(=O)Nc1ncc(CN2C[C@@]3(Cc4cc(N5C[C@H](C)O[C@@H](C)C5)ncc4O3)C[C@@H]2C)s1]

The title compound was prepared in an analogous manner of that in Example 31 from (2S,6S)-2,6-dimethylmorpholine, tert-butyl (2R,5'S)-5-chloro-5'-methyl-3H-spiro[furo[2,3-c]pyridine-2,3'-pyrrolidine]-1'-carboxylate (Compound 10.2) and N-(5-(chloromethyl)thiazol-2-yl)acetamide. $^1$H NMR (400 MHz, METHANOL-$d_4$) δ 7.64 (s, 1H), 7.46 (s, 1H), 7.29 (s, 1H), 4.82 (s, 1H), 4.59 (d, J=14.30 Hz, 1H), 4.13-4.24 (m, 2H), 3.98 (td, J=6.40, 9.54 Hz, 1H), 3.82 (dd, J=1.88, 12.42 Hz, 1H), 3.63 (dd, J=3.39, 12.67 Hz, 2H), 3.52-3.59 (m, 3H), 3.34 (br d, J=7.03 Hz, 2H), 2.82 (dd, J=9.66, 14.68 Hz, 1H), 2.29-2.40 (m, 1H), 2.22 (s, 3H), 1.56 (d, J=6.78 Hz, 3H), 1.25 (d, J=6.53 Hz, 6H); LCMS (ESI): [M+H] 458.

Example 43: N-(5-(((2R,5'S)-5-((2S,6S)-2,6-Dimethylmorpholino)-5'-methyl-3H-spiro[furo[2,3-c]pyridine-2,3'-pyrrolidin]-1'-yl)methyl)-4-fluorothiazol-2-yl)acetamide

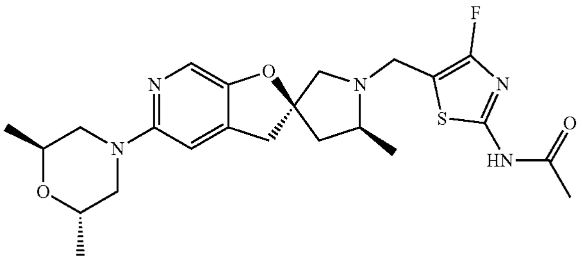 [SMILES: CC(=O)Nc1nc(F)c(CN2C[C@@]3(Cc4cc(N5C[C@H](C)O[C@@H](C)C5)ncc4O3)C[C@@H]2C)s1]

The title compound was prepared in an analogous manner of that in Example 31 from (2R,5'S)-5-((2S,6S)-2,6-dimethylmorpholino)-5'-methyl-3H-spiro[furo[2,3-c]pyridine-2,3'-pyrrolidine] and N-(5-(chloromethyl)-4-fluorothiazol-2-yl)acetamide. $^1$H NMR (400 MHz, METHANOL-$d_4$) δ 7.47 (s, 1H), 7.26 (s, 1H), 4.70 (d, J=14.56 Hz, 1H), 4.51 (d, J=14.81 Hz, 1H), 4.18 (dquin, J=3.39, 6.56 Hz, 2H), 3.85-3.99 (m, 2H), 3.62 (dd, J=3.39, 12.67 Hz, 2H), 3.50-3.58 (m, 3H), 3.33 (s, 1H), 3.28 (s, 1H), 2.82 (dd, J=9.66, 14.68 Hz, 1H), 2.29-2.38 (m, 1H), 2.21 (s, 3H), 1.58 (d, J=6.78 Hz, 3H), 1.25 (d, J=6.27 Hz, 6H); LCMS (ESI): [M+H] 476.

Example 44: N-(5-(((2R,5'S)-5'-Methyl-5-(4-methylpiperazin-1-yl)-3H-spiro[furo[2,3-c]pyridine-2,3'-pyrrolidin]-1'-yl)methyl)thiazol-2-yl)acetamide

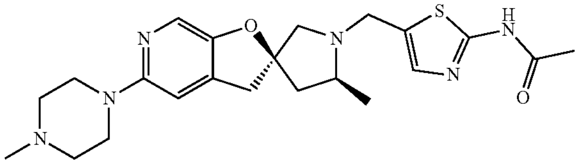 [SMILES: CC(=O)Nc1ncc(CN2C[C@@]3(Cc4cc(N5CCN(C)CC5)ncc4O3)C[C@@H]2C)s1]

The title compound was prepared in an analogous manner of that in Example 31 from 1-methylpiperazine, tert-butyl (2R,5'S)-5-chloro-5'-methyl-3H-spiro[furo[2,3-c]pyridine-2,3'-pyrrolidine]-1'-carboxylate (Compound 10.2) and N-(5-(chloromethyl)thiazol-2-yl)acetamide. $^1$H NMR (500 MHz, METHANOL-$d_4$) δ 7.56 (s, 1H), 7.26 (s, 1H), 6.78 (d, J=0.76 Hz, 1H), 4.12 (dd, J=0.61, 14.34 Hz, 1H), 3.63 (d, J=14.34 Hz, 1H), 3.33-3.41 (m, 4H), 3.24 (d, J=10.68 Hz, 1H), 3.17 (s, 2H), 2.68-2.79 (m, 1H), 2.58 (t, J=4.96 Hz, 4H), 2.46 (d, J=10.83 Hz, 1H), 2.28-2.38 (m, 4H), 2.17-2.21 (m, 3H), 1.99 (ddd, J=0.99, 8.39, 13.81 Hz, 1H), 1.26 (d, J=6.10 Hz, 3H); LCMS (ESI): [M+H] 443.

Example 45: N-(4-Fluoro-5-(((2R,5'S)-5'-methyl-5-(4-methylpiperazin-1-yl)-3H-spiro[furo[2,3-c]pyridine-2,3'-pyrrolidin]-1'-yl)methyl)thiazol-2-yl)acetamide

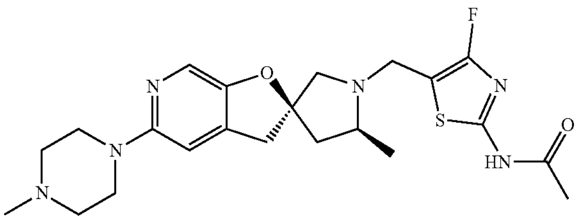 [SMILES: CC(=O)Nc1nc(F)c(CN2C[C@@]3(Cc4cc(N5CCN(C)CC5)ncc4O3)C[C@@H]2C)s1]

The title compound was prepared in an analogous manner of that in Example 31 from (2R,5'S)-5'-methyl-5-(4-methylpiperazin-1-yl)-3H-spiro[furo[2,3-c]pyridine-2,3'-pyrrolidine] and N-(5-(chloromethyl)-4-fluorothiazol-2-yl)acetamide. $^1$H NMR (500 MHz, METHANOL-$d_4$) δ 7.56 (d, J=0.76 Hz, 1H), 6.79 (d, J=0.76 Hz, 1H), 3.96 (d, J=14.50 Hz, 1H), 3.63 (d, J=14.65 Hz, 1H), 3.33-3.43 (m, 4H), 3.26 (d, J=10.68 Hz, 1H), 3.18 (s, 2H), 2.69-2.80 (m, 1H), 2.58 (t, J=5.04 Hz, 4H), 2.49 (d, J=10.68 Hz, 1H), 2.28-2.38 (m, 4H), 2.14-2.21 (m, 3H), 1.98 (ddd, J=1.22, 8.39, 13.89 Hz, 1H), 1.25 (d, J=6.10 Hz, 3H); LCMS (ESI): [M+H] 461.

Example 46: N-(5-(((2R,5'S)-5-Ethoxy-5'-methyl-3H-spiro[furo[2,3-c]pyridine-2,3'-pyrrolidin]-1'-yl)methyl)-4-fluorothiazol-2-yl)acetamide

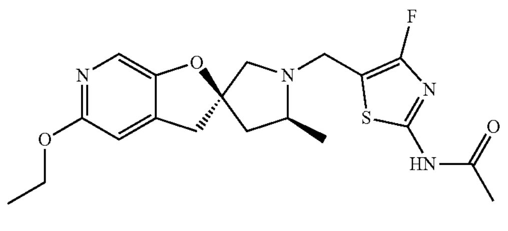

-continued

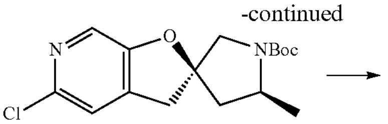

10.2

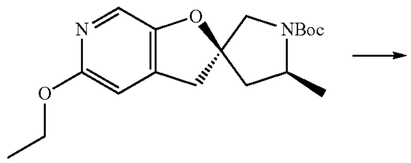

46.1

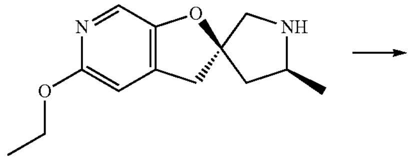

46.2

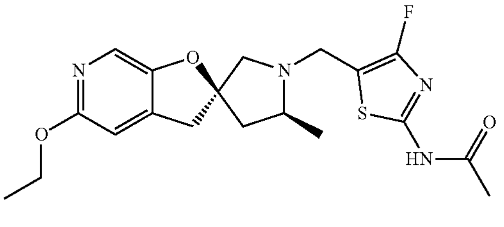

46

Compound 46.1: tert-Butyl (2R,5'S)-5-ethoxy-5'-methyl-3H-spiro[furo[2,3-c]pyridine-2,3'-pyrrolidine]-1'-carboxylate: A mixture of tert-butyl (2R,5'S)-5-chloro-5'-methyl-3H-spiro[furo[2,3-c]pyridine-2,3'-pyrrolidine]-1'-carboxylate (Compound 10.2, 100 mg, 308 umol), [2-(2-aminophenyl)phenyl]-methylsulfonyloxy-palladium; ditert-butyl-[3,6-dimethoxy-2-(2,4,6-triisopropylphenyl)phenyl] phosphane (5.3 mg, 6.16 umol), sodium tert-butoxide (60 mg, 615.76 umol) in dioxane (3.0 mL) was purged with nitrogen for 5 min. Ethanol (71 mg, 1.54 mmol) was then added, and the mixture was heated in a sealed tube at 85° C. under nitrogen for 1 h. Filter off the solid, the filtrate was concentrated and purified by chromatography on silica gel (0-100% EtOAc in heptane) to give the title compound (54 mg, 52% yield). $^1$H NMR (400 MHz, METHANOL-$d_4$) δ 7.51 (d, J=0.75 Hz, 1H), 6.67 (d, J=0.75 Hz, 1H), 4.21 (q, J=7.03 Hz, 2H), 4.02-4.13 (m, 1H), 3.70 (br d, J=12.30 Hz, 1H), 3.51 (d, J=12.05 Hz, 1H), 3.16-3.28 (m, 2H), 2.33 (br d, J=7.28 Hz, 1H), 2.06 (br d, J=13.55 Hz, 1H), 1.48 (br s, 9H), 1.39-1.42 (m, 3H), 1.33 (t, J=7.03 Hz, 3H); LCMS (ESI): [M+H] 335.

Compound 46.2: (2R,5'S)-5-Ethoxy-5'-methyl-3H-spiro[furo[2,3-c]pyridine-2,3'-pyrrolidine]: The title compound was prepared in an analogous manner of that in Compound 1.3 from tert-butyl (2R,5'S)-5-ethoxy-5'-methyl-3H-spiro[furo[2,3-c]pyridine-2,3'-pyrrolidine]-1'-carboxylate. LCMS (ESI): [M+H] 235.

The title compound was prepared in an analogous manner of that in Example 1 from (2R,5'S)-5-ethoxy-5'-methyl-3H-spiro[furo[2,3-c]pyridine-2,3'-pyrrolidine] and N-(4-fluoro-5-formylthiazol-2-yl)acetamide. $^1$H NMR (400 MHz, METHANOL-$d_4$) δ 7.60 (s, 1H), 6.83 (br s, 1H), 4.69 (d, J=14.56 Hz, 1H), 4.51 (d, J=14.81 Hz, 1H), 4.25 (q, J=7.03 Hz, 2H), 3.95 (td, J=6.37, 9.85 Hz, 1H), 3.85 (d, J=12.05 Hz, 1H), 3.39-3.53 (m, 3H), 2.78 (dd, J=9.79, 14.56 Hz, 1H), 2.26-2.35 (m, 1H), 2.21 (s, 3H), 1.58 (d, J=6.78 Hz, 3H), 1.36 (t, J=7.03 Hz, 3H); LCMS (ESI): [M+H] 407.

Example 47: N-(4-Fluoro-5-(((2R,5'S)-5-(2-methoxyethoxy)-5'-methyl-3H-spiro[furo[2,3-c]pyridine-2,3'-pyrrolidin]-1'-yl)methyl)thiazol-2-yl)acetamide

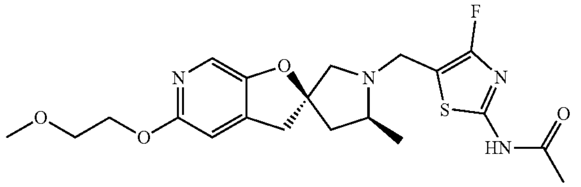 [SMILES: COCCOc1cc2c(cn1)O[C@]1(C2)C[C@H](C)N(Cc2sc(NC(C)=O)nc2F)C1]

The title compound was prepared in an analogous manner of that in Example 46 from 2-methoxyethan-1-ol, tert-butyl (2R,5'S)-5-chloro-5'-methyl-3H-spiro[furo[2,3-c]pyridine-2,3'-pyrrolidine]-1'-carboxylate (Compound 10.2) and N-(4-fluoro-5-formylthiazol-2-yl)acetamide. $^1$H NMR (400 MHz, METHANOL-$d_4$) δ 7.58 (s, 1H), 6.77 (s, 1H), 4.68 (d, J=14.56 Hz, 1H), 4.51 (d, J=14.81 Hz, 1H), 4.33 (dd, J=4.14, 5.40 Hz, 2H), 3.89-4.01 (m, 1H), 3.83 (dd, J=1.76, 12.05 Hz, 1H), 3.67-3.74 (m, 2H), 3.48 (br d, J=12.30 Hz, 1H), 3.41 (s, 2H), 3.39 (s, 3H), 2.77 (dd, J=9.91, 14.43 Hz, 1H), 2.29 (br dd, J=4.14, 14.68 Hz, 1H), 2.21 (s, 3H), 1.58 (d, J=6.78 Hz, 3H); LCMS (ESI): [M+H] 437.

Example 48: N-(5-(((2R,5'S)-5',6-Dimethyl-5-oxo-5,6-dihydro-3H-spiro[furo[2,3-c]pyridine-2,3'-pyrrolidin]-1'-yl)methyl)-4-fluorothiazol-2-yl)acetamide

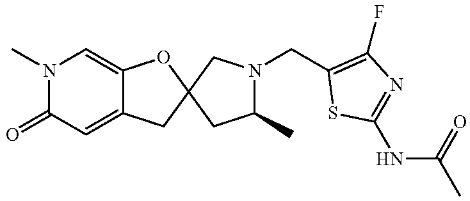

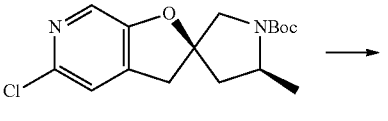

10.2

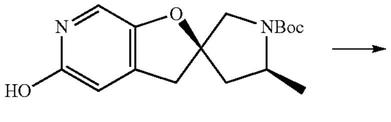

48.1

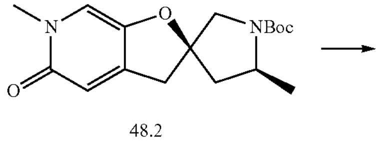

48.2

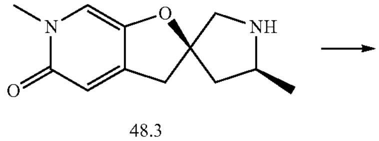

48.3

-continued

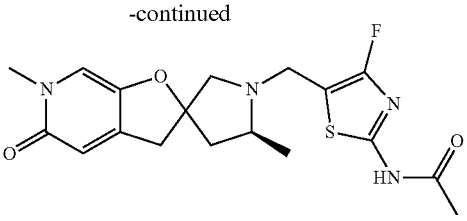

48

Compound 48.1: tert-Butyl (2R,5'S)-5-hydroxy-5'-methyl-3H-spiro[furo[2,3-c]pyridine-2,3'-pyrrolidine]-1'-carboxylate: A mixture of tert-butyl (2R,5'S)-5-chloro-5'-methyl-3H-spiro[furo[2,3-c]pyridine-2,3'-pyrrolidine]-1'-carboxylate (Compound 10.2, 100 mg, 308 umol), cyclopropanol (89 mg, 1.54 mmol), [2-(2-aminophenyl)phenyl]-methylsulfonyloxy-palladium; ditert-butyl-[3,6-dimethoxy-2-(2,4,6-triisopropylphenyl)phenyl]phosphane (5.3 mg, 6.16 umol), sodium tert-butoxide (59 mg, 615.76 umol) and NaI (46 mg, 308 umol) in dioxane (3.0 mL) was heated in a sealed tube at 65° C. under nitrogen overnight. Filter off the solid, the filtrate was concentrated and purified by HPLC to give the title compound (22 mg, 23% yield). LCMS (ESI): [M+H] 307.

Compound 48.2: tert-Butyl (2R,5'S)-5',6-dimethyl-5-oxo-5,6-dihydro-3H-spiro[furo[2,3-c]pyridine-2,3'-pyrrolidine]-1'-carboxylate: A mixture of tert-butyl (2R,5'S)-5-hydroxy-5'-methyl-3H-spiro[furo[2,3-c]pyridine-2,3'-pyrrolidine]-1'-carboxylate (20 mg, 65.28 umol), methyl iodide (1.14 g, 8.03 mmol), $K_2CO_3$ (27 mg, 195.84 umol) in acetone (1.0 mL) was stirred at rt for 48 h. Remove all the solvent, the crude was purified by chromatography on silica gel (0-80% EtOAc-EtOH 3:1 with 2% $NH_4OH$ in heptane) to give the title compound (18 mg, 90% yield). $^1$H NMR (400 MHz, METHANOL-$d_4$) δ 7.24 (s, 1H), 6.55 (s, 1H), 4.07 (br dd, J=6.78, 11.54 Hz, 1H), 3.69 (br d, J=12.30 Hz, 1H), 3.49-3.56 (m, 4H), 3.15-3.29 (m, 2H), 2.35 (br s, 1H), 2.03 (s, 1H), 1.47 (br s, 9H), 1.37 (d, J=6.53 Hz, 3H); LCMS (ESI): [M+H] 321.

Compound 48.3: (2R,5'S)-5',6-Dimethyl-3H-spiro[furo[2,3-c]pyridine-2,3'-pyrrolidin]-5 (6H)-one: The title compound was prepared in an analogous manner of that in Compound 31.2 from tert-butyl (2R,5'S)-5',6-dimethyl-5-oxo-5,6-dihydro-3H-spiro[furo[2,3-c]pyridine-2,3'-pyrrolidine]-1'-carboxylate. LCMS (ESI): [M+H] 221.

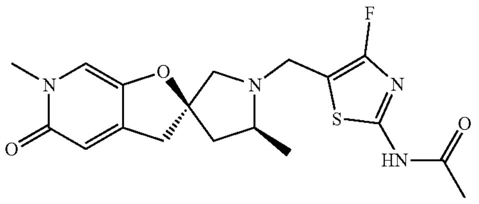 [SMILES: CC(=O)Nc1nc(F)c(CN2C[C@@]3(Cc4cc(=O)n(C)cc4O3)C[C@@H]2C)s1]

The title compound was prepared in an analogous manner of that in Example 31 from (2R,5'S)-5',6-dimethyl-3H-spiro[furo[2,3-c]pyridine-2,3'-pyrrolidin]-5 (6H)-one and N-(5-(chloromethyl)-4-fluorothiazol-2-yl)acetamide. $^1$H NMR (400 MHz, METHANOL-$d_4$) δ 7.21 (s, 1H), 6.48 (s, 1H), 4.68 (d, J=14.56 Hz, 1H), 4.49 (d, J=14.56 Hz, 1H), 3.91 (br s, 1H), 3.82 (dd, J=2.01, 12.30 Hz, 1H), 3.45-3.52 (m, 4H), 3.37 (s, 2H), 2.72-2.83 (m, 1H), 2.19-2.31 (m, 4H), 1.56 (d, J=6.78 Hz, 3H); LCMS (ESI): [M+H] 393.

Example 49: N-(4-Fluoro-5-(((2R,5'S)-5'-methyl-5-oxo-5,6-dihydro-3H-spiro[furo[2,3-c]pyridine-2,3'-pyrrolidin]-1'-yl)methyl)thiazol-2-yl)acetamide

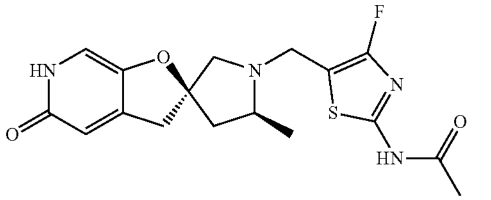

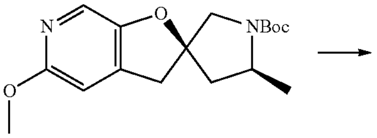

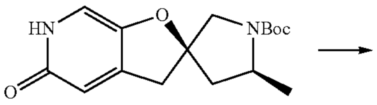

49.1

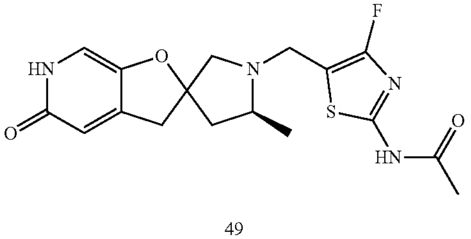

49

Compound 49.1: (2R,5'S)-5'-Methyl-3H-spiro[furo[2,3-c]pyridine-2,3'-pyrrolidin]-5 (6H)-one: To a mixture of tert-butyl (2R,5'S)-5-methoxy-5'-methyl-3H-spiro[furo[2,3-c]pyridine-2,3'-pyrrolidine]-1'-carboxylate (Intermediate from Example 16, 100 mg, 312.13 umol,) and NaI (234 mg, 1.56 mmol) in acetonitrile (2.0 mL) was dropwise added TMSCl (170 mg, 1.56 mmol). The reaction mixture was stirred at RT for 1 h. Water (100 μL) was added and the mixture was stirred at 65° C. for 3 h. The crude was concentrated and purified by HPLC to give the title compound (76 mg, 76% yield, TFA salt) which was used in the next step without further purifications. LCMS (ESI): [M+H] 207.

The title compound was prepared in an analogous manner of that in Example 1 from (2R,5'S)-5'-methyl-3H-spiro[furo[2,3-c]pyridine-2,3'-pyrrolidin]-5 (6H)-one and N-(4-fluoro-5-formylthiazol-2-yl)acetamide. $^1$H NMR (400 MHz, METHANOL-$d_4$) δ 7.00 (s, 1H), 6.52 (d, J=0.75 Hz, 1H), 4.68 (d, J=14.81 Hz, 1H), 4.47-4.54 (m, 1H), 3.88-4.00 (m, 1H), 3.81-3.87 (m, 1H), 3.46-3.53 (m, 1H), 3.40 (s, 2H), 2.77 (dd, J=9.79, 14.56 Hz, 1H), 2.25-2.32 (m, 1H), 2.22 (s, 3H), 1.56 (d, J=6.78 Hz, 3H); LCMS (ESI): [M+H] 379:

Example 50: N-(4-Fluoro-5-(((5'S)-2-methoxy-5'-methyl-7H-spiro[furo[2,3-b]pyrazine-6,3'-pyrrolidin]-1'-yl)methyl)thiazol-2-yl)acetamide

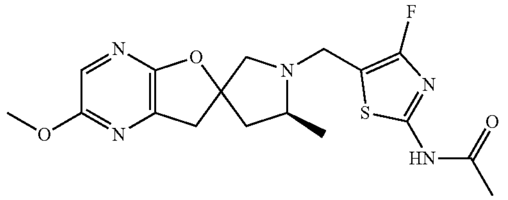

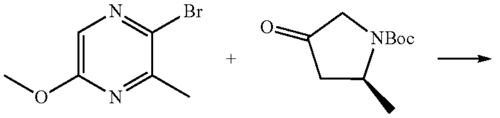

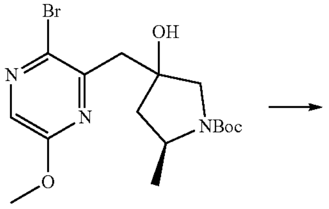

50.1

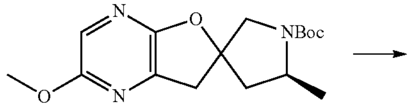

50.2

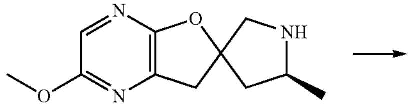

50.2

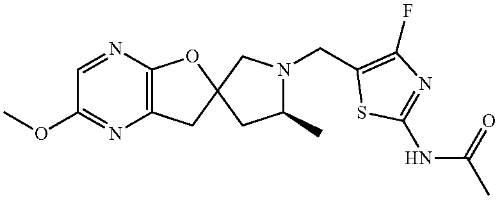

50

Compound 50.1: tert-Butyl (2S)-4-((3-bromo-6-methoxy-pyrazin-2-yl)methyl)-4-hydroxy-2-methylpyrrolidine-1-carboxylate: n-BuLi (2.5 M in hexanes, 1.99 mL) was added dropwise to a solution of N-isopropylpropan-2-amine (502 mg, 4.97 mmol, 698 uL) in THF (3.0 mL) at 0° C. The LDA solution was stirred at 0° C. for 30 min. In another flask, a solution of 2-bromo-5-methoxy-3-methyl-pyrazine (1.0 g, 4.97 mmol) in THF (6.0 mL) was cooled to −78° C. To this was dropwise added the LDA solution. The mixture was stirred at −78° C. for 1 h. A solution of tert-butyl (2S)-2-methyl-4-oxo-pyrrolidine-1-carboxylate (660.18 mg, 3.31 mmol) in THF (3.0 mL) was then dropwise added. The mixture was stirred 30 min at −78° C. and slowly warmed up to rt overnight. The reaction was quenched with aq. $NH_4Cl$, diluted with EtOAc, washed with water (3×), then brine. The organic layer was then separated, dried and concentrated. The crude was purified by chromatography on silica gel (0-100% EtOAc in heptane) to give the title compound (486 mg, 33% yield). $^1$H NMR (400 MHz, METHANOL-$d_4$) δ 7.90 (s, 1H), 3.81-4.05 (m, 5H), 3.76 (d, J=12.05 Hz, 1H), 3.41-3.60 (m, 1H), 3.05-3.26 (m, 1H), 2.30-2.48 (m, 1H), 1.78-1.87 (m, 1H), 1.45 (s, 9H), 1.35 (d, J=6.53 Hz, 3H); LCMS (ESI): [M-Boc] 302/304.

Compound 50.2: tert-Butyl (5'S)-2-methoxy-5'-methyl-7H-spiro[furo[2,3-b]pyrazine-6,3'-pyrrolidine]-1'-carboxylate: A mixture of sodium tert-butoxide (154 mg, 1.60 mmol), [2-(2-aminophenyl)phenyl]-methylsulfonyloxy-palladium; ditert-butyl-[3,6-dimethoxy-2-(2,4,6-triisopropylphenyl)phenyl]phosphane (18.3 mg, 21.38 umol) and tert-butyl (2S)-4-[(3-bromo-6-methoxy-pyrazin-2-yl)methyl]-4-hydroxy-2-methyl-pyrrolidine-1-carboxylate (430 mg, 1.07 mmol) in dioxane (8.0 mL) was heated at 80° C. for 30 min. Diluted with EtOAc, washed with brine. The organic layer was then separated, dried and concentrated. The crude was purified by chromatography on silica gel (0-80% EtOAc in heptane) to give the title compound (62 mg, 18% yield) as a colorless oil. LCMS (ESI): [M-tBu] 266.

Compound 50.3: (5'S)-2-Methoxy-5'-methyl-7H-spiro[furo[2,3-b]pyrazine-6,3'-pyrrolidine]: The title compound was prepared in an analogous manner of that in Compound 1.3 from tert-butyl (5'S)-2-methoxy-5'-methyl-7H-spiro[furo[2,3-b]pyrazine-6,3'-pyrrolidine]-1'-carboxylate. LCMS (ESI): [M+H] 222.

The title compound was prepared in an analogous manner of that in Example 31 from (5'S)-2-methoxy-5'-methyl-7H-spiro[furo[2,3-b]pyrazine-6,3'-pyrrolidine] and N-(5-(chloromethyl)-4-fluorothiazol-2-yl)acetamide. $^1$H NMR (500 MHz, METHANOL-$d_4$) δ 7.58 (t, J=1.22 Hz, 1H), 4.70 (d, J=14.65 Hz, 1H), 4.53 (d, J=14.65 Hz, 1H), 3.93-4.03 (m, 2H), 3.89-3.92 (m, 3H), 3.53 (br d, J=12.36 Hz, 1H), 3.49 (s, 2H), 2.81 (dd, J=9.99, 14.57 Hz, 1H), 2.39 (br dd, J=3.81, 14.34 Hz, 1H), 2.22 (s, 3H), 1.60 (d, J=6.71 Hz, 3H); LCMS (ESI): [M+H] 394.

Example 51: N-(4-fluoro-5-(((5'S)-2-hydroxy-5'-methyl-7H-spiro[furo[2,3-b]pyrazine-6,3'-pyrrolidin]-1'-yl)methyl)thiazol-2-yl)acetamide

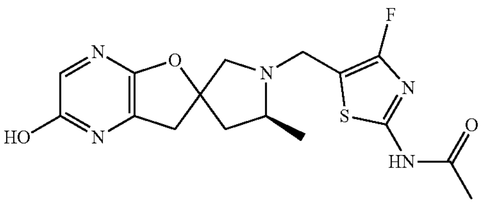

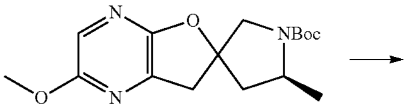

50.2

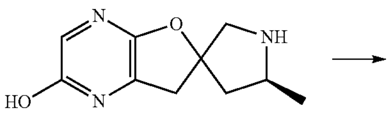

51.1

-continued

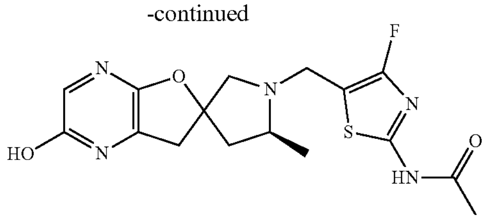

51

Compound 51.1: (5'S)-5'-Methyl-7H-spiro[furo[2,3-b]pyrazine-6,3'-pyrrolidin]-2-ol: To a solution of tert-butyl (5'S)-2-methoxy-5'-methyl-7H-spiro[furo[2,3-b]pyrazine-6,3'-pyrrolidine]-1'-carboxylate (Compound 50.2, 50 mg, 156 umol) in DCM (2.0 mL) was added HCl (4 M in dioxane, 233 uL). The mixture was stirred at rt overnight. Remove all the solvent, the crude was triturated with ether, then dried to give the title compound (40 mg, 105% yield, Hydrochloride) which was used in the next step without further purifications. LCMS (ESI): [M+H] 208.

The title compound was prepared in an analogous manner of that in Example 31 from (5'S)-5'-methyl-7H-spiro[furo[2,3-b]pyrazine-6,3'-pyrrolidin]-2-ol and N-(5-(chloromethyl)-4-fluorothiazol-2-yl)acetamide. $^1$H NMR (400 MHz, METHANOL-$d_4$) δ 7.51 (s, 1H), 4.64-4.73 (m, 1H), 4.48 (d, J=14.81 Hz, 1H), 3.91 (s, 3H), 3.58-3.78 (m, 2H), 2.77-3.03 (m, 1H), 2.22 (s, 3H), 2.06-2.19 (m, 1H), 1.53-1.61 (m, 3H); LCMS (ESI): [M+H] 380.

Example 52: N-(5-((1-Oxa-7-azaspiro[4.5]decan-7-yl)methyl)thiazol-2-yl)acetamide

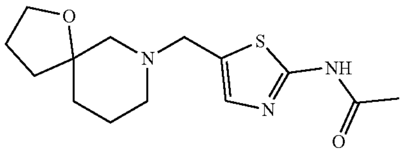 [SMILES: CC(=O)Nc1ncc(CN2CCCC3(CCCO3)C2)s1]

The title compound was prepared in an analogous manner of that in Example 2 from 1-oxa-7-azaspiro[4.5]decane and N-(5-(chloromethyl)thiazol-2-yl)acetamide. $^1$H NMR (400 MHz, METHANOL-$d_4$) δ 7.21 (s, 1H), 3.55-3.91 (m, 4H), 2.12-2.67 (m, 4H), 2.19 (s, 3H), 1.42-2.01 (m, 8H). LCMS (ESI): [M+H] 296.

Example 53: N-(5-((2,3-Dihydrospiro[indene-1,3'-piperidin]-1'-yl)methyl)thiazol-2-yl)acetamide

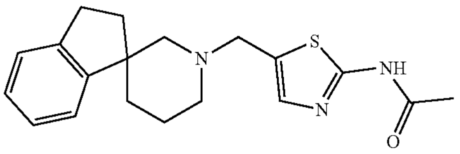 [SMILES: CC(=O)Nc1ncc(CN2CCCC3(CCc4ccccc43)C2)s1]

The title compound was prepared in an analogous manner of that in Example 2 from 2,3-dihydrospiro[indene-1,3'-piperidine] and N-(5-(chloromethyl)thiazol-2-yl)acetamide. $^1$H NMR (400 MHz, METHANOL-$d_4$) δ 7.01-7.30 (m, 5H), 3.52-3.77 (m, 2H), 2.73-2.95 (m, 3H), 2.50 (br d, J=10.54

Hz, 1H), 2.35 (br d, J=5.52 Hz, 1H), 2.13-2.25 (m, 1H), 2.19 (s, 3H), 1.97-2.11 (m, 1H), 1.43-1.94 (m, 5H). LCMS (ESI): [M+H] 342.

Example 54: N-(5-((2H-Spiro[benzofuran-3,3'-piperidin]-1'-yl)methyl)-4-fluorothiazol-2-yl)acetamide

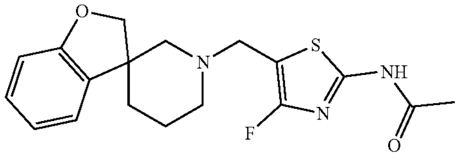 [SMILES: CC(=O)Nc1nc(F)c(CN2CCCC3(COc4ccccc43)C2)s1]

The title compound was prepared in an analogous manner of that in Example 1 from 2H-spiro[benzofuran-3,3'-piperidine] and N-(4-fluoro-5-formylthiazol-2-yl)acetamide. $^1$H NMR (400 MHz, METHANOL-$d_4$) δ 7.01-7.18 (m, 2H), 6.77-6.88 (m, 1H), 6.69 (dd, J=1.00, 8.03 Hz, 1H), 4.48-4.61 (m, 1H), 4.18-4.31 (m, 1H), 3.50-3.65 (m, 2H), 2.81-2.93 (m, 1H), 2.65 (d, J=11.04 Hz, 1H), 2.11-2.31 (m, 2H), 2.18 (s, 3H), 1.51-1.82 (m, 4H). LCMS (ESI): [M+H] 362.

Example 55: N-(5-((3H-Spiro[isobenzofuran-1,3'-piperidin]-1'-yl)methyl)thiazol-2-yl)acetamide

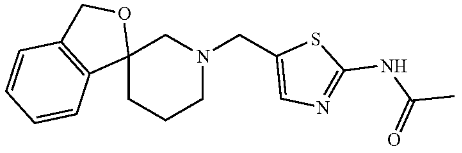 [SMILES: CC(=O)Nc1ncc(CN2CCCC3(C2)OCc2ccccc23)s1]

The title compound was prepared in an analogous manner of that in Example 2 from 3H-spiro[isobenzofuran-1,3'-piperidine] and N-(5-(chloromethyl)thiazol-2-yl)acetamide. $^1$H NMR (400 MHz, METHANOL-$d_4$) δ 7.13-7.39 (m, 5H), 4.95-5.10 (m, 2H), 3.67-3.85 (m, 2H), 2.77 (br s, 1H), 2.66 (d, J=11.80 Hz, 1H), 2.31-2.47 (m, 2H), 2.19 (s, 3H), 1.97 (br s, 1H), 1.64-1.80 (m, 3H). LCMS (ESI): [M+H] 344.

Example 56: N-(5-((3H-Spiro[isobenzofuran-1,3'-piperidin]-1'-yl)methyl)-4-fluorothiazol-2-yl)acetamide

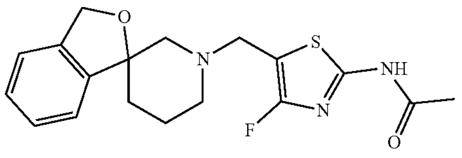 [SMILES: CC(=O)Nc1nc(F)c(CN2CCCC3(C2)OCc2ccccc23)s1]

The title compound was prepared in an analogous manner of that in Example 1 from 3H-spiro[isobenzofuran-1,3'-piperidine] and N-(4-fluoro-5-formylthiazol-2-yl)acetamide. $^1$H NMR (400 MHz, METHANOL-$d_4$) δ 7.19-7.39 (m, 4H), 5.00-5.09 (m, 2H), 3.69 (d, J=0.75 Hz, 2H), 2.75-2.89 (m, 1H), 2.69 (d, J=11.55 Hz, 1H), 2.36-2.51 (m, 2H), 2.19 (s, 3H), 1.92-2.03 (m, 1H), 1.65-1.81 (m, 3H). LCMS (ESI): [M+H] 362.

Example 57: N-(5-((3H-Spiro[isobenzofuran-1,3'-pyrrolidin]-1'-yl)methyl)thiazol-2-yl)acetamide

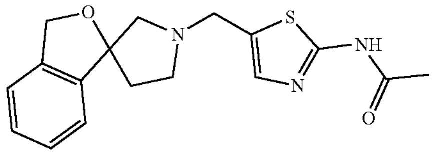 [SMILES: CC(=O)Nc1ncc(CN2CCC3(C2)OCc2ccccc23)s1]

The title compound was prepared in an analogous manner of that Example 2 from 3H-spiro[isobenzofuran-1,3'-pyrrolidine] and N-(5-(chloromethyl)thiazol-2-yl)acetamide. $^1$H NMR (400 MHz, METHANOL-$d_4$) δ 7.16-7.39 (m, 5H), 4.98-5.04 (m, 2H), 3.90 (dd, J=0.88, 1.63 Hz, 2H), 2.78-3.04 (m, 4H), 2.10-2.33 (m, 2H), 2.22 (s, 3H). LCMS (ESI): [M+H] 330.

Example 58: N-(4-Fluoro-5-(((5'S)-5'-methyl-3H-spiro[isobenzofuran-1,3'-pyrrolidin]-1'-yl)methyl)thiazol-2-yl)acetamide

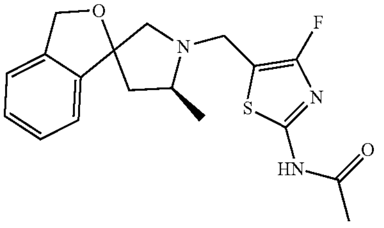

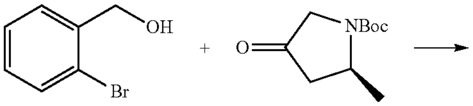

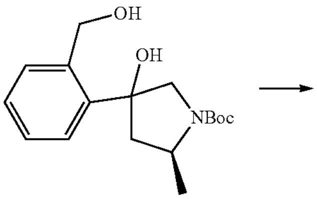

58.1

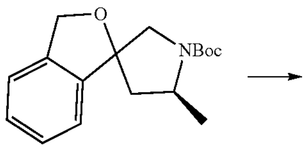

58.2

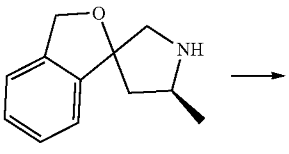

58.3

-continued

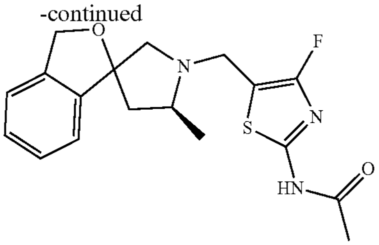

58

Compound 58.1: tert-Butyl (2S)-4-hydroxy-4-(2-(hydroxymethyl)phenyl)-2-methylpyrrolidine-1-carboxylate: n-BuLi (2.5M in hexanes, 18 ml, 45.0 mmol) was added dropwise to a solution of (2-bromophenyl) methanol (4.0 g, 21.40 mmol) in THF (50 ml) at −78° C. and the resulting mixture was stirred at −78° C. for 1 h. To the mixture, a solution of tert-butyl (S)-2-methyl-4-oxopyrrolidine-1-carboxylate (4.25 g, 21.40 mmol) in THF (15 ml) was dropwise added and the mixture was stirred at −78° C. for 30 min before warm-up to rt overnight. The reaction was then quenched by aq. $NH_4Cl$, extracted with EtOAc (3×). The combined organic layer was washed with water, brine, then dried and concentrated. The crude was purified by chromatography on silica gel (50% EtOAc in hexane) to give the title compound (2.0 g, 30% yield). LCMS (ESI): [M+H] 308.

Compound 58.2: tert-Butyl (5'S)-5'-methyl-3H-spiro[isobenzofuran-1,3'-pyrrolidine]-1'-carboxylate: MsCl (0.56 ml, 7.17 mmol) was dropwise added to a solution of tert-butyl (2S)-4-hydroxy-4-(2-(hydroxymethyl)phenyl)-2-methylpyrrolidine-1-carboxylate (2.0 g, 6.50 mmol) and TEA (2.3 ml, 16.29 mmol) in EtOAc (55 ml) at 0° C. and the resulting suspension was stirred at rt overnight. Water was added and the reaction was extracted with EtOAc (3×). The combined organic layer was then washed with water, brine, then dried and concentrated. The crude was purified by chromatography on silica gel (10-20% EtOAc in hexane) to give the title compound (1.30 g, 69% yield). $^1$H NMR (400 MHz, CHLOROFORM-d) δ 7.28-7.35 (m, 2H), 7.20-7.26 (m, 1H), 7.13-7.20 (m, 1H), 5.07-5.13 (m, 2H), 4.03-4.38 (m, 1H), 3.74 (br d, J=12.05 Hz, 1H), 3.60 (br s, 1H), 2.39 (dd, J=8.66, 13.43 Hz, 1H), 1.99 (td, J=1.73, 13.36 Hz, 1H), 1.42-1.52 (m, 12H); LCMS (ESI): [M+H] 290.

Compound 58.3: (5'S)-5'-Methyl-3H-spiro[isobenzofuran-1,3'-pyrrolidine]:

The title compound was prepared in an analogous manner of that in Compound 1.3 from tert-butyl (5'S)-5'-methyl-3H-spiro[isobenzofuran-1,3'-pyrrolidine]-1'-carboxylate. LCMS (ESI): [M+H] 190.

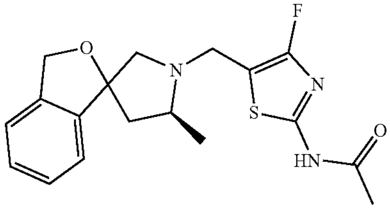 [SMILES: CC(=O)Nc1nc(F)c(CN2CC3(C[C@@H]2C)OCc2ccccc23)s1]

The title compound was prepared in an analogous manner of that in Example 1 from (5'S)-5'-methyl-3H-spiro[isobenzofuran-1,3'-pyrrolidine] and N-(4-fluoro-5-formyl-thiazol-2-yl). $^1$H NMR (400 MHz, METHANOL-$d_4$) δ 7.24-7.32 (m, 2H), 7.15-7.24 (m, 2H), 4.93-5.05 (m, 2H), 3.96-4.05 (m, 1H), 3.67 (d, J=14.56 Hz, 1H), 3.22 (d, J=10.29 Hz, 1H), 2.78-2.92 (m, 1H), 2.55 (d, J=10.54 Hz, 1H), 2.43 (dd, J=7.91, 13.93 Hz, 1H), 2.18 (s, 3H), 1.96-2.04 (m, 1H), 1.29 (d, J=6.27 Hz, 3H). LCMS (ESI): [M+H] 362.

Example 59: N-(5-(((5'S)-5'-Methyl-3H-spiro[isobenzofuran-1,3'-pyrrolidin]-1'-yl)methyl)thiazol-2-yl)acetamide

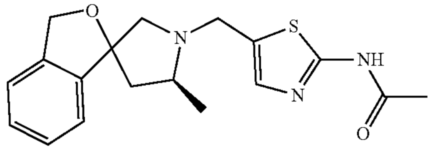 [SMILES: CC(=O)Nc1ncc(CN2CC3(C[C@@H]2C)OCc2ccccc23)s1]

The title compound was prepared in an analogous manner of that in Example 2 from (5'S)-5'-methyl-3H-spiro[isobenzofuran-1,3'-pyrrolidine] and N-[5-(chloromethyl)thiazol-2-yl]. $^1$H NMR (400 MHz, METHANOL-$d_4$) δ δ 7.23-7.31 (m, 3H), 7.16-7.23 (m, 2H), 4.90-5.05 (m, 2H), 4.16 (dd, J=0.88, 14.18 Hz, 1H), 3.64 (d, J=14.31 Hz, 1H), 3.19 (d, J=10.29 Hz, 1H), 2.74-2.91 (m, 1H), 2.50 (d, J=10.54 Hz, 1H), 2.42 (dd, J=7.78, 13.80 Hz, 1H), 2.20 (s, 3H), 2.01 (ddd, J=1.25, 8.72, 13.87 Hz, 1H), 1.29 (d, J=6.02 Hz, 3H). LCMS (ESI): [M+H] 344.

Example 60: N-(5-((6'-Methyl-3H-spiro[isobenzofuran-1,3'-piperidin]-1'-yl)methyl)thiazol-2-yl)acetamide

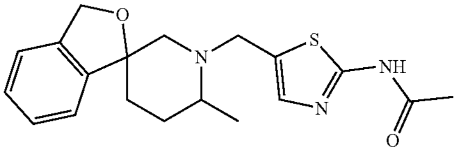 [SMILES: CC(=O)Nc1ncc(CN2CC3(CCC2C)OCc2ccccc23)s1]

The title compound was prepared in an analogous manner of that in Example 59 from (2-bromophenyl) methanol, tert-butyl 2-methyl-5-oxopiperidine-1-carboxylate and N-(5-(chloromethyl)thiazol-2-yl)acetamide. $^1$H NMR (400 MHz, METHANOL-$d_4$) δ δ 7.52-7.65 (m, 1H), 7.14-7.30 (m, 4H), 4.92-5.10 (m, 2H), 3.92-4.03 (m, 1H), 3.72 (d, J=14.56 Hz, 1H), 2.81 (d, J=11.04 Hz, 1H), 2.65-2.75 (m, 1H), 2.71 (br s, 1H), 2.42 (d, J=11.80 Hz, 1H), 2.17 (s, 3H), 1.86-2.01 (m, 2H), 1.53-1.75 (m, 2H), 1.15-1.34 (m, 3H). LCMS (ESI): [M+H] 358.

Example 61: N-(5-((5H-Spiro[furo[3,4-b]pyridine-7,3'-piperidin]-1'-yl)methyl)-4-fluorothiazol-2-yl)acetamide

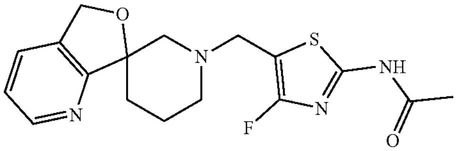 [SMILES: CC(=O)Nc1nc(F)c(CN2CCCC3(C2)OCc2cccnc23)s1]

The title compound was prepared in an analogous manner of that in Example 58 from (2-bromopyridin-3-yl) methanol, tert-butyl 3-oxopiperidine-1-carboxylate and N-(4-fluoro-5-formylthiazol-2-yl)acetamide. $^1$H NMR (400 MHz, METHANOL-$d_4$) δ 8.34-8.46 (m, 1H), 7.75 (qd, J=1.13, 7.65 Hz, 1H), 7.32 (dd, J=5.02, 7.78 Hz, 1H), 5.08 (d, J=0.75 Hz, 2H), 3.63-3.79 (m, 2H), 2.89-3.05 (m, 1H), 2.78 (d, J=11.80 Hz, 1H), 2.47 (d, J=11.55 Hz, 1H), 2.21-2.35 (m, 1H), 2.17 (s, 3H), 2.04-2.10 (m, 1H), 1.65-1.88 (m, 3H). LCMS (ESI): [M+H] 363.

Example 62: N-(5-(((5'S)-5'-Methyl-5H-spiro[furo[3,4-b]pyridine-7,3'-pyrrolidin]-1'-yl)methyl)thiazol-2-yl)acetamide

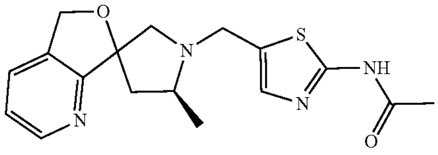 [SMILES: CC(=O)Nc1ncc(CN2CC3(C[C@@H]2C)OCc2cccnc23)s1]

The title compounds were prepared in an analogous manner of that in Example 59 from (2-bromopyridin-3-yl) methanol, tert-butyl (S)-2-methyl-4-oxopyrrolidine-1-carboxylate and N-(5-(chloromethyl)thiazol-2-yl)acetamide. $^1$H NMR (400 MHz, METHANOL-$d_4$) δ 8.44 (dd, J=1.25, 5.02 Hz, 1H), 7.71 (dd, J=1.25, 7.78 Hz, 1H), 7.30 (dd, J=5.02, 7.53 Hz, 1H), 7.25 (s, 1H), 5.01 (q, J=13.22 Hz, 2H), 4.18 (dd, J=0.75, 14.31 Hz, 1H), 3.64 (d, J=14.05 Hz, 1H), 3.18 (d, J=10.29 Hz, 1H), 2.82-2.93 (m, 1H), 2.60 (d, J=10.54 Hz, 1H), 2.52 (dd, J=7.78, 13.80 Hz, 1H), 2.19 (s, 3H), 1.94-2.00 (m, 1H), 1.30 (d, J=6.27 Hz, 3H); LCMS (ESI): [M+H] 345.

Example 63: N-(4-Fluoro-5-(((5'S)-5'-methyl-5H-spiro[furo[3,4-b]pyridine-7,3'-pyrrolidin]-1'-yl)methyl)thiazol-2-yl)acetamide

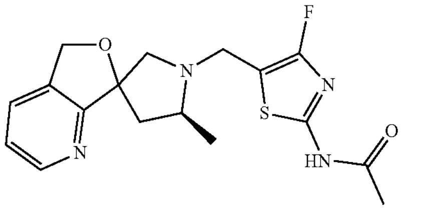 [SMILES: CC(=O)Nc1nc(F)c(CN2CC3(C[C@@H]2C)OCc2cccnc23)s1]

The title compounds were prepared in an analogous manner of that in Example 58 from (2-bromopyridin-3-yl) methanol, tert-butyl (S)-2-methyl-4-oxopyrrolidine-1-carboxylate and N-(5-(chloromethyl)-4-fluorothiazol-2-yl)acetamide. $^1$H NMR (400 MHz, METHANOL-$d_4$) δ 8.43 (dd, J=1.51, 5.02 Hz, 1H), 7.72 (dd, J=1.38, 7.65 Hz, 1H); 7.30 (dd, J=5.02, 7.78 Hz, 1H), 4.97-5.09 (m, 2H), 4.02 (d, J=14.31 Hz, 1H), 3.68 (d, J=14.56 Hz, 1H), 3.21 (d, J=10.29 Hz, 1H), 2.83-2.95 (m, 1H), 2.66 (d, J=10.29 Hz, 1H), 2.52 (dd, J=8.03, 13.80 Hz, 1H), 2.18 (s, 3H), 1.95 (ddd, J=1.25, 8.78, 13.80 Hz, 1H), 1.29 (d, J=6.02 Hz, 3H); LCMS (ESI): [M+H] 363.

Example 64: N-(4-Fluoro-5-(((1S,5'S)-5'-methyl-3H-spiro[furo[3,4-c]pyridine-1,3'-pyrrolidin]-1'-yl)methyl)thiazol-2-yl)acetamide and N-(4-fluoro-5-(((1R,5'S)-5'-methyl-3H-spiro[furo[3,4-c]pyridine-1,3'-pyrrolidin]-1'-yl)methyl)thiazol-2-yl)acetamide

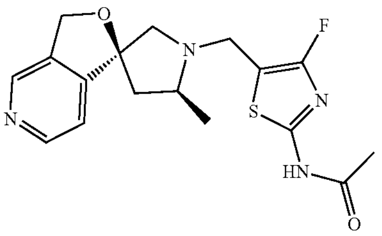

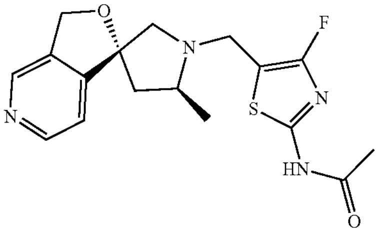

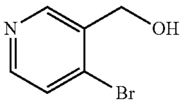

+

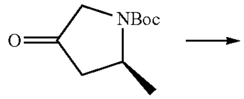

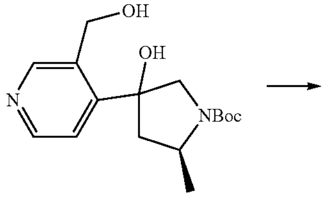

64.1

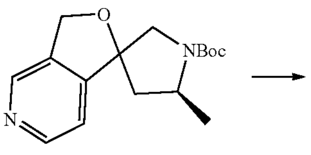

64.2

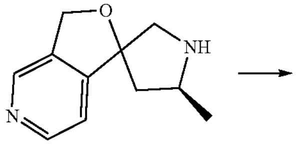

64.3

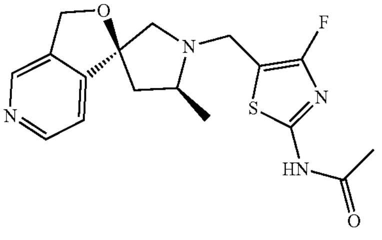

+

64a

-continued

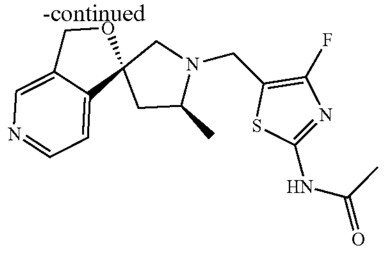

64b

Compound 64.1: tert-Butyl (2S)-4-hydroxy-4-(3-(hydroxymethyl)pyridin-4-yl)-2-methylpyrrolidine-1-carboxylate: n-BuLi (2.5M in hexanes, 13.1 ml, 32.76 mmol) was added dropwise to a solution of (4-bromopyridin-3-yl) methanol (2.80 g, 14.89 mmol) in THF (30 mL) at −78° C. and the resulting mixture was stirred at −78° C. for 2 h. To the mixture, a solution of tert-butyl (S)-2-methyl-4-oxopyrrolidine-1-carboxylate (2.96 g, 14.89 mmol) in THF (10 mL) was dropwise added and the mixture was stirred at −78° C. for 30 min and then stirred at rt overnight. The reaction was quenched with aq. $NH_4Cl$, the product was extracted with EtOAc (3×). The combined organic layer was washed with water, brine, then dried and concentrated. The crude was purified by chromatography on silica gel to give the title compound (1.63 g, 35.5% yield). LCMS (ESI): [M+H] 309.

Compound 64.2: tert-Butyl (5'S)-5'-methyl-3H-spiro[furo[3,4-c]pyridine-1,3'-pyrrolidine]-1'-carboxylate: n-BuLi (2.5M in hexanes, 4.23 ml, 10.60 mmol) was added at −78° C. to a stirred solution of tert-butyl (2S)-4-hydroxy-4-(3-(hydroxymethyl)pyridin-4-yl)-2-methylpyrrolidine-1-carboxylate (1.63 g, 5.30 mmol) in THF (24 mL). The reaction was then stirred at −78° C. for 1 h. A solution of p-toluenesulfonyl chloride (1.11 g, 5.82 mmol) in THF (5 mL) was added and the resulting mixture was stirred at rt overnight. The mixture was then poured into aq. $NH_4Cl$. The product was extracted with EtOAc (2×). The combined organic layer was washed with brine, dried, and concentrated. The crude product was purified by column chromatography on silica gel to give the title compound (600 mg, 39% yield). LCMS (ESI): [M+H] 291.

Compound 64.3: (5'S)-5'-Methyl-3H-spiro[furo[3,4-c]pyridine-1,3'-pyrrolidine]: The title compound was prepared in an analogous manner of that in Compound 31.2 from tert-butyl (2'S)-2'-methylspiro[3H-furo[3,4-c]pyridine-1,4'-pyrrolidine]-1'-carboxylate. LCMS (ESI): [M+H] 191.

The title compounds were prepared in an analogous manner of that in Example 31 from (5'S)-5'-methyl-3H-spiro[furo[3,4-c]pyridine-1,3'-pyrrolidine] and N-(5-(chloromethyl)-4-fluorothiazol-2-yl)acetamide. Two diastereomers were obtained after HPLC (the chiral center on the quaternary carbon was randomly assigned): P1: $^1$H NMR (400 MHz, METHANOL-$d_4$) δ 8.75 (br s, 2H), 7.91 (d, J=5.52 Hz, 1H), 5.21-5.37 (m, 2H), 4.75 (d, J=14.56 Hz, 1H), 4.54 (d, J=14.56 Hz, 1H), 3.96-4.15 (m, 1H), 3.89 (dd, J=1.63, 11.92 Hz, 1H), 3.64 (d, J=11.80 Hz, 1H), 2.99 (dd, J=9.66, 14.43 Hz, 1H), 2.26-2.40 (m, 1H), 2.21 (s, 3H), 1.61 (d, J=6.78 Hz, 3H); LCMS (ESI): [M+H] 363; and P2: $^1$H NMR (400 MHz, METHANOL-$d_4$) δ 8.70 (br s, 2H), 7.74 (d, J=5.27 Hz, 1H), 5.21-5.34 (m, 2H), 4.76 (d, J=14.81 Hz, 1H), 4.60 (d, J=14.56 Hz, 1H), 3.96-4.16 (m, 2H), 3.73 (dd, J=1.76, 13.30 Hz, 1H), 2.64-2.72 (m, 1H), 2.23-2.32 (m, 1H), 2.22 (s, 3H), 1.58 (d, J=6.53 Hz, 3H); LCMS (ESI): [M+H] 363.

Example 65: N-(5-(((1S,5'S)-5'-Methyl-3H-spiro[furo[3,4-c]pyridine-1,3'-pyrrolidin]-1'-yl)methyl)thiazol-2-yl)acetamide and N-(5-(((1R,5'S)-5'-methyl-3H-spiro[furo[3,4-c]pyridine-1,3'-pyrrolidin]-1'-yl)methyl)thiazol-2-yl)acetamide

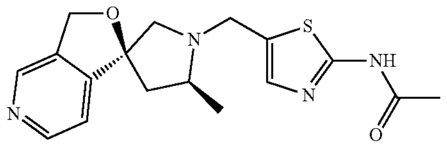

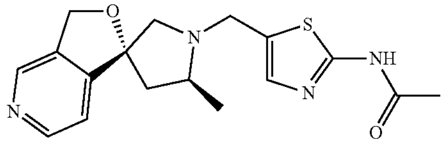

The title compound was prepared in an analogous manner of that in Example 64 from (5'S)-5'-methyl-3H-spiro[furo[3,4-c]pyridine-1,3'-pyrrolidine] and N-(5-(chloromethyl)thiazol-2-yl)acetamide. The two isomers were separated by HPLC. The chiral center on the quaternary carbon was randomly assigned. P1: $^1$H NMR (400 MHz, METHANOL-$d_4$) δ 8.77 (br d, J=9.04 Hz, 2H), 7.90-8.00 (m, 1H), 7.61-7.71 (m, 1H), 5.17-5.40 (m, 2H), 4.91 (br s, 1H), 4.54-4.75 (m, 1H), 3.97-4.18 (m, 1H), 3.76-3.88 (m, 1H), 3.68 (d, J=12.30 Hz, 1H), 2.98 (dd, J=9.66, 14.43 Hz, 1H), 2.28-2.44 (m, 1H), 2.22 (s, 3H), 1.54-1.64 (m, 3H); LCMS (ESI): [M+H] 345; P2: $^1$H NMR (400 MHz, METHANOL-$d_4$) δ 8.64-8.78 (m, 2H), 7.82 (d, J=5.52 Hz, 1H), 7.68 (s, 1H), 5.22-5.37 (m, 2H), 4.92 (br s, 1H), 4.69 (d, J=14.05 Hz, 1H), 4.11 (td, J=5.96, 12.17 Hz, 1H), 3.98 (d, J=13.30 Hz, 1H), 3.80 (dd, J=1.76, 13.30 Hz, 1H), 2.70 (ddd, J=1.63, 5.71, 13.99 Hz, 1H), 2.29 (dd, J=11.92, 13.93 Hz, 1H), 2.22 (s, 3H), 1.56 (d, J=6.53 Hz, 3H); LCMS (ESI): [M+H] 345.

Example 66: N-(5-((3H-Spiro[furo[3,4-c]pyridine-1,3'-pyrrolidin]-1'-yl)methyl)thiazol-2-yl)acetamide

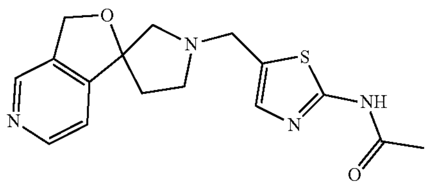 [SMILES: CC(=O)Nc1ncc(CN2CCC3(C2)OCc2cnccc23)s1]

The title compound was prepared in an analogous manner of that in Example 64 from 3H-spiro[furo[3,4-c]pyridine-1,3'-pyrrolidine] and N-(5-(chloromethyl)thiazol-2-yl)acetamide. $^1$H NMR (400 MHz, METHANOL-$d_4$) δ 8.79 (br·s, 2H), 7.97 (d, J=5.52 Hz, 1H), 7.65 (s, 1H), 5.31 (s, 2H), 4.71-4.82 (m, 2H), 3.70-3.89 (m, 4H), 2.51-2.73 (m, 2H), 2.20-2.27 (m, 3H); LCMS (ESI): [M+H] 331.

Example 67: N-(5-((3H-Spiro[furo[3,4-c]pyridine-1,3'-pyrrolidin]-1'-yl)methyl)-4-fluorothiazol-2-yl) acetamide

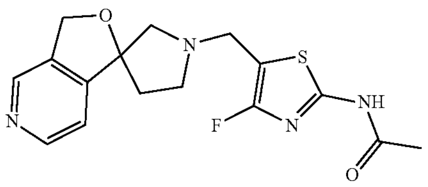 [SMILES: CC(=O)Nc1nc(F)c(CN2CCC3(C2)OCc2cnccc23)s1]

The title compound was prepared in an analogous manner of that in Example 64 from 3H-spiro[furo[3,4-c]pyridine-1,3'-pyrrolidine] and N-(5-(chloromethyl)-4-fluorothiazol-2-yl)acetamide. $^1$H NMR (400 MHz, METHANOL-$d_4$) δ 8.75-8.91 (m, 2H), 8.07 (d, J=5.77 Hz, 1H), 5.32 (s, 2H), 4.59-4.74 (m, 2H), 3.71-3.92 (m, 4H), 2.52-2.76 (m, 2H), 2.21 (s, 3H); LCMS (ESI): [M+H] 349.

Example 68: N-(5-((3H-Spiro[furo[3,4-c]pyridine-1,3'-piperidin]-1'-yl)methyl)thiazol-2-yl)acetamide

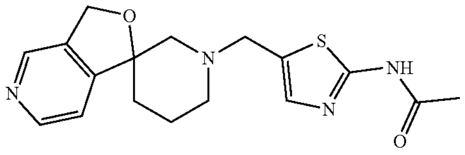 [SMILES: CC(=O)Nc1ncc(CN2CCCC3(C2)OCc2cnccc23)s1]

The title compound was prepared in an analogous manner of that in Example 64 from (4-bromopyridin-3-yl) methanol, tert-butyl 3-oxopiperidine-1-carboxylate and N-(5-(chloromethyl)thiazol-2-yl)acetamide. $^1$H NMR (400 MHz, METHANOL-$d_4$) δ 8.42-8.49 (m, 2H), 7.58 (d, J=5.02 Hz, 1H), 7.21 (s, 1H), 5.05-5.18 (m, 2H), 3.77 (s, 2H), 2.52-2.70 (m, 4H), 2.19 (s, 3H), 1.56-2.00 (m, 4H). LCMS (ESI): [M+H] 345.

Example 69: N-(5-((3H-Spiro[furo[3,4-c]pyridine-1,3'-piperidin]-1'-yl)methyl)-4-fluorothiazol-2-yl)acetamide

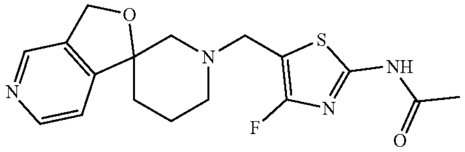

The title compound was prepared in an analogous manner of that in Example 1 from 3H-spiro[furo[3,4-c]pyridine-1,3'-piperidine] (prepared similarly as described in Compound 64.3) and N-(4-fluoro-5-formylthiazol-2-yl)acetamide. $^1$H NMR (400 MHz, METHANOL-$d_4$) δ 8.36-8.54 (m, 2H), 7.55 (d, J=4.77 Hz, 1H), 5.02-5.19 (m, 2H), 3.67 (dd, J=0.75, 3.01 Hz, 2H), 2.50-2.77 (m, 4H), 2.17 (s, 3H), 1.86-1.95 (m, 1H), 1.65-1.84 (m, 3H). LCMS (ESI): [M+H] 363.

Example 70: (R)—N-(5-((3H-Spiro[furo[3,4-c]pyridine-1,3'-piperidin]-1'-yl)methyl)-4-fluorothiazol-2-yl)acetamide and(S)—N-(5-((3H-spiro[furo[3,4-c]pyridine-1,3'-piperidin]-1'-yl)methyl)-4-fluorothiazol-2-yl)acetamide

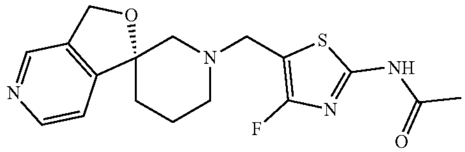 [SMILES: CC(=O)Nc1nc(F)c(CN2CCCC3(C2)OCc2cnccc23)s1]

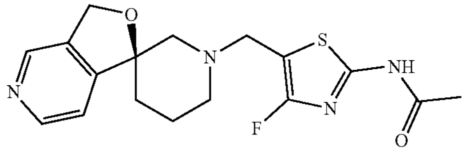

rac-N-(5-((3H-spiro[furo[3,4-c]pyridine-1,3'-piperidin]-1'-yl)methyl)-4-fluorothiazol-2-yl)acetamide (Example 69, 74 mg) was purified by SFC (using a Chiralpak AD-H, 30×250 mm column, 5 μm, 40% MeOH (containing 0.1% $Et_2NH$) in $CO_2$ as the mobile phase, flow rate of 100 mL/min, ABPR 120 bar, MBPR 40 psi, column temperature of 40° C.) to give in order of elution:

Peak 1 (absolute stereochemistry was arbitrarily assigned), (R)—N-(5-((3H-spiro[furo[3,4-c]pyridine-1,3'-piperidin]-1'-yl)methyl)-4-fluorothiazol-2-yl)acetamide (25 mg). $^1$H NMR (400 MHz, METHANOL-$d_4$) δ 8.39-8.52 (m, 2H), 7.55 (d, J=5.02 Hz, 1H), 5.05-5.20 (m, 2H), 3.54-3.76 (m, 2H), 2.46-2.70 (m, 4H), 2.17 (s, 3H), 1.87-1.98 (m, 1H), 1.68-1.82 (m, 3H). LCMS (ESI): [M+H] 363.

Peak 2 (absolute stereochemistry was arbitrarily assigned), (S)—N-(5-((3H-spiro[furo[3,4-c]pyridine-1,3'-piperidin]-1'-yl)methyl)-4-fluorothiazol-2-yl)acetamide (25 mg). $^1$H NMR (400 MHz, METHANOL-$d_4$) δ 8.37-8.53 (m, 2H), 7.55 (d, J=5.02 Hz, 1H), 5.01-5.19 (m, 2H), 3.54-3.76 (m, 2H), 2.50-2.70 (m, 4H), 2.17 (s, 3H), 1.85-1.99 (m, 1H), 1.69-1.82 (m, 3H). LCMS (ESI): [M+H] 363.

Example 71: N-(5-(((3S,5'S)-5'-Methyl-1H-spiro[furo[3,4-c]pyridine-3,3'-pyrrolidin]-1'-yl)methyl)thiazol-2-yl)acetamide and N-(5-(((3R,5'S)-5'-methyl-1H-spiro[furo[3,4-c]pyridine-3,3'-pyrrolidin]-1'-yl)methyl)thiazol-2-yl)acetamide

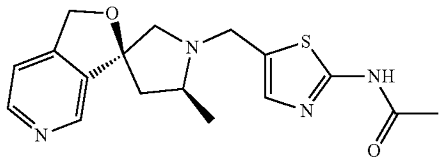

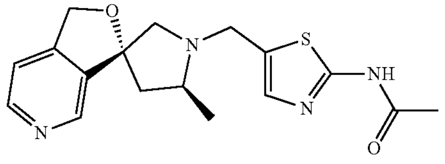

The title compounds were prepared in an analogous manner of that in Example 64 from (3-bromopyridin-4-yl) methanol, tert-butyl (S)-2-methyl-4-oxopyrrolidine-1-carboxylate and N-(5-(chloromethyl)thiazol-2-yl)acetamide. The two diastereomers were separated by HPLC. The chiral center on the quaternary carbon was randomly assigned. P1: $^1$H NMR (400 MHz, METHANOL-$d_4$) δ 8.82 (s, 1H), 8.69 (d, J=5.52 Hz, 1H), 7.71 (d, J=5.52 Hz, 1H), 7.64 (s, 1H), 5.16-5.35 (m, 2H), 4.88-4.92 (m, 1H), 4.54-4.68 (m, 1H), 3.99-4.15 (m, 1H), 3.74-3.85 (m, 1H), 3.60-3.73 (m, 1H), 2.99 (dd, J=9.66, 14.18 Hz, 1H), 2.29-2.42 (m, 1H), 2.20-2.25 (m, 3H), 1.59 (d, J=6.78 Hz, 3H); LCMS (ESI): [M+H] 345. P2: $^1$H NMR (400 MHz, METHANOL-$d_4$) δ 8.73 (s, 1H), 8.64 (d, J=5.27 Hz, 1H), 7.68 (s, 1H), 7.64 (d, J=5.52 Hz, 1H), 5.18-5.34 (m, 2H), 4.79-4.83 (m, 1H), 4.69 (d, J=14.31 Hz, 1H), 4.12 (br s, 1H), 3.92-4.01 (m, 1H), 3.78 (br d, J=14.31 Hz, 1H), 2.66-2.76 (m, 1H), 2.31 (br t, J=12.67 Hz, 1H), 2.22 (s, 3H), 1.55 (d, J=6.27 Hz, 3H); LCMS (ESI): [M+H] 345.

Example 72: N-(4-Fluoro-5-(((3S,5'S)-5'-methyl-1H-spiro[furo[3,4-c]pyridine-3,3'-pyrrolidin]-1'-yl)methyl)thiazol-2-yl)acetamide and N-(4-fluoro-5-(((3R,5'S)-5'-methyl-1H-spiro[furo[3,4-c]pyridine-3,3'-pyrrolidin]-1'-yl)methyl)thiazol-2-yl)acetamide

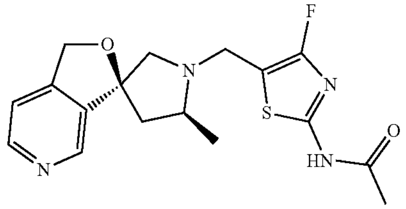

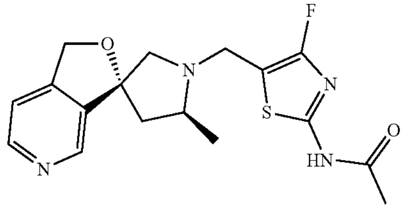

The title compounds were prepared in an analogous manner of that in Example 64 from (3-bromopyridin-4-yl)methanol, tert-butyl (S)-2-methyl-4-oxopyrrolidine-1-carboxylate and N-(5-(chloromethyl)-4-fluorothiazol-2-yl)acetamide. The two isomers were separated by HPLC. The chiral center on the quaternary carbon was randomly assigned. P1: $^1$H NMR (400 MHz, METHANOL-$d_4$) δ 8.87 (s, 1H), 8.72 (d, J=5.52 Hz, 1H), 7.76 (d, J=5.27 Hz, 1H), 5.20-5.38 (m, 2H), 4.75 (d, J=14.56 Hz, 1H), 4.54 (d, J=14.56 Hz, 1H), 4.00-4.15 (m, 1H), 3.89 (dd, J=1.88, 11.92 Hz, 1H), 3.65 (d, J=12.05 Hz, 1H), 3.01 (dd, J=9.79, 14.31 Hz, 1H), 2.29-2.40 (m, 1H), 2.21 (s, 3H), 1.61 (d, J=6.78 Hz, 3H); LCMS (ESI): [M+H] 363. P2: $^1$H NMR (400 MHz, METHANOL-$d_4$) δ 8.81 (br s, 1H), 8.69 (br d, J=4.27 Hz, 1H), 7.73 (d, J=5.27 Hz, 1H), 5.18-5.38 (m, 2H), 4.76 (br d, J=14.56 Hz, 1H), 4.57-4.65 (m, 1H), 4.00-4.15 (m, 2H), 3.74 (dd, J=1.76, 13.30 Hz, 1H), 2.72 (br d, J=4.27 Hz, 1H), 2.28-2.40 (m, 1H), 2.22 (s, 3H), 1.58 (d, J=6.78 Hz, 3H); LCMS (ESI): [M+H] 363.

Example 73: N-(5-((1H-Spiro[furo[3,4-c]pyridine-3,3'-piperidin]-1'-yl)methyl)-4-fluorothiazol-2-yl)acetamide

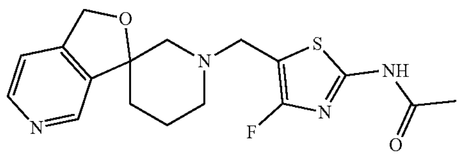 [SMILES: CC(=O)Nc1nc(F)c(CN2CCCC3(C2)OCc2ccncc23)s1]

The title compound was prepared in an analogous manner of that in Example 1 from 1H-spiro[furo[3,4-c]pyridine-3,3'-piperidine] (prepared in the similar way as described in Compound 64.3) and N-(4-fluoro-5-formylthiazol-2-yl)acetamide. $^1$H NMR (400 MHz, METHANOL-$d_4$) δ 8.64 (s, 1H), 8.44 (d, J=5.02 Hz, 1H), 7.37 (qd, J=0.99, 5.05 Hz, 1H), 5.00-5.15 (m, 2H), 3.60-3.74 (m, 2H), 2.51-2.69 (m, 4H), 2.16 (s, 3H), 1.86-1.97 (m, 1H), 1.66-1.83 (m, 3H). LCMS (ESI): [M+H] 363.

Example 74: N-(5-((1H-Spiro[furo[3,4-c]pyridine-3,3'-piperidin]-1'-yl)methyl)thiazol-2-yl)acetamide

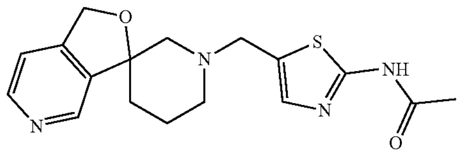 [SMILES: CC(=O)Nc1ncc(CN2CCCC3(C2)OCc2ccncc23)s1]

The title compound was prepared in an analogous manner of that in Example 2 from 1H-spiro[furo[3,4-c]pyridine-3,3'-piperidine] (prepared in the similar way as described in Compound 64.3) and N-(5-(chloromethyl)thiazol-2-yl)acetamide. $^1$H NMR (400 MHz, METHANOL-$d_4$) δ 8.65 (s, 1H), 8.34-8.50 (m, 1H), 7.32-7.41 (m, 1H), 7.12-7.24 (m, 1H), 4.98-5.18 (m, 2H), 3.69-3.85 (m, 2H), 2.48-2.75 (m, 4H), 2.17 (s, 3H), 1.86-2.00 (m, 1H), 1.64-1.82 (m, 3H). LCMS (ESI): [M+H] 345.

Example 75: N-(4-Fluoro-5-(((3S,5'S)-6-methoxy-5'-methyl-1H-spiro[furo[3,4-c]pyridine-3,3'-pyrrolidin]-1'-yl)methyl)thiazol-2-yl)acetamide and N-(4-fluoro-5-(((3R,5'S)-6-methoxy-5'-methyl-1H-spiro[furo[3,4-c]pyridine-3,3'-pyrrolidin]-1'-yl)methyl)thiazol-2-yl)acetamide

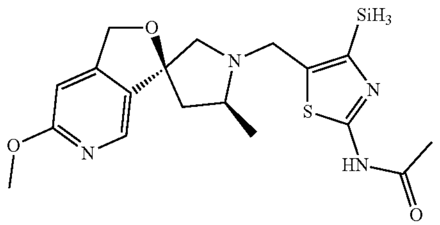

-continued

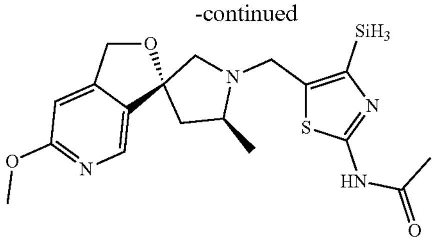

The title compounds were prepared in an analogous manner of that in Example 64 from (5-bromo-2-methoxy-pyridin-4-yl) methanol, tert-butyl (S)-2-methyl-4-oxopyrrolidine-1-carboxylate and N-(5-(chloromethyl)-4-fluorothiazol-2-yl)acetamide. The two diastereomers were separated by HPLC. The chiral center on the quaternary carbon was randomly assigned.

P1: $^1$H NMR (400 MHz, METHANOL-$d_4$) δ 8.19 (s, 1H), 6.76 (d, J=0.75 Hz, 1H), 5.00-5.13 (m, 2H), 4.71 (d, J=14.56 Hz, 1H), 4.52 (d, J=14.81 Hz, 1H), 3.97-4.09 (m, 1H), 3.93 (s, 3H), 3.76 (dd, J=1.88, 11.67 Hz, 1H), 3.54 (br d, J=11.80 Hz, 1H), 2.92 (br dd, J=10.16, 13.93 Hz, 1H), 2.21 (s, 4H), 1.58 (d, J=6.78 Hz, 3H); LCMS (ESI): [M+H] 393.

P2: $^1$H NMR (400 MHz, METHANOL-$d_4$) δ 8.14 (s, 1H), 6.76 (s, 1H), 5.02-5.14 (m, 2H), 4.68-4.81 (m, 1H), 4.53-4.65 (m, 1H), 3.98-4.15 (m, 1H), 3.81-3.96 (m, 4H), 3.67 (dd, J=1.76, 13.30 Hz, 1H), 2.62 (br dd, J=4.77, 13.80 Hz, 1H), 2.14-2.28 (m, 4H), 1.55 (d, J=6.53 Hz, 3H); LCMS (ESI): [M+H] 393.

Example 76: N-(5-(((3S,5'S)-6-Methoxy-5'-methyl-1H-spiro[furo[3,4-c]pyridine-3,3'-pyrrolidin]-1'-yl)methyl)thiazol-2-yl)acetamide and N-(5-(((3R,5'S)-6-methoxy-5'-methyl-1H-spiro[furo[3,4-c]pyridine-3,3'-pyrrolidin]-1'-yl)methyl)thiazol-2-yl)acetamide

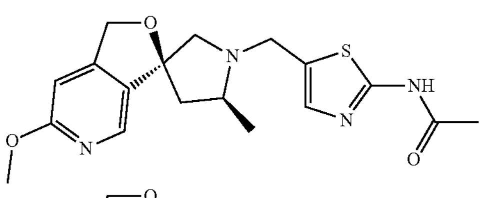

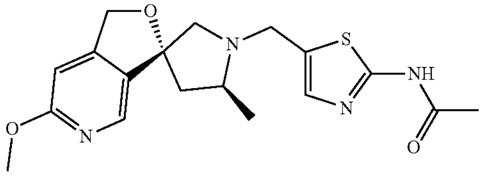

The title compounds were prepared in an analogous manner of that in Example 64 from (5-bromo-2-methoxy-pyridin-4-yl) methanol, tert-butyl (S)-2-methyl-4-oxopyrrolidine-1-carboxylate and N-(5-(chloromethyl)thiazol-2-yl) acetamide. The two diastereomers were separated by HPLC. The chiral center on the quaternary carbon was randomly assigned.

P1: $^1$H NMR (400 MHz, METHANOL-$d_4$) δ 8.18 (s, 1H), 7.64 (s, 1H), 6.75 (s, 1H), 4.99-5.12 (m, 2H), 4.82 (s, 1H), 4.60 (br d, J=14.05 Hz, 1H), 4.03 (br d, J=4.02 Hz, 1H), 3.93 (s, 3H), 3.63-3.72 (m, 1H), 3.51-3.61 (m, 1H), 2.81-2.98 (m, 1H), 2.22 (s, 4H), 1.55 (d, J=6.78 Hz, 3H); LCMS (ESI): [M+H] 375.

P2: $^1$H NMR (400 MHz, METHANOL-$d_4$) δ 8.15 (s, 1H), 7.68 (s, 1H), 6.77 (s, 1H), 5.01-5.16 (m, 2H), 4.92 (br s, 1H), 4.68 (d, J=14.31 Hz, 1H), 4.10 (br d, J=8.53 Hz, 1H), 3.93 (s, 3H), 3.78-3.89 (m, 1H), 3.71 (br d, J=13.05 Hz, 1H), 2.62 (br dd, J=4.52, 13.55 Hz, 1H), 2.17-2.32 (m, 4H), 1.52 (br d, J=6.27 Hz, 3H);); LCMS (ESI): [M+H] 375.

Example 77: N-(4-Fluoro-5-(((5'S)-4-methoxy-5'-methyl-3H-spiro[furo[3,4-c]pyridine-1,3'-pyrrolidin]-1'-yl)methyl)thiazol-2-yl)acetamide

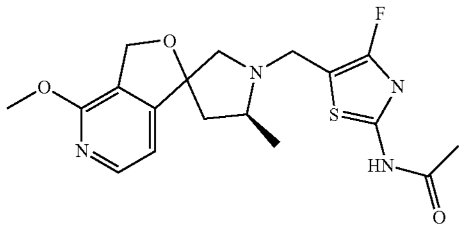

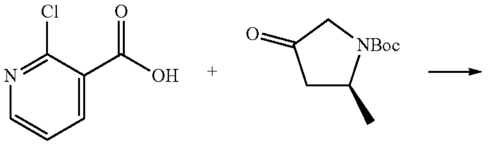

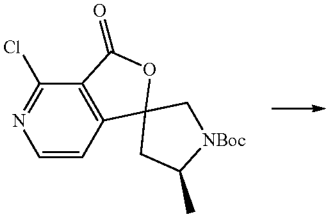

77.1

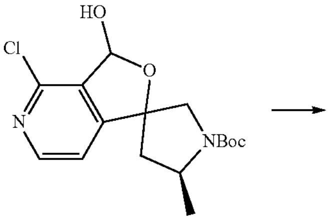

77.2

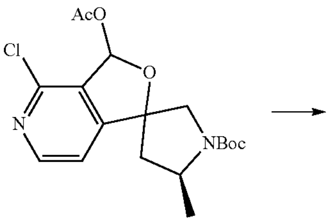

77.3

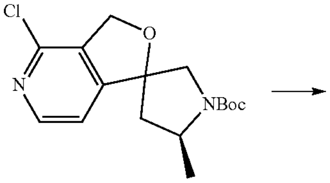

77.4

-continued

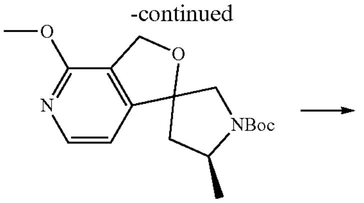

77.5

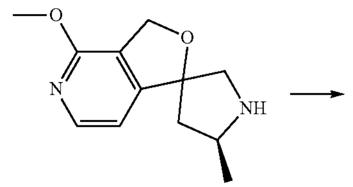

77.6

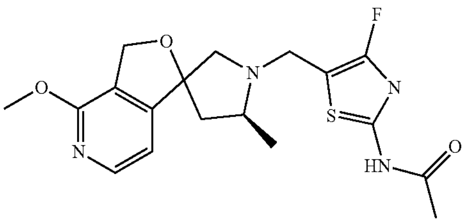

77

Compound 77.1: tert-Butyl (5'S)-4-chloro-5'-methyl-3-oxo-3H-spiro[furo[3,4-c]pyridine-1,3'-pyrrolidine]-1'-carboxylate: A solution of 2,2,6,6-tetramethyl-piperidine (1.39 g, 9.84 mmol) in THF (15 mL) at −78° C. was added n-butyllithium (2.5 M in hexanes, 3.8 mL). After stirred for 1 h, a solution of 2-chloronicotinic acid (500 mg, 3.17 mmol) in THF (10 mL) was added. The mixture was stirred at −78° C. for 1 h. A solution of tert-butyl (S)-2-methyl-4-oxopyrrolidine-1-carboxylate (1.90 g, 9.52 mol) in THF (5 mL) was added to the above mixture. The reaction mixture was stirred at −78° C. for 1 h. The reaction was quenched with water (10 ml) and then warmed up to room temperature and diluted with EtOAc (30 ml). The aqueous layer was separated, and the organic layer was extracted with aqueous 1N sodium hydroxide solution (2×10 mL). The combined aqueous layer was acidified with concentrated hydrochloric acid to pH=1. After stirring for 1 h, the precipitate was filtered, washed with water, and dissolved in EtOAc. The solution was washed with aq. $NaHCO_3$, dried over $Na_2SO_4$ and concentrated under vacuum to give the title compound as white solid (0.69 g, 64% yield). LCMS (ESI): [M+H] 339.

Compound 77.2: tert-Butyl (5'S)-4-chloro-3-hydroxy-5'-methyl-3H-spiro[furo[3,4-c]pyridine-1,3'-pyrrolidine]-1'-carboxylate: Diisobutylaluminium hydride (1.0M in toluene, 4.1 ml, 4.1 mmol,) was dropwise added to a solution of tert-butyl (5'S)-4-chloro-5'-methyl-3-oxo-3H-spiro[furo[3,4-c]pyridine-1,3'-pyrrolidine]-1'-carboxylate (0.69 g, 2.04 mmol) in 20 ml of dry DCM at −78° C. After the solution had been stirred at −78° C. for 1 h, the mixture was poured into aq. $NH_4Cl$ and extracted twice with DCM. The organic layer was washed with brine and concentrated. The crude was purified by column chromatography on silica gel to give the title compound (0.69 g, Yield 100%). LCMS (ESI): [M+H] 341.

Compound 77.3: tert-Butyl (5'S)-3-acetoxy-4-chloro-5'-methyl-3H-spiro[furo[3,4-c]pyridine-1,3'-pyrrolidine]-1'-carboxylate: $Ac_2O$ (0.42 g, 4.0 mmol) was added dropwise to a solution of tert-butyl (5'S)-4-chloro-3-hydroxy-5'-methyl-3H-spiro[furo[3,4-c]pyridine-1,3'-pyrrolidine]-1'-carboxylate (0.69 g, 2.0 mmol), $Et_3N$ (0.61 g, 6.0 mmol), DMAP (0.49 g, 4.0 mmol) in 30 ml dry DCM, and stirred at rt for 3 h. The mixture was poured into saturated $NH_4Cl$ solution and extracted twice with DCM. The organic layer was washed with brine and concentrated. The crude was purified by column chromatography on silica gel to give the title compound (0.65 g, Yield 85%).

Compound 77.4: tert-Butyl (5'S)-4-chloro-5'-methyl-3H-spiro[furo[3,4-c]pyridine-1,3'-pyrrolidine]-1'-carboxylate: To a solution of tert-butyl (5'S)-3-acetoxy-4-chloro-5'-methyl-3H-spiro[furo[3,4-c]pyridine-1,3'-pyrrolidine]-1'-carboxylate (0.65 g, 1.7 mmol) in 30 ml DCM were subsequently added triethylsilane (1.9 ml 12 mmol) and boron trifluoride etherate (1.5 ml, 12 mmol) at rt. The reaction mixture was heated at reflux overnight. Cooled down and diluted with DCM. The organic layer was washed with aqueous 2M NaOH solution. To the mixture, di-tert-butyl decarbonate (0.41 g, 1.87 mmol) was added. The mixture was stirred 1 h at rt. The aqueous layer was extracted with DCM (2×). The combined organic layer was dried over sodium sulfate and concentrated. The crude was purified by chromatography on silica gel to give the title compound (0.45 g, 82% yield). LCMS (ESI): [M+H] 325.

Compound 77.5: tert-Butyl (5'S)-4-methoxy-5'-methyl-3H-spiro[furo[3,4-c]pyridine-1,3'-pyrrolidine]-1'-carboxylate: To a solution of tert-butyl (5'S)-4-chloro-5'-methyl-3H-spiro[furo[3,4-c]pyridine-1,3'-pyrrolidine]-1'-carboxylate (0.45 g, 1.40 mmol) in methanol (20 mL) was added sodium methoxide (0.38 g, 7.0 mmol). The reaction was refluxed overnight. After cooling to rt, the solvent was removed under vacuo. The residue was diluted with EtOAc (20 mL), washed water, brine, dried over $Na_2SO_4$. The solution was concentrated to give the title compound (0.30 g, 67% yield). LCMS (ESI): [M+H] 321.

Compound 77.6: (5'S)-4-Methoxy-5'-methyl-3H-spiro[furo[3,4-c]pyridine-1,3'-pyrrolidine]: The title compounds were prepared in an analogous manner of that in Compound 64.3 from tert-butyl (5'S)-4-methoxy-5'-methyl-3H-spiro[furo[3,4-c]pyridine-1,3'-pyrrolidine]-1'-carboxylate. LCMS (ESI): [M+H] 221.

The title compounds were prepared in an analogous manner of that in Example 31 from (5'S)-4-methoxy-5'-methyl-3H-spiro[furo[3,4-c]pyridine-1,3'-pyrrolidine] and N-(5-(chloromethyl)-4-fluorothiazol-2-yl)acetamide. $^1H$ NMR (400 MHz, METHANOL-$d_4$) δ 8.17 (d, J=5.27 Hz, 1H), 7.06 (d, J=5.27 Hz, 1H), 5.02-5.13 (m, 2H), 4.72 (d, J=14.56 Hz, 1H), 4.51 (d, J=14.81 Hz, 1H), 3.98 (s, 4H), 3.76 (dd, J=1.76, 11.80 Hz, 1H), 3.52 (br d, J=11.80 Hz, 1H), 2.89 (br dd, J=10.04, 14.05 Hz, 1H), 2.17-2.26 (m, 4H), 1.56-1.62 (m, 3H). LCMS (ESI): [M+H] 393.

Example 78: N-(5-(((5'S)-4-Methoxy-5'-methyl-3H-spiro[furo[3,4-c]pyridine-1,3'-pyrrolidin]-1'-yl)methyl)thiazol-2-yl)acetamide

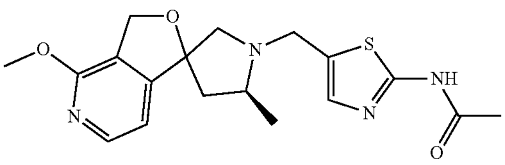 [SMILES: COc1nccc2c1COC21C[C@H](C)N(Cc2cnc(NC(C)=O)s2)C1]

The title compounds were prepared in an analogous manner of that in Example 31 from (5'S)-4-methoxy-5'-methyl-3H-spiro[furo[3,4-c]pyridine-1,3'-pyrrolidine] and N-(5-(chloromethyl)thiazol-2-yl)acetamide. $^1$H NMR (400 MHz, METHANOL-$d_4$) δ 8.17 (d, J=5.27 Hz, 1H), 7.63 (s, 1H), 7.04 (d, J=5.27 Hz, 1H), 5.01-5.12 (m, 2H), 4.79-4.85 (m, 1H), 4.59 (br d, J=14.31 Hz, 1H), 3.95-4.09 (m, 4H), 3.68 (br d, J=11.29 Hz, 1H), 3.54 (d, J=11.80 Hz, 1H), 2.88 (br dd, J=9.91, 14.18 Hz, 1H), 2.18-2.27 (m, 4H), 1.51-1.59 (m, 3H). LCMS (ESI): [M+H] 375.

Example 79: N-(4-Fluoro-5-(((5'S)-5'-methyl-7H-spiro[furo[3,4-b]pyridine-5,3'-pyrrolidin]-1'-yl)methyl)thiazol-2-yl)acetamide

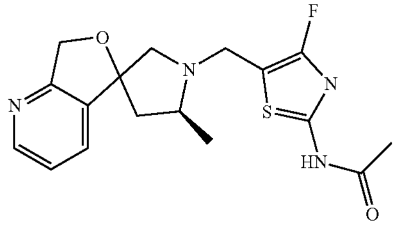

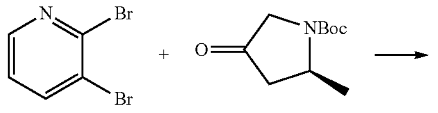

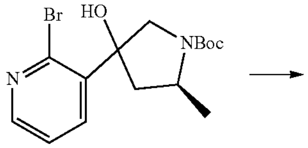

79.1

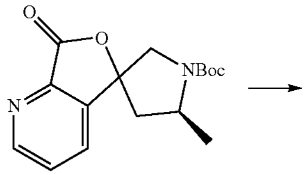

79.2

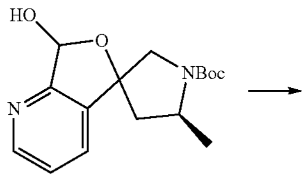

79.3

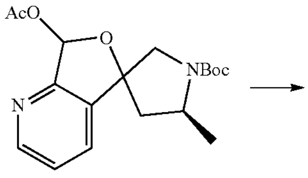

79.4

-continued

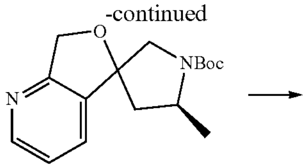

79.5

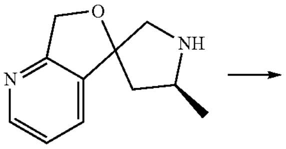

79.6

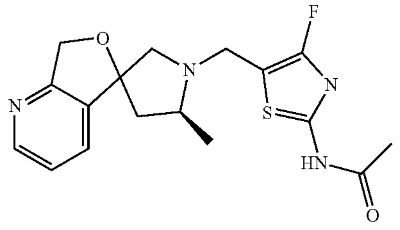

79

Compound 79.1: tert-Butyl (2S)-4-(2-bromopyridin-3-yl)-4-hydroxy-2-methylpyrrolidine-1-carboxylate: Isopropylmagnesium chloride (2.0M in THF, 11.6 ml, 23.0 mmol) was dropwise added to a solution of 2,3-dibromopyridine (5.0 g, 21.0 mmol) in THF (50 ml) at rt and the mixture stirred at rt for 1 h. To the mixture, a solution of tert-butyl (S)-2-methyl-4-oxopyrrolidine-1-carboxylate (4.25 g, 21.0 mmol) in THF (15 ml) was added. The mixture was then stirred at rt overnight. The reaction was quenched with aq. $NH_4Cl$, extracted with EtOAc (3×). The combined organic layer was then washed with water, brine, then dried and concentrated. The crude was purified by chromatography on silica gel to give the title compound (3.1 g, yield 41%). LCMS (ESI): [M+H] 357. (Ref. US20080161332, page 18, by Roche)

Compound 79.2: tert-Butyl (5'S)-5'-methyl-7-oxo-7H-spiro[furo[3,4-b]pyridine-5,3'-pyrrolidine]-1'-carboxylate: To a pressure reactor, tert-butyl (2S)-4-(2-bromopyridin-3-yl)-4-hydroxy-2-methylpyrrolidine-1-carboxylate (4.65 g, 13.0 mmol), $Et_3N$ (7.3 ml, 52.0 mmol), palladium (II) acetate (0.29 g, 1.3 mmol), triphenylphosphine (0.34 g, 1.3 mmol) and dry MeOH (50 ml) were charged. The reactor was sealed and CO gas (100 psi) was applied. The mixture was stirred at 100° C. overnight. Cooled to rt, the mixture was concentrated, diluted with DCM, washed with water, brine, then dried and concentrated. The crude was purified by chromatography on silica gel to give the title compound (1.90 g, yield 48%). LCMS (ESI): [M+H] 305.

Compound 79.3: tert-Butyl (5'S)-7-hydroxy-5'-methyl-7H-spiro[furo[3,4-b]pyridine-5,3'-pyrrolidine]-1'-carboxylate: Diisobutylaluminium hydride (1.0M in toluene, 10.0 ml, 10.0 mmol) was added dropwise to a solution of tert-butyl (5'S)-5'-methyl-7-oxo-7H-spiro[furo[3,4-b]pyridine-5,3'-pyrrolidine]-1'-carboxylate (1.5 g, 5.0 mmol) in dry DCM (50 ml) at −78° C. After stirring at −78° C. for 1 h, the mixture was poured into a saturated solution of $NH_4Cl$. The mixture was extracted twice with DCM. The organic layer was separated, washed with brine and concentrated. The crude was purified by column chromatography on silica gel to give the title compound (1.0 g, Yield 65%). LCMS (ESI): [M+H] 307.

Compound 79.4: tert-Butyl (5'S)-7-acetoxy-5'-methyl-7H-spiro[furo[3,4-b]pyridine-5,3'-pyrrolidine]-1'-carboxylate: $Ac_2O$ (0.63 g, 6.0 mmol) was added dropwise to a solution of tert-butyl (5'S)-7-hydroxy-5'-methyl-7H-spiro[furo[3,4-b]pyridine-5,3'-pyrrolidine]-1'-carboxylate (1.00 g, 3.0 mmol), $Et_3N$ (0.91 g, 9.0 mmol), DMAP (0.74 g, 6.0 mmol) in dry DCM (50 ml) at rt. The solution was stirred at rt for 3 h, then poured into saturated solution of $NH_4Cl$ which was extracted twice with DCM. The organic layer was separated, washed with brine, dried and concentrated. The crude was purified by column chromatography on silica gel to give the title compound (0.80 g, Yield 76%).

Compound 79.5: tert-Butyl (5'S)-5'-methyl-7H-spiro[furo[3,4-b]pyridine-5,3'-pyrrolidine]-1'-carboxylate: The title compounds were prepared in an analogous manner of that in Compound 77.4 from tert-butyl (5'S)-7-acetoxy-5'-methyl-7H-spiro[furo[3,4-b]pyridine-5,3'-pyrrolidine]-1'-carboxylate. Yield 38%. LCMS (ESI): [M+H] 291.

Compound 79.6: (5'S)-5'-Methyl-7H-spiro[furo[3,4-b]pyridine-5,3'-pyrrolidine]: The title compounds were prepared in an analogous manner of that in Compound 1.3 from tert-butyl (5'S)-5'-methyl-7H-spiro[furo[3,4-b]pyridine-5,3'-pyrrolidine]-1'-carboxylate. Yield 104%. LCMS (ESI): [M+H] 191.

The title compounds were prepared in an analogous manner of that in Example 31 from (5'S)-5'-methyl-7H-spiro[furo[3,4-b]pyridine-5,3'-pyrrolidine] and N-(5-(chloromethyl)-4-fluorothiazol-2-yl)acetamide. Yield 55%, $^1H$ NMR (400 MHz, METHANOL-$d_4$) δ 8.55 (dd, J=1.25, 5.02 Hz, 1H), 7.92 (dd, J=1.51, 7.78 Hz, 1H), 7.44 (dd, J=5.02, 7.78 Hz, 1H), 5.09 (s, 2H), 4.73 (d, J=14.81 Hz, 1H), 4.52 (d, J=14.81 Hz, 1H), 3.94-4.08 (m, 1H), 3.83 (dd, J=1.76, 11.80 Hz, 1H), 3.55 (d, J=11.80 Hz, 1H), 2.93 (br dd, J=9.91, 14.18 Hz, 1H), 2.27 (br dd, J=5.40, 13.93 Hz, 1H), 2.19-2.23 (m, 3H), 1.60 (d, J=6.78 Hz, 3H); LCMS (ESI): [M+H] 363.

Example 80: N-(5-(((5'S)-5'-Methyl-7H-spiro[furo[3,4-b]pyridine-5,3'-pyrrolidin]-1'-yl)methyl)thiazol-2-yl)acetamide

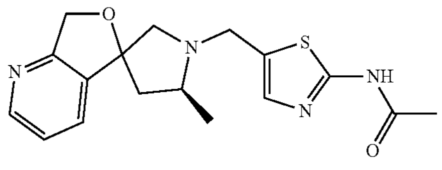 [SMILES: CC(=O)Nc1ncc(CN2CC3(C[C@@H]2C)OCc2ncccc23)s1]

The title compounds were prepared in an analogous manner of that in Example 31 from (5'S)-5'-methyl-7H-spiro[furo[3,4-b]pyridine-5,3'-pyrrolidine] and N-(5-(chloromethyl)thiazol-2-yl)acetamide. $^1H$ NMR (400 MHz, METHANOL-$d_4$) δ 8.55 (dd, J=1.25, 5.02 Hz, 1H), 7.92 (dd, J=1.25, 7.78 Hz, 1H), 7.64 (s, 1H), 7.44 (dd, J=5.02, 7.78 Hz, 1H), 5.08 (s, 2H), 4.80-4.85 (m, 1H), 4.60 (br d, J=14.31 Hz, 1H), 4.03 (br s, 1H), 3.75 (br d, J=11.29 Hz, 1H), 3.58 (d, J=12.05 Hz, 1H), 2.92 (br dd, J=9.91, 14.18 Hz, 1H), 2.28 (br dd, J=4.39, 14.18 Hz, 1H), 2.22 (s, 3H), 1.58 (d, J=6.53 Hz, 3H); LCMS (ESI): [M+H] 345.

Example 81: N-(4-Fluoro-5-((4-methoxy-3H-spiro[furo[3,4-c]pyridine-1,3'-piperidin]-1'-yl)methyl)thiazol-2-yl)acetamide

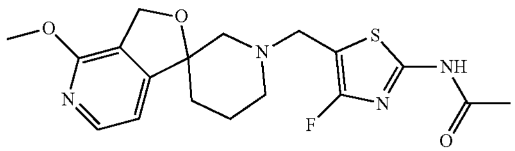

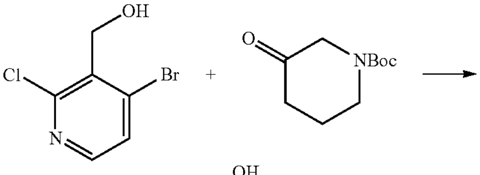

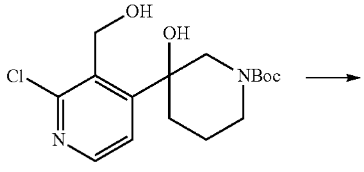

81.1

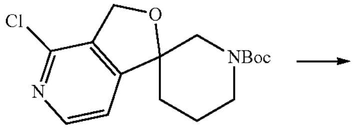

81.2

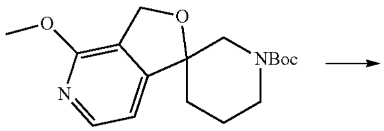

81.3

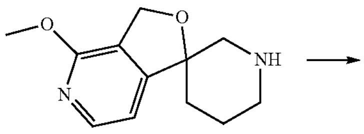

81.4

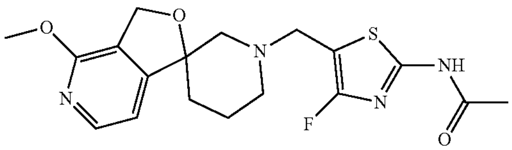

81

Compound 81.1: tert-Butyl 3-(2-chloro-3-(hydroxymethyl)pyridin-4-yl)-3-hydroxypiperidine-1-carboxylate: Under argon atmosphere, n-BuLi (2.5M in hexanes, 540 mL, 1.35 mol) was added at −78° C. to a stirred solution of (4-bromo-2-chloropyridin-3-yl) methanol (145 g, 650 mmol) in dry THF (2.0 L). After stirred at −78° C. for 0.5 h, a solution of tert-butyl 3-oxopiperidine-1-carboxylate (129.5 g, 650 mmol) in THF (200 mL) was added and the resulting solution was stirred at rt for 6 h. The mixture was poured into saturated solution of $NH_4Cl$ (300 mL) and extracted twice with $Et_{20}$. The combined organic layer was washed with brine and concentrated. The crude was purified by column chromatography to give the title compound (90 g, 40% yield). LCMS (ESI): [M+H] 343.

Compound 81.2: tert-Butyl 4-chloro-3H-spiro[furo[3,4-c]pyridine-1,3'-piperidine]-1'-carboxylate: Under argon atmosphere, n-BuLi (2.5M in hexanes, 80 mL, 200 mmol) was added at −78° C. to a stirred solution of tert-butyl 3-(2-chloro-3-(hydroxymethyl)pyridin-4-yl)-3-hydroxypiperidine-1-carboxylate (34.3 g, 100 mmol) in dry THF (1.0 L). Stirred at −78° C. for 0.5 h. A solution of p-toluenesulfonyl chloride (19.1 g, 100 mmol) in THF (100 mL) was then added and the resulting solution was stirred at rt for 6 h. The mixture was poured into aq. $NH_4Cl$ (300 mL) and extracted twice with $Et_{2O}$. The combined organic layer was washed with brine and concentrated. The crude was purified by column chromatography to give the title compound (13.6 g, 42% yield). LCMS (ESI): [M+H] 325.

Compound 81.3: tert-Butyl 4-methoxy-3H-spiro[furo[3,4-c]pyridine-1,3'-piperidine]-1'-carboxylate: Under argon atmosphere, sodium hydride (3.00 g, 75 mmol) was added to MeOH (1.0 L) at 0° C. and stirred at rt for 1 h. tert-butyl 4-chloro-3H-spiro[furo[3,4-c]pyridine-1,3'-piperidine]-1'-carboxylate (8.12 g, 25 mmol) and CuI (5.14 g, 27 mmol) were then added, and the reaction mixture was refluxed for 24 h. Cooled down, the mixture was poured into water (300 mL), concentrated under reduced pressure to half the volume, and EtOAc (500 mL) was added. The organic layer was separated, washed with water, then brine. The crude was purified by column chromatography to provide the title compound (6 g, 75% yield). LCMS (ESI): [M+H] 321.

Compound 81.4:4-Methoxy-3H-spiro[furo[3,4-c]pyridine-1,3'-piperidine]: The title compound was prepared in an analogous manner of that in Compound 1.3 from tert-butyl 4-methoxy-3H-spiro[furo[3,4-c]pyridine-1,3'-piperidine]-1'-carboxylate. LCMS (ESI): [M+H] 221.

The title compound was prepared in an analogous manner of that in Example 64 from 4-methoxy-3H-spiro[furo[3,4-c]pyridine-1,3'-piperidine] and N-(5-(chloromethyl)-4-fluorothiazol-2-yl)acetamide. $^1H$ NMR (500 MHz, DMSO-$d_6$) δ 12.21 (s, 1H), 8.08 (d, J=5.19 Hz, 1H), 7.12 (d, J=5.19 Hz, 1H), 4.85-4.98 (m, 2H), 3.88 (s, 3H), 3.53-3.65 (m, 2H), 2.51-2.56 (m, 1H), 2.47 (br s, 3H), 2.12 (s, 3H), 1.68-1.81 (m, 2H), 1.59-1.67 (m, 2H); LCMS (ESI): [M+H] 393.

Example 82: N-(5-((4-Methoxy-3H-spiro[furo[3,4-c]pyridine-1,3'-piperidin]-1'-yl)methyl)thiazol-2-yl)acetamide

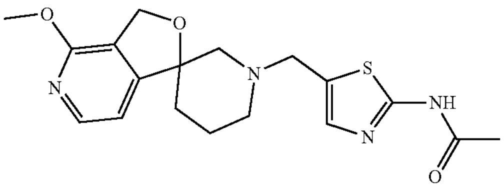 [SMILES: COc1nccc2c1COC21CCCN(Cc2cnc(NC(C)=O)s2)C1]

The title compound was prepared in an analogous manner of that in Example 64 from 4-methoxy-3H-spiro[furo[3,4-c]pyridine-1,3'-piperidine] and N-(5-(chloromethyl)thiazol-2-yl)acetamide. $^1H$ NMR (500 MHz, DMSO-$d_6$) δ 11.93 (s, 1H), 8.08 (d, J=5.19 Hz, 1H), 7.23 (s, 1H), 7.14 (d, J=5.19 Hz, 1H), 4.84-4.98 (m, 2H), 3.88 (s, 3H), 3.59-3.74 (m, 2H), 2.52 (s, 1H), 2.40-2.48 (m, 3H), 2.08-2.13 (m, 3H), 1.68-1.81 (m, 2H), 1.58-1.68 (m, 2H); LCMS (ESI): [M+H] 375.

Example 83: N-(5-((4-Chloro-3H-spiro[furo[3,4-c]pyridine-1,3'-piperidin]-1'-yl)methyl)-4-fluorothiazol-2-yl)acetamide

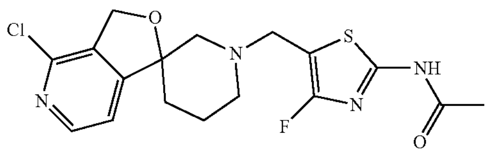

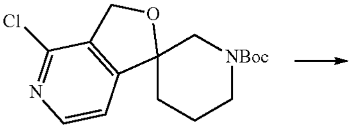

81.2

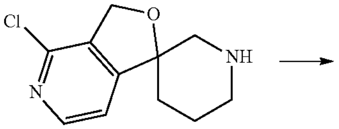

83.1

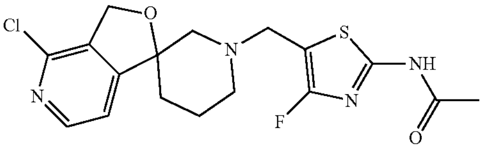

83

Compound 83.1:4-Chloro-3H-spiro[furo[3,4-c]pyridine-1,3'-piperidine]: The title compound was prepared in an analogous manner of that in Compound 64.3 from tert-butyl 4-chloro-3H-spiro[furo[3,4-c]pyridine-1,3'-piperidine]-1'-carboxylate (Compound 81.2). LCMS (ESI): [M+H] 225.

The title compound was prepared in an analogous manner of that in Example 1 from 4-chloro-3H-spiro[furo[3,4-c]pyridine-1,3'-piperidine] and N-(4-fluoro-5-formylthiazol-2-yl)acetamide. $^1H$ NMR (400 MHz, METHANOL-$d_4$) δ 8.24-8.39 (m, 1H), 7.54 (d, J=5.02 Hz, 1H), 5.03-5.14 (m, 2H), 3.58-3.75 (m, 2H), 2.58-2.65 (m, 4H), 2.17 (s, 3H), 1.67-1.97 (m, 4H). LCMS (ESI): [M+H] 397.

Example 84: (R)—N-(5-((4-Chloro-3H-spiro[furo[3,4-c]pyridine-1,3'-piperidin]-1'-yl)methyl)-4-fluorothiazol-2-yl)acetamide and(S)—N-(5-((4-chloro-3H-spiro[furo[3,4-c]pyridine-1,3'-piperidin]-1'-yl)methyl)-4-fluorothiazol-2-yl)acetamide: rac-N-(5-((4-chloro-3H-spiro[furo[3,4-c]pyridine-1,3'-piperidin]-1'-yl)methyl)-4-fluorothiazol-2-yl)acetamide

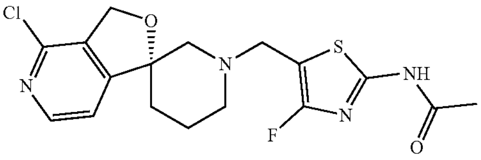

-continued

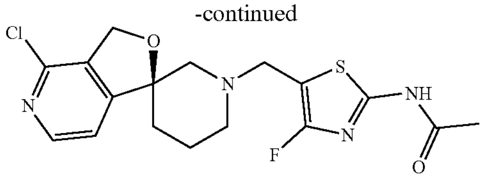

(Example 83, 77 mg) was purified by SFC (using a Chiralpak IC, 30×250 mm column and 40% of IPA (containing 0.1% $Et_2NH$) in $CO_2$ as the mobile phase, flow rate of 100 mL/min, ABPR 120 bar, MBPR 60 psi, column temperature of 40° C.) to give in order of elution:

Peak 1 (absolute stereochemistry was arbitrarily assigned), (R)—N-(5-((4-chloro-3H-spiro[furo[3,4-c]pyridine-1,3'-piperidin]-1'-yl)methyl)-4-fluorothiazol-2-yl)acetamide (21 mg mg, 27%). $^1H$ NMR (400 MHz, DMSO-$d_6$) δ 12.22 (s, 1H), 8.35 (d, J=5.02 Hz, 1H), 7.58 (d, J=5.02 Hz, 1H), 4.89-5.15 (m, 2H), 3.52-3.75 (m, 2H), 2.35-2.73 (m, 4H), 2.12 (s, 3H), 1.54-1.86 (m, 4H). LCMS. (ESI): [M+H] 397.

Peak 2 (absolute stereochemistry was arbitrarily assigned), (S)—N-(5-((4-chloro-3H-spiro[furo[3,4-c]pyridine-1,3'-piperidin]-1'-yl)methyl)-4-fluorothiazol-2-yl)acetamide (21 mg mg, 27%). $^1H$ NMR (400 MHz, DMSO-$d_6$) δ 12.22 (s, 1H), 8.35 (d, J=5:02 Hz, 1H), 7.57 (d, J=5.02 Hz, 1H), 4.87-5.15 (m, 2H), 3.49-3.77 (m, 2H), 2.35-2.72 (m, 4H), 2.12 (s, 3H), 1.49-1.89 (m, 4H). LCMS (ESI): [M+H] 397.

Example 85: N-(5-((4-Chloro-3H-spiro[furo[3,4-c]pyridine-1,3'-piperidin]-1'-yl)methyl)thiazol-2-yl)acetamide

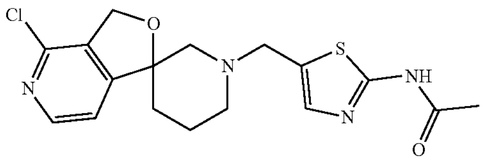 [SMILES: CC(=O)Nc1ncc(CN2CCCC3(C2)OCc2c3ccnc2Cl)s1]

The title compound was prepared in an analogous manner of that in Example 2 from 4-chloro-3H-spiro[furo[3,4-c]pyridine-1,3'-piperidine] (Compound 83.1) and N-(5-(chloromethyl)thiazol-2-yl)acetamide. $^1H$ NMR (400 MHz, METHANOL-$d_4$) δ 11.93 (s, 1H), 8.35 (d, J=5.02 Hz, 1H), 7.60 (d, J=4.77 Hz, 1H), 7.23 (s, 1H), 4.90-5.10 (m, 2H), 3.57-3.79 (m, 2H), 2.54-2.63 (m, 2H), 2.40-2.48 (m, 2H), 2.45 (s, 1H), 2.10 (s, 3H), 1.50-1.84 (m, 4H). LCMS (ESI): [M+H] 379.

Example 86: N-(4-Fluoro-5-((4-oxo-4,5-dihydro-3H-spiro[furo[3,4-c]pyridine-1,3'-piperidin]-1'-yl)methyl)thiazol-2-yl)acetamide

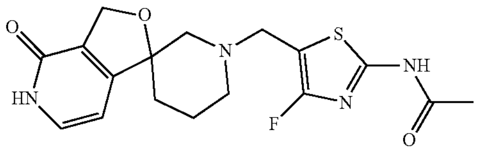

-continued

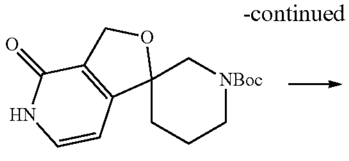

81.3

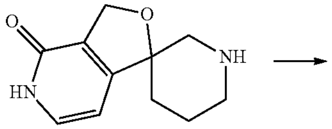

86.1

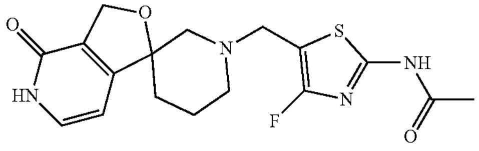

86

Compound 86.1:3,5-Dihydro-4H-spiro[furo[3,4-c]pyridine-1,3'-piperidin]-4-one: To solution of tert-butyl 4-methoxy-3H-spiro[furo[3,4-c]pyridine-1,3'-piperidine]-1'-carboxylate (Compound 81.3, 16.0 g, 50 mmol) in $Et_2O$ (200 mL) was added a saturated solution of HCl in dioxane (50 mL). After the solution had been stirred for 24 h, solid was filtered and crude product was purified by column chromatography to give the title compound (1 g, 7% yield). LCMS (ESI): [M+H] 207.

The title compound was prepared in an analogous manner of that in Example 31 from 3,5-dihydro-4H-spiro[furo[3,4-c]pyridine-1,3'-piperidin]-4-one and N-(5-(chloromethyl)-4-fluorothiazol-2-yl)acetamide. $^1H$ NMR (400 MHz, DMSO-$d_6$) δ 12.21 (s, 1H), 11.64 (br s, 1H), 7.33 (br d, J=6.78 Hz, 1H), 7.29-7.39 (m, 1H), 6.36 (d, J=6.53 Hz, 1H), 4.69-4.80 (m, 2H), 3.53-3.65 (m, 2H), 2.52-2.62 (m, 2H), 2.34-2.48 (m, 2H), 2.12 (s, 3H), 1.65-1.81 (m, 2H), 1.55-1.65 (m, 2H); LCMS (ESI): [M+H] 379.

Example 87: N-(5-((4-Oxo-4,5-dihydro-3H-spiro[furo[3,4-c]pyridine-1,3'-piperidin]-1'-yl)methyl)thiazol-2-yl)acetamide

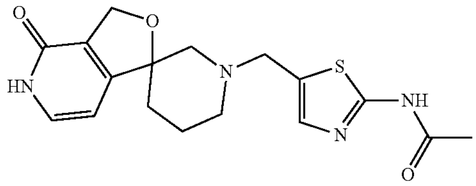 [SMILES: CC(=O)Nc1ncc(CN2CCCC3(C2)OCc2c3cc[nH]c2=O)s1]

The title compound was prepared in an analogous manner of that in Example 31 from 3,5-dihydro-4H-spiro[furo[3,4-c]pyridine-1,3'-piperidin]-4-one and N-(5-(chloromethyl)thiazol-2-yl)acetamide. $^1H$ NMR (400 MHz, METHANOL-$d_4$) δ 7.44 (d, J=6.53 Hz, 1H), 7.26-7.38 (m, 1H), 6.57 (br d, J=4.27 Hz, 1H), 4.90-5.00 (m, 2H), 3.61-4.21 (m, 2H), 2.55-2.97 (m, 4H), 2.20 (s, 3H), 2.01 (br d, J=19.32 Hz, 1H), 1.82 (br d, J=15.06 Hz, 3H), 1.31 (br d, J=7.53 Hz, 3H). LCMS (ESI): [M+H] 361.

Example 88: N-(5-((5H-Spiro[furo[3,4-d]pyrimidine-7,3'-piperidin]-1'-yl)methyl)-4-fluorothiazol-2-yl)acetamide

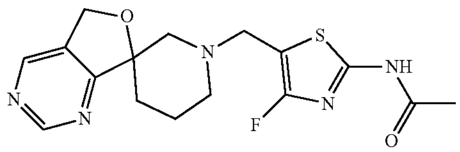

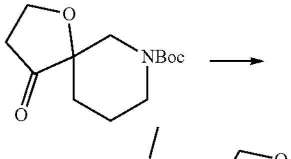

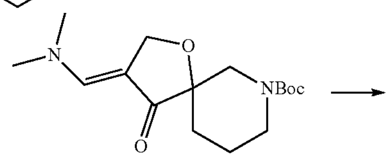

88.1

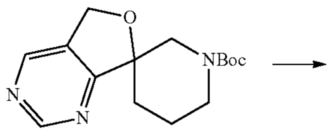

88.2

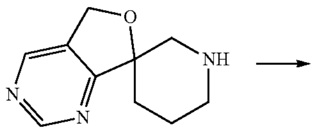

88.3

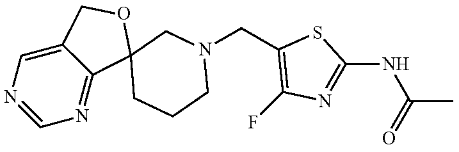

88

Compound 88.1: tert-Butyl (E)-3-((dimethylamino)methylene)-4-oxo-1-oxa-7-azaspiro[4.5]decane-7-carboxylate: A mixture of tert-butyl 4-oxo-1-oxa-7-azaspiro[4.5]decane-7-carboxylate (11 g, 43.1 mmol) and DMFDMA (9.7 g, 81.4 mmol) in toluene (500 mL) was stirred at rt overnight. The resulting mixture was concentrated under reduced pressure, triturated with $Et_2O$, filtered, and dried to afford the title compound (10 g, 74%) as white solid.

Compound 88.2: tert-Butyl 5H-spiro[furo[3,4-d]pyrimidine-7,3'-piperidine]-1'-carboxylate: Potassium tert-butoxide (5.4 g, 48.1 mmol) was added in portions to pentanol (100 mL) under stirring. To this solution, formimidamide (5 g, 48.0 mmol, acetate salt) was added in portions. The reaction mixture was stirred at rt for 1 h. tert-butyl (E)-3-((dimethylamino)methylene)-4-oxo-1-oxa-7-azaspiro[4.5]decane-7-carboxylate (5 g, 16.1 mmol) was then added. The mixture was then heated at 110° C. overnight. Cooled down, the reaction mixture was poured into ice water, and extracted with EtOAc (3×100 mL). The combined organic layer was washed with water and then brine, dried over $Na_2SO_4$, and concentrated to afford the title compound (3.5 g, 75% yield) with small amount of pentanol. LCMS (ESI): [M+H] 292.

Compound 88.3: 5H-Spiro[furo[3,4-d]pyrimidine-7,3'-piperidine]: To a solution of tert-butyl 5H-spiro[furo[3,4-d]pyrimidine-7,3'-piperidine]-1'-carboxylate (3.5 g, 12.0 mmol) in THF (50 mL) was added 10% solution of HCl in dioxane (10 mL) and the resulting mixture was stirred overnight at rt. The reaction mixture was poured into 5% $NH_3$ in ice water and extracted with EtOAc (5×70 mL). The organic layers were combined, dried over $Na_2SO_4$, and concentrated under reduced pressure. The crude was purified by column chromatography to give the title compound (1.77 g, 77% yield). LCMS (ESI): [M+H] 192.

The title compounds were prepared in an analogous manner of that in Example 31 from 5H-spiro[furo[3,4-d]pyrimidine-7,3'-piperidine] and N-(5-(chloromethyl)-4-fluorothiazol-2-yl)acetamide. $^1H$ NMR (400 MHz, METHANOL-$d_4$) δ 9.14 (t, J=0.88 Hz, 1H), 8.81 (s, 1H), 5.24 (d, J=0.75 Hz, 2H), 4.50 (s, 2H), 3.59 (br d, J=11.80 Hz, 1H), 3.49-3.55 (m, 1H), 3.37-3.44 (m, 1H), 3.24 (br t, J=11.55 Hz, 1H), 2.24-2.35 (m, 1H), 2.20-2.23 (m, 3H), 2.01-2.12 (m, 2H), 1.89-1.97 (m, 1H); LCMS (ESI): [M+H] 364.

Example 89: N-(5-((5H-Spiro[furo[3,4-d]pyrimidine-7,3'-piperidin]-1'-yl)methyl)thiazol-2-yl)acetamide

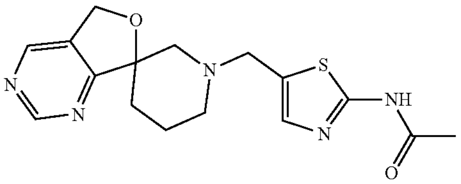 [SMILES: CC(=O)Nc1ncc(CN2CCCC3(C2)OCc2cncnc23)s1]

The title compounds were prepared in an analogous manner of that in Example 31 from 5H-spiro[furo[3,4-d]pyrimidine-7,3'-piperidine] and N-(5-(chloromethyl)thiazol-2-yl)acetamide. $^1H$ NMR (400 MHz, METHANOL-$d_4$) δ 9.13 (t, J=0.88 Hz, 1H), 8.79 (s, 1H), 7.58 (s, 1H), 5.23 (s, 2H), 4.61 (br s, 2H), 3.61 (br d, J=10.79 Hz, 1H), 3.33-3.48 (m, 2H), 3.15-3.27 (m, 1H), 2.24-2.36 (m, 1H), 2.19-2.23 (m, 3H), 2.00-2.14 (m, 2H), 1.89-1.99 (m, 1H); LCMS (ESI): [M+H] 346.

Example 90: N-(5-((3H-spiro[furo[2,3-c]pyridine-2,3'-pyrrolidin]-1'-yl)methyl)-4-fluorothiazol-2-yl)acetamide

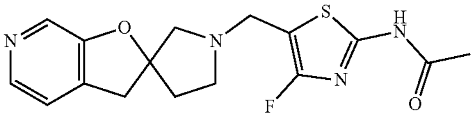 [SMILES: CC(=O)Nc1nc(F)c(CN2CCC3(Cc4ccncc4O3)C2)s1]

The title compound was prepared in an analogous manner of that in Example 1 from 3H-spiro[furo[2,3-c]pyridine-2,3'-pyrrolidine] hydrogen chloride and N-(4-fluoro-5-formylthiazol-2-yl)acetamide. LCMS (ESI): [M+H] 349.

Example 91: N-(5-((3H-spiro[furo[3,2-b]pyridine-2,3'-pyrrolidin]-1'-yl)methyl)-4-fluorothiazol-2-yl)acetamide

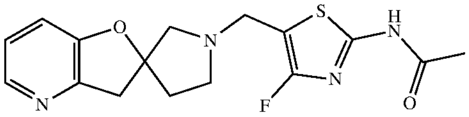 [SMILES: CC(=O)Nc1nc(F)c(CN2CCC3(Cc4ncccc4O3)C2)s1]

The title compound was prepared in an analogous manner of that in Example 1 from 3H-spiro[furo[3,2-b]pyridine-2,3'-pyrrolidine] hydrogen chloride and N-(4-fluoro-5-formylthiazol-2-yl)acetamide. LCMS (ESI): [M+H] 349.

Biological Data

OGA Enzyme Inhibition Biochemical Assay

OGA Enzyme Inhibition Biochemical Assay

Recombinant full length human OGA enzyme was purchased from Origene. 4-MUGlcNAc substrate was purchased from Sigma. All other reagents were purchased from Sigma or Fisher. Assay buffer consists of the McIlvaine buffer system, pH 6.4 (0.2M $Na_2HPO_4$ mixed with 0.1M citric acid) and 0.01% BSA. Reactions consist of 1 nM OGA, 100 μM 4-MUGlcNAc ($K_m$), and compound in a final volume of 10 μl. Reactions were incubated for 90 minutes at room temperature and quenched with 40 μl of 3M glycine, pH 10 and read on a Perkin Elmer Envision plate reader (Ex: 355 nm/Em: 460 nm). Compounds were tested with a 10-point dose-response starting from 20 μM with a 4-fold dilution. Data was fit using GraphPad Prism using a 4-parameter fit with variable slope.

Description of Cellular OGA-Tau MSD Assay

HEK-293T cells were transfected with OGT and Tau-V5 plasmids using Lipofectamine and grown overnight. Next day, the cells were collected and re-plated at $1\times10^5$ cells per well in 96 well plates. Cells were incubated for 4 hr at 37° C., before compounds were added at 1 uM, with 3-fold dilutions in a 10-point titration. Cell plates were incubated with compounds overnight at 37° C. The next day media was removed from wells by gentle aspiration and 120 ul of 1× Cell Lysis buffer mixed with protease and phosphatase cocktail added to each well. A freeze thaw was performed at −80° C., then mixed before transferring 50 μl to MSD plates coated with V5-tag antibody to capture Tau. MSD Plates were incubated overnight at 4° C., on a plate shaker. The following day, plates were washed and incubated with Tau-S400-GlcNAc antibody for 2 hr and then developed with rabbit Sulfo-tag antibody. Final read out was carried out on an MSD 600 reader. The data was analyzed using Graph Pad or Genedata, the data was normalized and % activity versus log of compound concentration was plotted. The ICso values were obtained from a 4 parameter fit.

Description of Rat Liver Microsome Stability Assay

Compound (1 μM final concentration) was incubated with rat liver microsomes (0.5 mg/mL) in 0.1M sodium phosphate buffer (pH 7.4) plus 3.3 mM magnesium chloride in the presence or absence of 1 mM nicotinamide adenine dinucleotide phosphate (NADPH) at 37° C. Aliquots (40 uL) at 0, 5, 10, 15, 25 and 40 minutes post NADPH addition (or compound addition for reactions in absence of NADPH) were transferred into individual 96-well plate wells containing 40 ng/ml of 8-cyclopently-1,3-dipropylxanthine (CPDPX, internal standard) in 160 uL acetonitrile:methanol (1:1 v/v). The sample-containing plates were centrifuged (10 minutes, 3220× g) and 50 μL of the supernatant from each well was transferred into a clean analytical sample 96-well plate well containing 300 μL of 20:80:0.1 acetonitrile/water/formic acid, mixed, then directly injected onto an LC/MS/MS system for sample analysis.

HPLC and Mass Spectrometer Conditions for Stability Assays

The LC/MS/MS system consisted of an ultra high throughput RapidFire® 300 system (Agilent Technologies, Santa Clara, CA) coupled to a Triple Quad 5500 mass spectrometer (ABSciex, Foster City, CA). Sample load and wash were performed on a RapidFire® C4 cartridge using 0.1% formic acid in water as mobile phase A and sample elution using 0.1% formic acid in acetonitrile:methanol (1:1 v/v) as mobile phase B.

RapidFire® Operating Conditions:

TABLE 1

| RapidFire ® Flow Program Process | | | |
|---|---|---|---|
| | Duration (ms) | Mobile Phase | Flow Rate (mL/min) |
| Aspirate | 1200 | A | 1.0 |
| Load/Wash | 4000 | A | 1.0 |
| Elute | 7000 | B | 1.0 |
| Re-equilibrate | 500 | A | 1.0 |

Mass Spectrometer Operating Conditions:

TABLE 2

| MRM Parameters | | | | | | |
|---|---|---|---|---|---|---|
| Q1 Mass (amu) | Q3 Mass (amu) | Dwell (msec) | | Declustering Potential | Collision Energy | Collision Exit Potential |
| 305.2 | 263.1 | 50 | 180 | 30 | 15 | CPDPX |

| Source Parameters | Parameter Setting |
|---|---|
| CAD Gas | 9 |
| Curtain Gas | 30 |
| Ion Source Gas 1 | 60 |
| Ion Source Gas 2 | 70 |
| Ion Spray Voltage | 5500 |
| Temperature | 600 |

Data Analysis:

CLint, app (apparent intrinsic clearance) was calculated using the following equation for microsome stability.

$$CL_{int,app}=\frac{0.693}{T_{\frac{1}{2}in\,vitro}}\times\frac{\text{incubation volume}}{\text{mg of microsomal protein}}\times\frac{\text{45 mg microsomal protein}}{\text{gram liver}}\times\frac{20^{a}\text{ grams of livers}}{\text{kg body weight}}$$

where "a" represents 45 grams of liver/kg of body weight for rat.

$CL_{int,app}$ (apparent intrinsic clearance) was calculated using the following equation for hepatocyte stability:

$CL_{hep}$ (hepatic clearance) was calculated using the following equation for microsomes $$CL_{hep} = \frac{Q_h \times CL_{int,app}}{Q_h + CL_{int,app}}$$

using 55 mL/minute/kg as Qh (hepatic blood flow) for rat.

Description of the MDR1-MDCK Efflux Ratio Assay

MDR1-MDCK cell monolayers were grown to confluence on microporous polyester membranes in 96-well Corning insert plates. The permeability assay buffer was Hanks' Balanced Salt Solution containing 10 mM HEPES at pH of 7.4. Loperamide (1 μM) was used as a positive control P-gp substrate. Propranolol and Bestatin (1 μM) were used as high and low permeability comparators, respectively.

Test compounds or positive control P-gp substrate/permeability comprators were added to respective apical and basolateral chambers for bidirectional assessment of permeability. Receiver buffer (transport buffer supplemented with 1% bovine serum albumin) was added to respective receiver chambers. MDR1-MDCK cells were incubated with test compounds at 37° C. with 5% $CO_2$ for 2 hr. Samples were collected from the donor chamber at both 0 and 120 minutes, and from the receiver chamber at 120 minutes. Test and control compound concentrations were determined using LC-MS/MS analysis. Each determination was performed in triplicate. The apparent permeability ($P_{app}$), efflux ratio and mass balance (percent recovery) were calculated as follows:

$$P_{app}=(dC_r/dt)\times V_r/(A\times C_E)$$

$$\text{Mass balance}=100\times((V_r\times C_r^{final})+(V_d\times C_d^{final}))/(V_d\times C_E)$$

$$\text{Efflux ratio}=P_{app(B\text{-}A)}/P_{app(A\text{-}B)}$$

where:

$dC_r/dt$ is the cumulative concentration in the receiver compartment versus time in μM $s^{-1}$ $V_r$ is the volume of the receiver compartment in $cm^3$ $V_d$ is the volume of the donor compartment in $cm^3$ A is the area of the insert (0.143 $cm^2$ for 96-well insert)

$C_E$ is the estimated experimental concentration (Time=0) of the dosing solution $C_r^{final}$ is the concentration of the receiver at the end of the incubation period $C_d^{final}$ is the concentration of the donor at the end of the incubation period.

The following Table 1 shows the activity data for some of the compounds of the present invention. In some instances, the OGA inhibition, MDR1-MDCK efflux ratio, and rat liver microsome stability assays were repeated and whenever the final data in subsequent assays was different, the data is provided below and indicated with an asterisk (*). The symbol "-" indicates that the data is not available.

| Example | OGA Biochemical $IC_{50}$ (μM) | OGA (S400 O-GLCNAC) $IC_{50}$ (μM) | MDR1-MDCK Efflux Ratio (B-A/A-B) | RLM % Qh (%) |
|---|---|---|---|---|
| 1 | 0.015 | 0.865 | 1.2 | 97 |
| 2 | 0.027 | 0.041 | 1.9 | 97 |
| 3 | 0.330 | 1.000 | 1.7 | 81 |
| 4 | 0.360 | >1.000 | 3.1 | 78 |
| 5 | 0.150 | — | 1.1 | 77 |

-continued

| Example | OGA Biochemical $IC_{50}$ (μM) | OGA (S400 O-GLCNAC) $IC_{50}$ (μM) | MDR1-MDCK Efflux Ratio (B-A/A-B) | RLM % Qh (%) |
|---|---|---|---|---|
| 6 | 0.140 | — | 0.8 | 78 |
| 7 | 0.054 | 0.301 | 6.7 | 46 |
| 8 | 0.074 | 0.654 | 9.4 | 47 |
| 9 | 0.001 | 0.012 | 8.1 | 89 |
| 10 | 0.001 | 0.008 | 5.2 | 75 |
| 11 | 0.006 | 0.009 | 8.4 | 70 |
| 12 | 0.035 | 0.093 | 25.6 | 59 |
| 13 | 0.13 | 0.796 | — | — |
| 14 | 3.800 | — | — | — |
| 15 | 1.700 | — | — | — |
| 16 | <0.001 | 0.002 | 2.9 | 77 |
| 17 | <0.001 | 0.008 | 5.5 | 76 |
| 18 | 0.002 | 0.004 | 42 | 89 |
| 19-a | 0.001 | 0.005 | 14 | 62 |
| 19-b | 0.007 | — | 11 | 72 |
| 20 | <0.001 | 0.004 | 5.8 | 89 |
| 21 | 0.007 | 0.006 | 4.9 | 48 |
| 22 | 0.017 | 0.025 | 11 | 39 |
| 23 | 0.001 | 0.013 | 14 | 66 |
| 24 | 0.001 | 0.012 | 6.5 | 75 |
| 25 | 0.006 | 0.023 | — | — |
| 26 | 0.003 | 0.005 | 5.6 | 51 |
| 27 | 0.011 | 0.016 | 12.5 | 44 |
| 28 | <0.001 | 0.001 | 11.4 | 76 |
| 29 | <0.001 | 0.003 | 17.7 | 55 |
| 30 | <0.001 | 0.008 | 17.7 | 64 |
| 31 | <0.001 | 0.015 | 19.9 | 78 |
| 32 | <0.001 | 0.007 | 24 | 59 |
| 33 | <0.001 | 0.002 | 22 | 82 |
| 34 | <0.001 | 0.001 | 19.7 | 63 |
| 35 | <0.001 | 0.004 | 39.5 | 50 |
| 36 | <0.001 | 0.008 | 9.3 | 51 |
| 37 | <0.001 | 0.009 | 38 | 37 |
| 38 | 0.0012 | 0.0099 | 29.5 | 42 |
| 39 | 0.0005 | 0.0049 | 9.7 | 52 |
| 40 | 0.0015 | 0.014 | 27 | 54 |
| 41 | <0.001 | 0.008 | 19.5 | 65 |
| 42 | 0.0019 | 0.014 | 25 | 66 |
| 43 | <0.001 | 0.008 | 17.5 | 75 |
| 44 | <0.001 | 0.013 | 61 | 56 |
| 45 | <0.001 | 0.003 | 94 | 65 |
| 46 | <0.001 | 0.003 | 2.9 | 77 |
| 47 | <0.001 | 0.009 | 9.2 | 53 |
| 48 | 0.0014 | 0.034 | 12 | 16 |
| 49 | 0.001 | 0.073 | 2.5 | 16 |
| 50 | 0.0023 | 0.009 | 19.3 | 73 |
| 51 | 0.091 | 0.059 | — | — |
| 52 | 0.18 | >1 | 2.6 | 74 |
| 53 | 0.073 | 0.532 | 0.6 | 98 |
| 54 | 1.5 | >1 | 0.8 | 94 |
| 55 | 0.0245 | 0.25 | 5.5 | 96 |
| 56 | 0.017 | 0.112 | 2.2 | 97 |
| 57 | 0.17 | 0.818 | 2.4 | 88 |
| 58 | 0.0042 | 0.014 | 1.7 | 95 |
| 59 | 0.009 | 0.016 | 3.5 | 94 |
| 60 | 1.7 | >1 | — | — |
| 61 | 0.029 | — | 26 | 82 |
| 62 | 0.044 | 0.073 | — | — |
| 63 | 0.013 | 0.057 | 26 | 78 |
| 64-a | 0.01 | 0.118 | 34 | 85 |
| 64-b | 0.17 | — | — | — |
| 65-a | 0.024 | — | — | — |
| 65-b | 0.44 | — | — | — |
| 66 | 0.21 | 0.794 | — | — |
| 67 | 0.12 | 1 | — | — |
| 68 | 0.006 | 0.018 | 10.7 | 84 |
| 69 | 0.0032 | 0.0138 | 13.8 | 86 |
| 70-a | 0.0014 | 0.0084 | 15 | 85 |
| 70-b | 0.85 | >1 | 20.2 | 89 |
| 71-a | 0.15 | — | — | — |
| 71-b | 0.26 | — | — | — |
| 72-a | 0.03 | — | — | — |
| 72-b | 0.11 | — | — | — |
| 73 | 0.0092 | 0.0237 | 21.6 | 78 |
| 74 | 0.013 | 0.0226 | 36.5 | 75 |

-continued

| Example | OGA Biochemical $IC_{50}$ (μM) | OGA (S400 O-GLCNAC) $IC_{50}$ (μM) | MDR1-MDCK Efflux Ratio (B-A/A-B) | RLM % Qh (%) |
|---|---|---|---|---|
| 75-a | 0.010 | 0.040 | 7.8 | 59 |
| 75-b | 0.047 | 0.024 | 5.4 | 89 |
| 76-a | 0.055 | 0.062 | 17.7 | 58 |
| 76-b | 0.160 | 0.038 | 8.9 | 89 |
| 77 | 0.004 | 0.007 | 3.4 | 91 |
| 78 | 0.065 | 0.009 | 7.9 | 93 |
| 79 | 0.01 | 0.005 | — | — |
| 80 | 0.049 | 0.015 | — | — |
| 81 | 0.0011 | 0.0151 | 2.5 | 78 |
| 82 | 0.0016 | 0.126 | 4.4 | 78 |
| 83 | 0.0059 | 0.0183 | 4.2 | 82 |
| 84-a | 0.0026 | 0.0085 | 3.0 | 86 |
| 84-b | 0.31 | >1 | 5.3 | 77 |
| 85 | 0.0045 | 0.017 | 8.0 | 84 |
| 86 | 0.0145 | 0.138 | 32.6 | 37 |
| 87 | 0.035 | 0.0543 | — | — |
| 88 | 0.0208 | 0.0903 | — | — |
| 89 | 0.0679 | 0.0846 | — | — |
| 90 | 0.120 | — | — | — |
| 91 | 0.070 | — | — | 45 |

While we have described a number of embodiments of this, it is apparent that our basic examples may be altered to provide other embodiments that utilize the compounds and methods of this disclosure. Therefore, it will be appreciated that the scope of this disclosure is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

ABSTRACT OF THE DISCLOSURE

Described herein are compounds represented by formula (I) or formula (Ia)

(I)

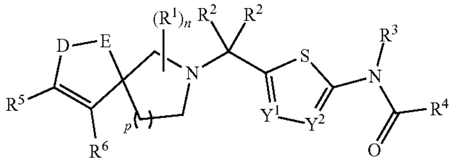

(Ia)

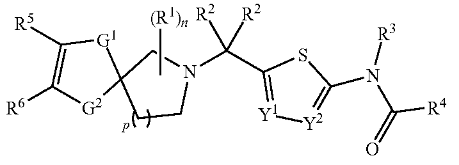

or a pharmaceutically acceptable salt thereof, pharmaceutical compositions comprising the same and methods of preparing and using the same. The variables $R^1$, $R^2$, $R^3$, $R^4$, $R^5$, $R^6$, $Y^1$, $Y^2$, D, E, $G^1$, $G^2$, n and p are as defined herein.

What is claimed is:

1. A compound represented by the following structural formula:

(I)

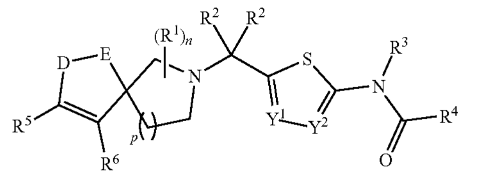

or a pharmaceutically acceptable salt thereof, wherein:

$Y^1$ and $Y^2$ are each CR or N, wherein at least one of $Y^1$ or $Y^2$ is N;

$R^c$ is —H, halo, $C_1$-$C_4$ alkyl, or $C_1$-$C_4$ haloalkyl;

p is 1 or 2;

n is 0 or an integer from 1 to 8;

when n is other than 0, $R^1$, for each occurrence, is independently halo, $C_1$-$C_4$ alkyl, $C_1$-$C_4$ haloalkyl, or $C_1$-$C_4$ alkoxy;

$R^2$, for each occurrence, is independently —H, halo, $C_1$-$C_4$ alkyl, $C_1$-$C_4$ haloalkyl, $C_3$-$C_{10}$ cycloalkyl, or $C_3$-$C_{10}$ halocycloalkyl; or alternatively two $R^2$ together with the carbon atom to which they are attached form a $C_3$-$C_{10}$ cycloalkyl;

$R^3$ is —H or $C_1$-$C_4$ alkyl;

$R^4$ is $C_1$-$C_4$ alkyl, $C_1$-$C_4$ haloalkyl, or $C_3$-$C_6$ cycloalkyl; or alternatively $R^3$ and $R^4$ taken together with their intervening atoms form a 5 to 7 membered heterocycle, wherein said heterocycle is optionally substituted with 1, 2 or 3 substituents independently selected from the group consisting of halo, $C_1$-$C_4$ alkyl, $C_1$-$C_4$ haloalkyl, and $C_1$-$C_4$ alkoxy;

D-E is selected from the group consisting of $CH_2CH_2$, O—$CH_2$, and $CH_2$—O;

$R^5$ and $R^6$ are joined to form an aryl, a 5 or 6 membered heteroaryl or a partially saturated heterocyclic group, fused with the ring containing D-E, in which the ring formed by $R^5$ and $R^6$ may optionally contain 1, 2 or 3 heteroatoms independently selected from nitrogen, oxygen and sulfur and said ring may be optionally substituted with 1, 2 or 3, $R^7$ substituents, where $R^7$ is independently selected from the group consisting of halo, hydroxyl, oxo, $NR^8R^9$, cyano, $C_1$-$C_4$ alkyl, $C_1$-$C_4$ haloalkyl, $C_1$-$C_4$ alkoxy, $C_3$-$C_{10}$ cycloalkyl, and $C_3$-$C_{10}$ halo-cycloalkyl, wherein said $C_1$-$C_4$ alkyl, $C_1$-$C_4$ alkoxy or $C_3$-$C_{10}$ cycloalkyl, are optionally substituted with 1, 2 or 3 substituents independently selected from halo, hydroxyl, $C_1$-$C_4$ haloalkyl and $C_1$-$C_4$ alkoxy; and $R^8$ and $R^9$ are independently selected from H, $C_1$-$C_4$ alkyl, $C_3$-$C_6$ cycloalkyl and $C_1$-$C_4$ alkyl-$C_1$-$C_4$ alkoxy; or $R^8$ and $R^9$ may combine together with the nitrogen atom to which they are attached form a $C_3$-$C_6$ heterocycloalkyl ring said ring may contain one additional heteroatom selected from N and O, wherein said heterocycloalkyl group may be optionally substituted with 1 or 2 $C_1$-$C_4$ alkyl.

2. The compound according to claim 1, wherein the compound is represented by the following structural formula:

(II)

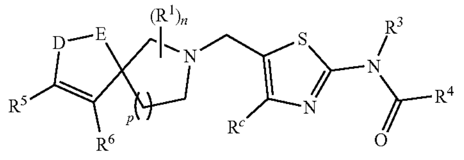

or a pharmaceutically acceptable salt thereof.

3. The compound according to claim 2, or a pharmaceutically acceptable salt thereof, wherein:

The bicyclic ring formed by D-E, $R^5$ and $R^6$ is selected from the group consisting of:

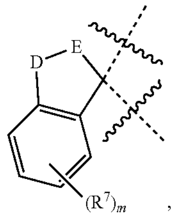 , 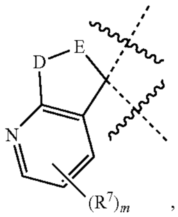 ,

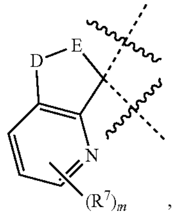 , 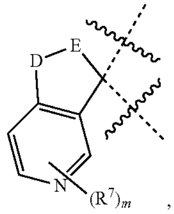 ,

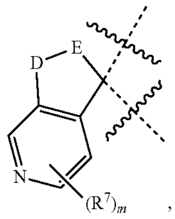 , 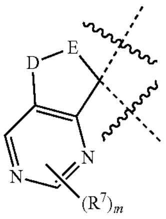

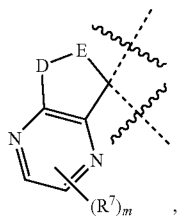 , 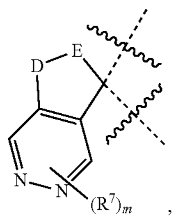 ,

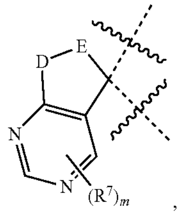 , 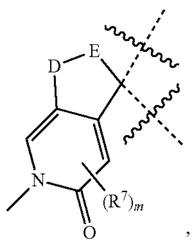 , and

-continued

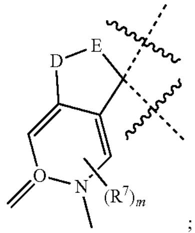 ;

where D-E is selected from the group consisting of $CH_2CH_2$, O—$CH_2$, and $CH_2$—O;

m is 0 or 1;

$R^7$ is independently selected from the group consisting of halo, hydroxyl, $NR^8R^9$, $C_1$-$C_4$ alkyl, $C_1$-$C_4$ haloalkyl, $C_1$-$C_4$ alkoxy, $C_3$-$C_{10}$ cycloalkyl, and $C_3$-$C_{10}$ halocycloalkyl, wherein said $C_1$-$C_4$ alkyl, $C_1$-$C_4$ alkoxy or $C_3$-$C_{10}$ cycloalkyl, are optionally substituted with 1, 2 or 3 substituents independently selected from halo, hydroxyl, $C_1$-$C_4$ haloalkyl and $C_1$-$C_4$ alkoxy; and $R^8$ and $R^9$ are independently selected from H, $C_1$-$C_4$ alkyl, $C_3$-$C_6$ cycloalkyl and $C_1$-$C_4$ alkyl-$C_1$-$C_4$ alkoxy; or $R^8$ and $R^9$ may combine together with the nitrogen atom to which they are attached form azetidine, piperazine, morpholine or piperidine, said piperazine, morpholine or piperidine may be optionally substituted with 1 or 2 $C_1$-$C_4$ alkyl.

4. The compound according to claim 3, or a pharmaceutically acceptable salt thereof, wherein:

i) $R^c$ is halo, $C_1$-$C_4$ alkyl, or $C_1$-$C_4$ haloalkyl;

D-E is $CH_2$—O;

m is 0 or 1;

n is 0 or 1; and $R^1$ is H, halo or $C_1$-$C_4$ alkyl; or ii) $R^c$ is halo, $C_1$-$C_4$ alkyl, or $C_1$-$C_4$ haloalkyl;

D-E is O—$CH_2$;

m is 0 or 1;

n is 0 or 1; and $R^1$ is H, halo or $C_1$-$C_4$ alkyl.

5. The compound according to claim 4, wherein the bicyclic ring formed by D-E, $R^5$ and $R^6$ is selected from the group consisting of:

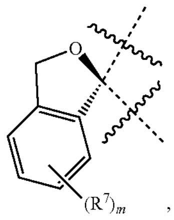 , 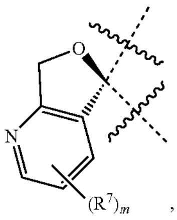 ,

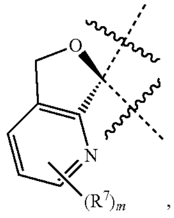 , 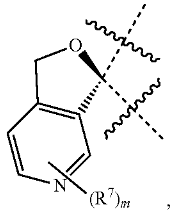 ,

-continued

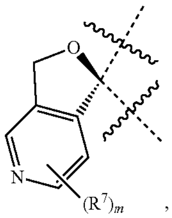
,
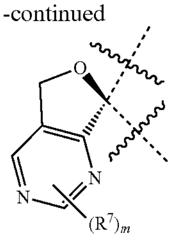
,
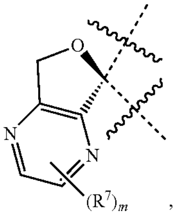
,
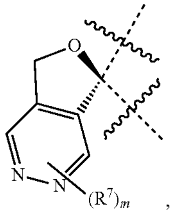
,
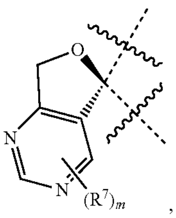
,
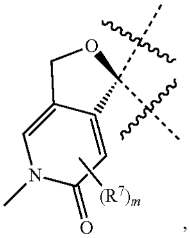
, and
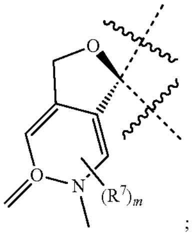
;

or a pharmaceutically acceptable salt thereof.

6. The compound according to claim 5 wherein the compound is represented by the following structural formula:

(III)

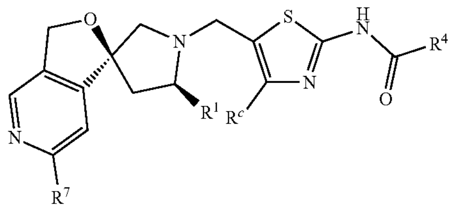

or a pharmaceutically acceptable salt thereof.

7. A compound represented by the following structural formula (Ia):

(Ia)

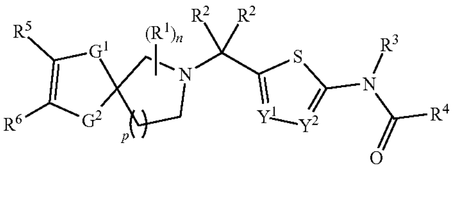

or a pharmaceutically acceptable salt thereof, wherein:

$Y^1$ and $Y^2$ are each $CR^c$ or N, wherein at least one of $Y^1$ or $Y^2$ is N;

$R^c$ is —H, halo, $C_1$-$C_4$ alkyl, or $C_1$-$C_4$ haloalkyl;

p is 1 or 2;

n is 0 or an integer from 1 to 8;

when n is other than 0, $R^1$, for each occurrence, is independently halo, $C_1$-$C_4$ alkyl, $C_1$-$C_4$ haloalkyl, or $C_1$-$C_4$ alkoxy;

$R^2$, for each occurrence, is independently —H, halo, $C_1$-$C_4$ alkyl, $C_1$-$C_4$ haloalkyl, $C_3$-$C_{10}$ cycloalkyl, or $C_3$-$C_{10}$ halocycloalkyl; or alternatively two $R^2$ together with the carbon atom to which they are attached form a $C_3$-$C_{10}$ cycloalkyl;

$R^3$ is —H or $C_1$-$C_4$ alkyl;

$R^4$ is $C_1$-$C_4$ alkyl, $C_1$-$C_4$ haloalkyl, or $C_3$-$C_6$ cycloalkyl; or alternatively $R^3$ and $R^4$ taken together with their intervening atoms form a 5 to 7 membered heterocycle, wherein said heterocycle is optionally substituted with 1, 2 or 3 substituents independently selected from the group consisting of halo, $C_1$-$C_4$ alkyl, $C_1$-$C_4$ haloalkyl, and $C_1$-$C_4$ alkoxy;

$G^1$ is O and $G^2$ is $CH_2$; or $G^1$ is $CH_2$ and $G^2$ is O;

$R^5$ and $R^6$ are joined to form an aryl, a 5 or 6 membered heteroaryl or a partially saturated heterocyclic group, fused with the ring containing $G^1$ and $G^2$, in which the ring formed by $R^5$ and $R^6$ may optionally contain 1, 2 or 3 heteroatoms independently selected from nitrogen, oxygen and sulfur and said ring may be optionally substituted with 1, 2 or 3, $R^7$ substituents, where $R^7$ is independently selected from the group consisting of halo, hydroxyl, oxo, $NR^8R^9$, cyano, $C_1$-$C_4$ alkyl, $C_1$-$C_4$ haloalkyl, $C_1$-$C_4$ alkoxy, $C_3$-$C_{10}$ cycloalkyl, and $C_3$-$C_{10}$ halo-cycloalkyl, wherein said $C_1$-$C_4$ alkyl, $C_1$-$C_4$ alkoxy or $C_3$-$C_{10}$ cycloalkyl, are optionally substituted with 1, 2 or 3 substituents independently selected from halo, hydroxyl, $C_1$-$C_4$ haloalkyl and $C_1$-$C_4$ alkoxy; and $R^8$ and $R^9$ are independently selected from H, $C_1$-$C_4$ alkyl, $C_3$-$C_6$ cycloalkyl and $C_1$-$C_4$ alkyl-$C_1$-$C_4$ alkoxy; or $R^8$ and $R^9$ may combine together with the nitrogen atom to which they are attached form a $C_3$-$C_6$ heterocycloalkyl ring said ring may contain one additional heteroatom selected from N and O, wherein said heterocycloalkyl group may be optionally substituted with 1 or 2 $C_1$-$C_4$ alkyl.

8. A compound according to claim 7 represented by formula (IIa):

(IIa)

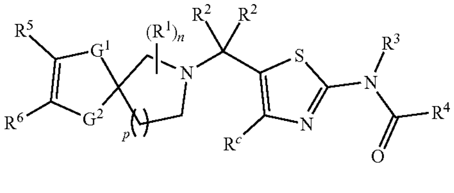

or a pharmaceutically acceptable salt thereof.

9. A compound according to claim 8 or a pharmaceutically acceptable salt thereof, wherein:

The bicyclic ring formed by $G^1$ and $G^2$, $R^5$ and $R^6$ is selected from the group consisting of:

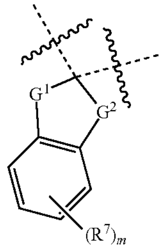 , 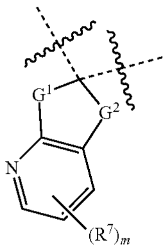 ,

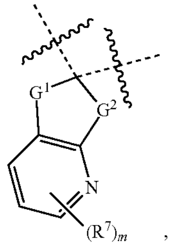 , 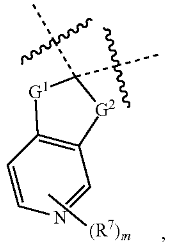 ,

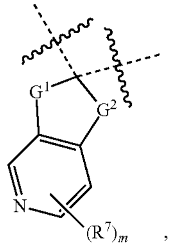 , 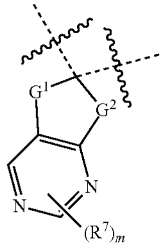 ,

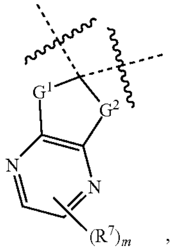 , 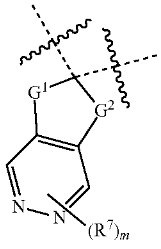 ,

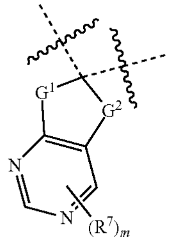 , 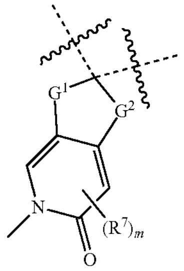 , and

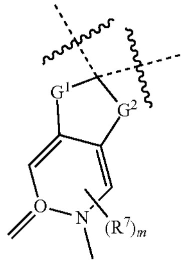 ;

m is 0 or 1;

$R^7$ is independently selected from the group consisting of halo, hydroxyl, $NR^8R^9$, $C_1$-$C_4$ alkyl, $C_1$-$C_4$ haloalkyl, $C_1$-$C_4$ alkoxy, $C_3$-$C_{10}$ cycloalkyl, and $C_3$-$C_{10}$ halocycloalkyl, wherein said $C_1$-$C_4$ alkyl, $C_1$-$C_4$ alkoxy or $C_3$-$C_{10}$ cycloalkyl, are optionally substituted with 1, 2 or 3 substituents independently selected from halo, hydroxyl, $C_1$-$C_4$ haloalkyl and $C_1$-$C_4$ alkoxy; and $R^8$ and $R^9$ are independently selected from H, $C_1$-$C_4$ alkyl, $C_3$-$C_6$ cycloalkyl and $C_1$-$C_4$ alkyl-$C_1$-$C_4$ alkoxy; or $R^8$ and $R^9$ may combine together with the nitrogen atom to which they are attached form azetidine, piperazine, morpholine or piperidine, said piperazine, morpholine or piperidine may be optionally substituted with 1 or 2 $C_1$-$C_4$ alkyl.

10. The compound according to claim 9, or a pharmaceutically acceptable salt thereof, wherein:

i) $R^c$ is halo, $C_1$-$C_4$ alkyl, or $C_1$-$C_4$ haloalkyl;

$G^1$ is O and $G^2$ is $CH_2$;

m is 0 or 1;

n is 0 or 1; and $R^1$ is H, halo or $C_1$-$C_4$ alkyl; or ii) $R^c$ is halo, $C_1$-$C_4$ alkyl, or $C_1$-$C_4$ haloalkyl;

$G^1$ is $CH_2$ and $G^2$ is O;

m is 0 or 1;

n is 0 or 1; and $R^1$ is H, halo or $C_1$-$C_4$ alkyl.

11. The compound according to claim 10 or a pharmaceutically acceptable salt thereof, wherein, the bicyclic ring formed by $G^1$, $G^2$, $R^5$ and $R^6$ is selected from the group consisting of:

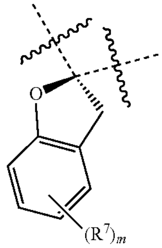 , 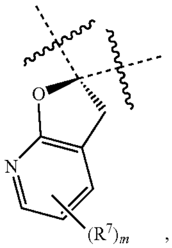 ,

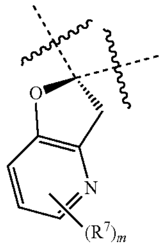 , 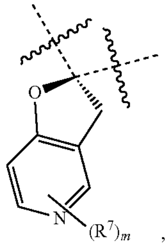 ,

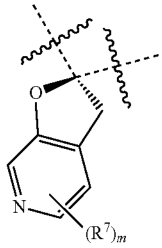 , 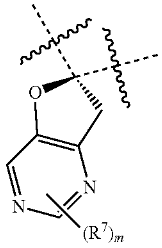 ,

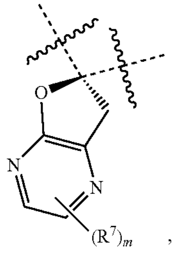 , 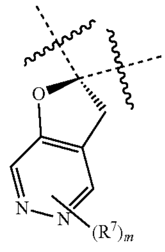 ,

-continued

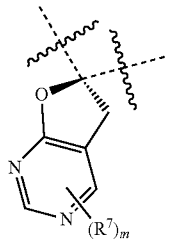,
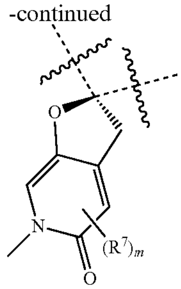, and
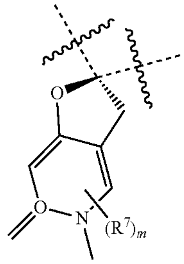;

12. The compound according to claim 10, wherein the compound is represented by the following formula:

(IIIa)

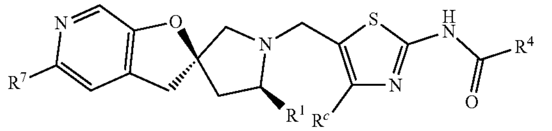

or a pharmaceutically acceptable salt thereof.

13. The compound according to claim 12 or a pharmaceutically acceptable salt thereof, wherein i) $R^1$ is halo or $C_1$-$C_4$ alkyl; $R^c$ is H or halo; and $R^4$ is $C_1$-$C_4$ alkyl; ii) $R^1$ is $C_1$-$C_4$ alkyl; $R^c$ is F; and $R^4$ is $C_1$-$C_4$ alkyl; or iii) $R^1$ is $C_1$-$C_4$ alkyl, $R^c$ is H and $R^4$ is $C_1$-$C_4$ alkyl.

14. The compound according to claim 13 or a pharmaceutically acceptable salt thereof, wherein $R^7$ is

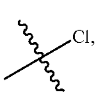
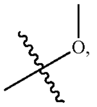
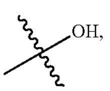
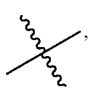
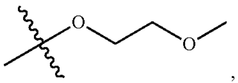,
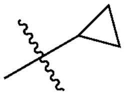,
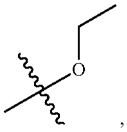,
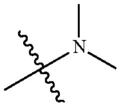,
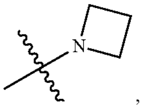, -continued

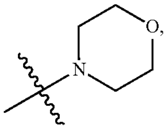
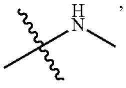,
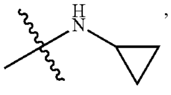,
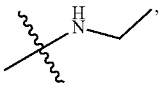
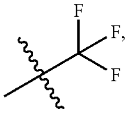
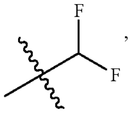,
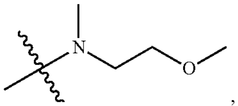,
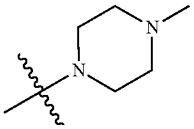,
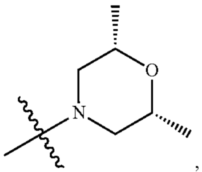, or
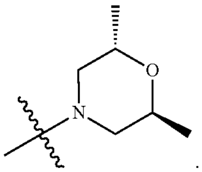.

15. The compound according to claim 14 or a pharmaceutically acceptable salt thereof, wherein $R^7$ is

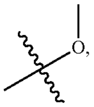 or
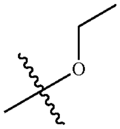.

16. A pharmaceutical composition comprising the compound according to claim 7 or a pharmaceutically acceptable salt thereof and a pharmaceutically acceptable carrier or diluent.

17. A method of treating a subject with a disease or condition that is caused, mediated and/or propagated by O-GlcNAcase activity, selected from a neurodegenerative disease, a tauopathy, diabetes, cancer and stress, comprising administering to the subject an effective amount of the compound according to claim 7.

18. The method according to claim 17, wherein the disease or condition is Alzheimer's disease.

19. A method of inhibiting O-GlcNAcase in a subject in need thereof, comprising: administering to the subject an effective amount of the compound according to claim 7.

20. A method of treating a disease or condition characterized by hyperphosphorylation of tau in the brain, comprising administering to a subject an effective amount of the compound according to claim 7.

* * * * *